US008361990B2

(12) United States Patent
Capomacchia et al.

(10) Patent No.: US 8,361,990 B2
(45) Date of Patent: Jan. 29, 2013

(54) GLUCOSAMINE AND GLUCOSAMINE/ANTI-INFLAMMATORY MUTUAL PRODRUGS, COMPOSITIONS, AND METHODS

(75) Inventors: Anthony C. Capomacchia, Bishop, GA (US); Solomon T. Garner, Jr., New Orleans, LA (US); J. Warren Beach, Horschton, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 13/229,049

(22) Filed: Sep. 9, 2011

(65) Prior Publication Data

US 2012/0021046 A1    Jan. 26, 2012

Related U.S. Application Data

(63) Continuation of application No. 11/547,898, filed as application No. PCT/US2005/011739 on Apr. 7, 2005, now Pat. No. 8,034,796.

(60) Provisional application No. 60/560,128, filed on Apr. 7, 2004.

(51) Int. Cl.
*A01N 43/04* (2006.01)
*A61K 31/70* (2006.01)

(52) U.S. Cl. ........................................................ 514/62
(58) Field of Classification Search .................... None
See application file for complete search history.

(56) References Cited

U.S. PATENT DOCUMENTS

| | | | |
|---|---|---|---|
| 4,278,679 A | 7/1981 | Madison et al. |
| 4,855,090 A | 8/1989 | Wallach |
| 4,911,928 A | 3/1990 | Wallach |
| 4,917,951 A | 4/1990 | Wallach |
| 4,942,038 A | 7/1990 | Wallach |
| 5,000,960 A | 3/1991 | Wallach |
| 5,032,457 A | 7/1991 | Wallach |
| 5,104,736 A | 4/1992 | Wallach |
| 5,147,723 A | 9/1992 | Wallach |
| 5,219,538 A | 6/1993 | Henderson et al. |
| 5,234,767 A | 8/1993 | Wallach |
| 5,474,848 A | 12/1995 | Wallach |
| 5,628,936 A | 5/1997 | Wallach |
| 5,703,119 A | 12/1997 | Baragi et al. |
| 6,083,996 A | 7/2000 | Büyüktimkin et al. |
| 6,133,230 A | 10/2000 | Anastassiades |
| 6,299,902 B1 | 10/2001 | Jun et al. |
| 6,346,519 B1 | 2/2002 | Petrus |
| 6,355,666 B1 | 3/2002 | Lai et al. |
| 6,368,618 B1 | 4/2002 | Jun et al. |
| 6,429,223 B1 | 8/2002 | Lai et al. |
| 6,479,469 B2 | 11/2002 | Anastassiades |
| 6,579,543 B1 | 6/2003 | McClung |
| 6,656,925 B2 | 12/2003 | Petrus |
| 6,677,321 B1 | 1/2004 | Levin |
| 6,685,928 B2 | 2/2004 | Uhrich et al. |
| 6,809,111 B2 | 10/2004 | Carter |
| 6,846,818 B2 | 1/2005 | DeMello et al. |
| 7,112,578 B2 | 9/2006 | Levin |
| 2002/0022052 A1 | 2/2002 | Dransfield |
| 2002/0045597 A1 | 4/2002 | Anastassiades |
| 2002/0106345 A1 | 8/2002 | Uhrich et al. |
| 2002/0119952 A1 | 8/2002 | Petrus |
| 2003/0114416 A1 | 6/2003 | Pulaski et al. |
| 2003/0114418 A1 | 6/2003 | Pulaski et al. |
| 2003/0125303 A1 | 7/2003 | Kucharchuk |
| 2004/0038948 A1 | 2/2004 | Uhrich |
| 2004/0147445 A1 | 7/2004 | Levin |
| 2004/0152665 A1 | 8/2004 | Anastassiades |
| 2004/0162269 A1 | 8/2004 | Petrus |
| 2004/0225077 A1 | 11/2004 | Gravett et al. |
| 2005/0101563 A1 | 5/2005 | Pulaski et al. |
| 2005/0215487 A1* | 9/2005 | Holick et al. .................. 514/23 |
| 2007/0014832 A1 | 1/2007 | Uhrich |
| 2007/0020254 A1 | 1/2007 | Levin |
| 2008/0020997 A1 | 1/2008 | Capomacchia et al. |

FOREIGN PATENT DOCUMENTS

| | | |
|---|---|---|
| DE | 2223051 C2 | 12/1973 |
| EP | 1 320 373 B1 | 1/2007 |
| GB | 1 383 465 A | 2/1974 |
| JP | 54 055545 A | 5/1979 |
| WO | WO 91/04013 A1 | 4/1991 |
| WO | WO 99/52528 A1 | 10/1999 |
| WO | WO 01/41753 A2 | 6/2001 |
| WO | WO 01/41783 A1 | 6/2001 |
| WO | WO 02/17890 A2 | 3/2002 |
| WO | WO 02/26239 A1 | 4/2002 |
| WO | WO 01/041753 A3 | 9/2002 |
| WO | WO 02/076423 A2 | 10/2002 |
| WO | WO 03/015797 A1 | 2/2003 |
| WO | WO 03/015799 A1 | 2/2003 |
| WO | WO 02/076423 A3 | 3/2003 |
| WO | WO 03/099013 A1 | 12/2003 |
| WO | WO 2004/002457 A2 | 1/2004 |
| WO | WO 2005/116086 A2 | 12/2005 |
| WO | WO 2005/116086 A3 | 8/2006 |

OTHER PUBLICATIONS

Aghazadeh-Habashi et al., "High performance liquid chromatographic determination of N-butyryl glucosamine in rat plasma," 2005 *J. of Chromatography B* 819:91-96.

Aghazadeh-Habashi et al., "Single Dose Pharmacokinetics and Bioavailability of Glucosamine in the Rat," 2002 *J. Pharm. Pharmaceut. Sci.* 5(2):181-184.

Akatsu et al., "Comparative Effects of Non-Steroidal Anti-inflammatory Drugs, Mefenamic acid, Metiazinic acid and glucametacin on the inflammatory response induced by subcutaneous implantation of human dental plaque and on the mitotic activity of isoproterenol-stimulated parotid glands of rats," 1986 *Cell. Mol. Biol.* 32(5):619-626.

(Continued)

*Primary Examiner* — Patrick Lewis
(74) *Attorney, Agent, or Firm* — Mueting Raasch & Gebhardt, P.A.

(57) ABSTRACT

Mutual prodrugs of glucosamine, and derivatives and analogs of glucosamine and an anti-inflammatory agent, compositions thereof, and methods for, e.g., treating disorders and conditions by administration of the compositions are provided. Topical compositions of glucosamine, and derivatives and analogs of glucosamine are also provided.

25 Claims, 17 Drawing Sheets

OTHER PUBLICATIONS

Albert, "Chemical Aspects of Selective Toxicity," 1958 *Nature* 182(4633):421-423.

Anastassiades et al., "Non-steroidal anti-inflammatory agents in the primary treatment of rheumatoid arthritis," 1979 *Can. Med. Assoc. J.* 121(8):1046-1047.

Anderson, et al., "Glucosamine effects in humans: a review of effects on glucose metabolism, side effects, safety considerations and efficacy," 2005 *Food Chem. Toxicol.* 43:187-201.

Andreozzi et al., "Enthalpy relaxation of low molecular weight PMMA: a stragegy to evaluate the Tool-Narayanaswamy-Moynihan model parameters," 2003 *J. Physics: Condensed Matter* 15(11):S1215-S1226.

Bach et al., "Percutaneous penetration enhancement and its quantification," 1998 *Eur. J. Pharm. Biopharm.* 46:1-13.

Baker et al., "The Short- and Long-Term Safety of 5-Aminosalicylate Products in the Treatment of Ulcerative Colitis," 2004 *Rev. Gastroenterol. Disord.* 4(2):86-91.

Barry, "Lipid-Protein-Partitioning theory of skin penetration enhancement," 1991 *J Cont. Release* 15:237-248.

Benini et al., "In utero exposure to nonsteroidal anti-inflammatory drugs: neonatal renal failure," 2004 *Pediatr. Nephrol.* 19(2):232-234.

Bergmann et al., "Synthesen mit Glucosamin," 1932 *Chemische Berichte* 64(5):975-980.

Bernacki et al., 1977 *J. Supramolecular Structure* 7:235-250.

Berner et al., "Alcohols," in *Percutaneous Penetration Enhancers*. Smith and Maibach (Eds.), CRC Press, Boca Raton, FL., Title page, Copyright page, Table of Contents, and pp. 45-60 (1995).

Bhosale et al., "Preparation and Characterization of Mutual Prodrugs of Ibuprofen," 2004 *Indian J. Pharm. Sci.* 66(2):158-163.

Campo et al., "Improved high-performance liquid chromatographic method to estimate aminosugars and its application to glycosaminoglycan determination in plasma and serum," 2001 *J. Chrom. B* 765:151-160.

Capelli et al., "Further Studies on Glucametacin in Rheumatoid Arthritis and in Other Chronic Types of Rheumatism," 1981 *Curr. Med. Res. Opin.* 7(4):227-233.

Capomacchia, Anthony C. "UGA-NCAT: Bridges to the Doctorate," Grant Abstract, Grant No. 1R25GM066321-01 [online]. National Institute of General Medical Sciences, National Institutes of Health, project dates Aug. 6, 2002 to Jul. 31, 2005 [retrieved on May 30, 2007]. Retrieved from the Internet: <http://crisp.cit.nih.gov/crisp/CRISP_LIB.getdoc?textkey=6545266&p_grant_num=1R25GM066321-01&p_query=&ticket=45195245&p_audit_session_id=263006114&p_keywords=>; 2 pgs.

Capomacchia, Anthony C. "UGA-NCAT: Bridges to the Doctorate," Grant Abstract, Grant No. 5R25GM066321-02 [online]. National Institute of General Medical Sciences, National Institutes of Health, project dates Aug. 6, 2002 to Jul. 31, 2005 [retrieved on Sep. 10, 2007]. Retrieved from the Internet: <http://crisp.cit.nih.gov/crisp/CRISP_LIB.getdoc?textkey=6642189&p_grant_num=5R25GM066321-02&p_query=&ticket=45195245&p_audit_session_id=263006114&p_keywords=>; 2 pgs.

Capomacchia, Anthony C. "UGA-NCAT: Bridges to the Doctorate," Grant Abstract, Grant No. 5R25GM066321-03 [online]. National Institute of General Medical Sciences, National Institutes of Health, project dates Aug. 6, 2002 to Jul. 31, 2006 [retrieved on Sep. 10, 2007]. Retrieved from the Internet: <http://crisp.cit.nih.gov/crisp/CRISP_LIB.getdoc?textkey=6797359&p_grant_num=5R25GM066321-03&p_query=&ticket=45195245&p_audit_session_id=263006114&p_keywords=>; 2 pgs.

Carstens et al., "Double-Blind Comparative Study on the Analgesic and Anti-Inflamatory Activity of Glucamethacin, Aspirin and Placebo in Oral Surgery,"1987 *Odont. Chilena* 35:31-39.

Chauviere et al., "Synthesis and Biological Activity of Nitro Heterocycles Analogous to Megazol, a Trypanocidal Lead," 2003 *J. Med. Chem.* 46:427-440.

*Chemical Market Reporter*, "Specialty Supplements are the Bright Spot in US Dietary Supplement Market," vol. 264(1) (Jul. 14, 2003).

Chlud et al., "Indometacin-glucosamid in der Behandlung der chronischen polyarthritis," 1978 *Arzneim.-Forsch. (Drug Res.)* 28 (II), Heft 7:1200-1201.

Cibere, et al., "Randomized, Double-Blind, Placebo-Controlled Glucosamine Discontinuation Trial in Knee Osteoarthritis," 2004 *Arthritis & Rheumatism (Arthritis Care & Research)* 51(5):738-745.

Clarke et al., "An Integrated Amperometry Waveform for the Direct, Sensitive Detection of Amino Acids and Amino Sugars Following Anion-Exchange Chromatography," 1999 *Anal. Chem.* 71:2774-2781.

Colombo et al., "Glucamethacin in Rheumatology: Clinical Study," 1976 *Reumatismo* 28(2):106-110.

DeArgangelis, "Sull'impiego in terapia antireumatica di un nuovo antiflogistico non steroideo: La glucosamide dell'acido (N-P. clorobenzoil-2-metil-5-metossi)-indol-3-acetico monoidrato," *Lavoro ricevuto il* 16 Inglio pp. 229-239, (1971).

Diculescu et al., "Folic acid and sulfasalazine for colorectal carcinoma chemoprevention in patients with ulcerative colitis: the old and new evidence," 2003 *Rom. J. Gastroenterol.* 12(4):283-286.

"Dietary Supplement Health and Education Act of 1994" [online]. [retrieved on May 30, 2007]. Retrieved from the Internet: <URL http://www.cfsan.fda.gov/~dms/dietsupp.html>; 4 pgs.

D'Souza et al., "Release from Polymeric Prodrugs: Linkages and Their Degradation," 2004 *J. Pharm. Sci.* 93(8):1962-1979.

Du et al., "The Bioavailability and Pharmacokinetics of Glucosamine Hydrochloride and Chondroitin Sulfate after Oral and Intravenous single Dose Administration in the Horse," 2004 *Biopharmaceutics & Drug Disposition* 25(3):109-116.

"EMYCT ®" product data sheet [online]. Pfizer: Pharmacia & Upjohn Company; New York, NY; Jun. 2007 [retrieved on Sep. 10, 2007]. Retrieved from the Internet: <http://www.pfizer.com/pfizer/download/uspi_emcyt.pdf>; 7 pgs.

Forsgren et al., "Neurologic Morbidity after Herpes Simplex Virus Type 2 Meningitis: A Retrospective Study of 40 Patients," 1988 *Scand. J Urol. Nephrol. Suppl.* 107:56-58.

Franz et al., "Dimethyl Sulfoxide," in Percutaneous Penetration Enhancers. Smith, E.W., Maibach, H.I., Eds., CRC Press, Inc., Title page, Copyright page, Table of Contents, and pp. 112-127 (1995).

Fukuhara et al., "Stereoselective Disposition of Flurbiprofen From a Mutual Prodrug with a Histamine H2-Antagonist to Reduce Gastrointestinal Lesions in the Rat," 1996 *Chirality* 8:494-502.

Fukuhara et al., "Effect of Oral Multiple-Dose Administration of Anti-inflammatory Flurbiprogen Chimera Drug on Gastric Lesion, Other Toxicities and Disposition Kinetics," 1995 *Biol. Pharm. Bull.* 18:140-147.

Gallardo et al., "Analgesic and antiinflammatory effects of glucamethacin (a nonsteroidal antiinflammatory analgesic) after the removal of impacted third molars," 1990 *Oral, Surg Oral Med Oral Pathol.* 69(2):157-160.

Garner, Jr. et al., "Transdermal Permeability of N-acetyl-d-glucosamine," 2007 *Pharm. Dev. Technol.* 12(2):169-174.

Ghodeswar et al., "Synthesis and biological evaluation of glucosamine conjugate prodrug of flurbiprofen," Mar. 2003 *Indian Drugs* 40(3):156-159.

Ghodeswar et al., "Synthesis and Pharmacological Evaluation of Mutual Prodrugs of Some Nonsteroidal Antiinflammatory Drugs with Glucosamine," 2004 *Indian J. Pharm. Sci.* 66(6):773-777.

Giordano et al., "The Therapeutic Activity of 1-(p-Chlorobenzoyl)-5-methoxy-2-methylindole-3-acetic Acid Monohydrate Glucosamide in Rheumatoid Arthritis (Double Blind Trial)," 1975 *Arzneim-Forsch. (Drug Res.)* 25:435-436.

"Glucosamine/Chondroitin Arthritis Intervention Trial (GAIT)," Abstract, ClinicalTrials.gov Identifier: NCT00032890 [online]. National Institutes of Health, Sponsors and Collaborators: Department of Veterans Affairs; National Center for Complementary and Alternative Medicine (NCCAM); and National Institute of Arthritis and Musculoskeletal and Skin Diseases (NIAMS). Project dates Apr. 2000 to Feb. 2004 [retrieved on May 30, 2007]. Retrieved from the Internet<URL: http://clinicaltrials.gov/ct/show/NCT00032890;jsessionid=02969119162CA2900F7348D17221163B?order=3>; 6 pgs.

"Glucosamine Research"[online]. The Arthritis & Glucosamine Information Center, copyright 2005. Website funded by DTC Health, Inc., Morrisville, North Carolina [retrieved on Apr. 5, 2005]. Retrieved from the Internet: <URL http://www.glucosamine-arthritis.org/glucosamine-research/index.html>; 3 pgs.

Gouze et al., "Glucosamine modulates IL-1-induced activation of rat chondrocytes at a receptor level, and by inhibiting the NF-κB pathway," 2002 FEBS Letters 510:166-170.

"Guidance for Industry. Nonsterile Semisolid Dosage Forms. Scale-Up and Postapproval Changes: Chemistry, Manufacturing, and Controls; In Vitro Release Testing and In Vivo Bioequivalence Documentation," U.S. Department of Health and Human Services, Food and Drug Administration, Center for Drug Evaluation and Research (CDER), SUPAC-SS CMC 7, Office of Training and Communication, Rockville, MD, 40 pages (May 1997).

Gurol et al., "Percutaneous absorption of ketoprofen. I. In vitro release and percutaneous absorption of ketoprofen from different ointment bases," 1996 Pharrn. Acta Helv. 71(3):205-212.

Hadgraft et al., "Feasibility Assessment in Topical and Transdermal Delivery: Mathematical Models and In Vitro Studies," in Transdermal Drug Delivery, 2nd Ed. Marcel Dekker, Inc., New York, N.Y. Title page, Copyright page, Table of Contents, and pp. 1-23 (2002).

Hanessian et al., "One-step stereocontrolled synthesis of α-anomeric carboxylic acid esters from unprotected glycosyl donors: a water-soluble aspirin pro-drug analogue," 2000 Synthesis 14:1959-1968.

Ibba et al., "Double-blind comparison of glucametacin and ketoprofen in chronic arthropathies," 1983 Curr. Med. Res. Opin. 8(5):321-326.

Imai et al., "An Evaluation of an Anti-Inflammatory-Histamine H2 Antagonist Drug Complex on Gastric Erosions in the Rat," 1993 J. Pharmacol. Exp. Ther. 265:328-333.

Itoh et al., "Use of Shed Snake Skin as a Model Membrane for In Vitro Percutaneous Penetration Studies: Comparison with Human Skin," 1990 Pharm. Res. 7:1042-1047.

Karch et al., "Adverse Drug Reactions," 1975 JAMA 234(12):1236-1241.

Klotz et al., "Topical Delivery of therapeutic agents in the treatment of inflammatory bowel disease," 2005 Adv. Drug. Deliv. Rev. 57(2):267-279.

Kromann-Andersen et al., "Reported adverse reactions to and consumption of nonsteroidal anti-inflammatory drugs in Denmark over a 17-year period," 1988 Dan. Med. Bull. 35(2):187-192.

Kurihara-Bergstrom et al., "Physicochemical Study of Percutaneous Absorption Enhancement by Dimethyl Sulfoxide: Dimethyl Sulfoxide Mediation of Vidarabine (ara-A) Permeation of Hairless Mouse Skin," 1987 J. Invest. Dermatol. 89:274-280.

LaCourse, W.R. "Pulsed Electrochemical Detection in High-Performance Liquid Chromatography," John Wiley & Sons Inc., New York, N.Y. Title page, Copyright page and Table of Contents (1997).

Lamari et al., "Analysis of glycosaminologycan-derived disaccharides in biologic samples by capillary electrophoresis and protocol for sequencing glycosaminoglycans," 2002 Biomed. Chromatogr. 16:95-102.

Lim et al., "Controversies with Aminosalicylates in Inflammatory Bowel Disease," 2004 Rev. Gastroenterol. Disord. 4(3):104-117.

Lipinski et al., "Experimental and Computational Approaches to Estimate Solubility and Permeability in Drug Discovery and Development Settings," 2001 Adv. Drug Deliv. Rev. 46(1-3):3-26.

Lopes, "Double-blind clinical evaluation of the relative efficacy of ibuprofen and glucosamine sulphate in the management of osteoarthrosis of the knee in out-patients," 1982 Curr. Med. Res. Opin. 8:145-149.

Magnusson et al., "Veterinary drug delivery: potential for skin penetration enhancement," 2001 Adv. Drug Del. Rev. 50:205-227.

Mahjour et al., "Effect of Egg Yolk Lecithins and Commercial Soybean Lecithins on In Vitro Skin Permeation of Drugs," 1990 J. Control. Release 14(3):243-252.

McAlindon et al., "Glucosamine and Chondroitin for Treatment of Osteoarthritis, A Systematic Quality Assessment and Meta-analysis," 2000 JAMA 283:1469-1475.

McAlindon et al., "Automobile Crashes and Teenaged Drivers," 2000 JAMA 284(10):1239-1245.

McAlindon et al., "Glusoamine for osteoarthritis: dawn of a new era?" 2001 The Lancet 357:247-248.

McClain et al., "Hexosamines and Insulin Resistance," 1996 Diabetes 45:1003-1009.

Menger et al., "Synthesis and Reactivity of 5-Fluorouracil/Cytarabine Mutual Prodrugs," 1997 J. Org. Chem. 62:9083-9088.

Merrick et al., "Glucosamine Metabolism. VI. Glucosaminic Acid Dehydrase," 1960 J. Biol. Chem. 235(5):1274-1280.

Milewski, "Glucosamine-6-phosphate synthase," 2002 Biochimica et Biophysica Acta 1597:173-192.

Mirelli et al., "Endoscopic Study of the Gastrointestinal Tolerance of Glucamethacin," 1978 Curr. Med. Res. Opin. 5(8):648-654.

Miwa et al., "Utility of 3-0-Methyl-N-Acetyl-D-Glucosamine, and N-Acetylglucosamine Kinase Inhibitor, for Accurate Assay of Glucokinase in Pancreatic Islets and Liver," 1994-1995 Enzyme Protein 48:135-142.

Moretti et al., "In vitro release and antiinflammatory activity of topical formulations of ketoprofen," 2000 Boll. Chim. Farm. 139(2):67-72.

Muller-Fassbender et al., "Glucosamine sulfate compared to ibuprofen in osteoarthritis of the knee," 1994 Osteoarthritis Cartilage 2:61-69.

Ohsawa et al., "Tumor-oriented anti-cancer agent with estrogen as a carrier," 1988 Gan To Kagaku Ryoho. 15(4 Pt 2):1065-1071.

Otagiri et al., "Improving the pharmacokinetic and phannacodynamic properties of a drug by chemical conversion to a chimera drug," 1999 J Control. Release 62:223-229.

Paroli et al., "Correlations of DNA, RNA and Protein Levels in Duodenal Mucosa with Antiinflammatory Potency and Disposition to Gut Damage of Non-steroidal Agents," 1978 Arzneium.-Forsch. (Drug Res.) 28(I), Heft 5:819-824.

Phoon et al., "Glucosamine for Osteoarthritis—Bogus or Cure?"[online]. The Arthritis & Glucosamine Information Center, copyright 2005. Website funded by DTC Health, Inc., Morrisville, North Carolina [retrieved on Apr. 5, 2005]. Retrieved from the Internet: <URL http://www.glucosamine-arthritis.org/glucosamine-bogus-cure.html>; 3 pgs.

Pietzsch et al., "Results of systematic screening for serious gastrointestinal bleeding associated with NSAIDs in Rostock hospitals," 2002 Int. J Clin. Pharmacol. Ther. 40(3):111-115.

Pikal et al., "Evaluation of Glassy-State Dynamics from the Width of the Glass Transition: Results from Theoretical Simulation of Differential Scanning Calorimetry and Comparisons with Experiment," 2004 J. Pharm. Sci. 93(4):981-994.

Pipino et al., "Studio clinico in <<doppio cieco>> con un farmaco antiflogistico non steroideo la <<glucametacine>>," 1980, Minerva Medica, 71:2845-2850.

Poustie et al., "N-Butyryl Glucosamine Increases Matrix Gene Expression by Chondrocytes," 2004 Pharmacol. Exp. Ther. 311(2):610-616.

Rao, "Capping Drugs: Development of Prodrugs," Resonance, 8(2):19-27 (2003); available from the Internet: <URL http://www.ias.ac.in/resonance/Feb2003/pdf/Feb2003p19-27.pdf>; 9 pages.

Ruane et al., "Glucosamine therapy compared to ibuprofen for joint pain," 2002 Br. J Community Nurs. 7:148-152.

Sandy et al., "Chondrocyte-mediated catabolism of aggrecan: aggrecanase-dependent cleavage induced by interleukin-1 or retinoic acid can be inhibited by glucosamine," 1998 Biochem. J. 335:59-66.

Seguin et al., "TNFα Suppresses Link Protein and Type II Collagen Expression in Chondrocytes: Role of MEKI/2 and NF-κB Signaling Pathways," 2003 J. Cell Physiol. 197:357-359.

Setnikar et al., "Pharmacokinetics of Glucosamine in the Dog and in Man," 1986 Arzneimittel-Forschung 36(4):729-735.

Setnikar et al., "Pharmacokinetics of Glucosamine in Man," 1993 Arzneimittel-Forschung 43(10):1109-1113.

Setnikar et al., "Absorption, Distribution, Metabolism and Excretion of Glucosamine Sulfate," 2001 Arzneimittel-Forschung 51(9):699-725.

Sheridan et al., "Mechanism Based Chemotherapy for Prostate Cancer," 1991 Cancer Surv. 11:239-254.

Shi et al., "Risk factors of adverse drug reaction from non-steroidal anti-inflammatory drugs in Shanghai patients with arthropathy," 2004 Acta Pharmacol. Sin. 25(3), 357-365.

Shikhman et al., "N-Acetylglucosamine Prevents IL-1β-Mediated Activation of Human Chondrocytes," 2001 J. Immunol. 166:5155-5160.

Silva et al., "Stereospecific Solution- and Solid-Phase Glycosylations, Synthesis of β-Linked Saccharides and Construction of Disaccharide Libraries Using Phenylsulfenyl 2-Deoxy-2-Trifluoroacetamido Glycopyranosides as Glycosyl Donors," 1999 *J. Org. Chem.* 64:5926-5929.

Singh et al., Mutual Prodrugs—A Recent Trend in Prodrug Design, 1994 *Indian J Pharm. Sci.* 56(3):69-79.

Singh et al., "Hexosamine-Induced Fibronectin Protein Synthesis in Mesangial Cells is Associated with Increases in cAMP Responsive Element binding (CREB) Phosphorylation and Nuclear CREB, The Involvement of Protein Kinases A and C," 2001 *Diabetes* 50:2355-2362.

Sinha et al., "Permeation Enhancers for Transdermal Drug Delivery," 2000 *Drug. Dev. Ind. Pharm.* 26:1131-1140.

Stenlake, "How does Glucosamine and Chondroitin Work"[online]. The Arthritis & Glucosamine Information Center, copyright 2005. Website funded by DTC Health, Inc., Morrisville, North Carolina [retrieved on Apr. 5, 2005]. Retrieved from the Internet: <URL http://www.glucosamine-arthritis.org/glucosamine/how-does-glucosamine-chondroitin-work.html>; 3 pgs.

"SYNVISC" product data sheet [online]. Genzyme Biosurgery: Genzyme Corporation; Ridgefield, NJ; Dec. 15, 2006 [retrieved Sep. 10, 2007]. Retrieved from the Internet: <http://www.synvisc.com/pdf/ussyn_synvisc_pi.pdf>; 4 pgs.

"The use of common stems in the selection of International Nonproprietary Names (INN) for pharmaceutical substances," World Health Organization: Geneva, Switzerland; 2002. Cover page, publishers page, and p. 80. Full document available online at <http://apps.who.int/medicinedocs/pdf/s4895e/s4895e.pdf>.

Theodosakis et al., "The Arthritis Cure," 1st Ed., St. Martin's Press, New York, NY. Title page, Copyright page and Table of Contents (1997).

Towheed et al., "Glucosamine therapy for osteoarthritis," *J. Rheumatol.* 1999, 26(11):2294-2297.

Towheed et al., "Glucosamine and chondroitin for treating symptoms of osteoarthritis: evidence is widely touted but incomplete," 2000 *JAMA* 283(11):1483-1484.

Towheed, "Current Status of Glucosamine Therapy in Osteoarthritis," *Arthritis & Rheumatism (Arthritis Care & Research)* 2003, 49(4):601-604.

Trivedi et al., "Vitamin E as a human skin penetration enhancer," 1995 *Eur. J. Pharm. Sci.*, 3(4):241-243.

Ueda et al., "Histamine and its Related Active Substances: Synthesis and Pharmacological Properties of a New Chimera Drug Derived From the Combination of Anti-inflammatory Agent Histamine $H_2$ Receptor Antagonist," 1990 *Mem. Inst. Sci. Ind. Res.* Osaka Univ., 47:43-54.

Van Schaftigen et al., "Glucosamine-sensitive and -insensitive detritiation of [2-$^3$H]glucose in isolated rat hepatocytes: a study of the contributions of glucokinase and glucose-6-phosphatase," 1995 *Biochem, J.* 308:23-29.

Virkamaki et al., "Allosteric Regulation of Glycogen Synthase and Hexokinase by Glucosamine-6-Phosphate During Glucosamine-Induced Insulin Resistance in Skeletal Muscle and Heart," 1999 *Diabetes* 48:1101-1107.

Viswanadhan et al., "Knowledge-based Approaches in the Design and Selection of Compound Libraries for Drug Discovery," 2002 *Curr. Opin. Drug Discov. Devel.* 5(3):400-406.

Wang et al., "Androgen Antagonistic Effect of Estramustine Phosphate (EMP) Metabolites on Wild-Type and Mutated Androgen Receptor," 1998 *Biochem. Pharmacol.* 55(9):1427-1433).

Wiholm, "Identification of Sulfoamide-like Adverse Drug Reactions to Celecoxib in the World Health Organization Database," 2001 *Curr. Med. Res. Opin.* 17 (3):210-216.

Williams et al., "Skin Absorption Enhancers," 1992 *Crit. Rev. Ther. Drug Carrier System.* 9:305-353.

Yuan et al., "The binary eutectic of NSAIDS and two-phase liquid system of enhanced membrane permeation," 2005 *Pharm. Dev. Technol.* 10(1):1-10.

Examination Report issued Jun. 25, 2008, in Singapore Patent Application No. 200606721-9, filed Sep. 27, 2006 (International filing date of Apr. 7, 2005).

International Preliminary Report on Patentability issued Oct. 11, 2006, in International Patent Application No. PCT/US2005/011739, filed Apr. 7, 2005.

Office Action issued Jun. 6, 2008, in Chinese Patent Application No. 200580014107.0, filed Nov. 1, 2006 (International filing date of Apr. 7, 2005). English language translation included.

Office Action issued Sep. 24, 2008, in Eurasian Patent Application No. 200601648, filed Oct. 5, 2006 (International filing date of Apr. 7, 2005). English language translation included.

Office Action issued Nov. 2, 2008, in Mexican Patent Application No. PA/a/2006/011475, filed Oct. 4, 2006 (International filing date of Apr. 7, 2005). English language translation only.

Office Action issued Jun. 17, 2010, in U.S. Appl. No. 11/547,898, filed Jul. 24, 2007; 5 pages.

Office Action issued Sep. 23, 2010, in U.S. Appl. No. 11/547,898, filed Jul. 24, 2007; 7 pages.

Search Report issued Nov. 8, 2007, in Singapore Patent Application No. 200606721-9, filed Sep. 27, 2006 (International filing date of Apr. 7, 2005).

Supplementary European Search Report issued on Mar. 15, 2011, in European Patent Application No. 05778582.6; 7 pages.

Written Opinion issued Dec. 12, 2005, in International Patent Application No. PCT/US2005/011739, filed Apr. 7, 2005.

Written Opinion issued Nov. 8, 2007, in Singapore Patent Application No. 200606721-9, filed Sep. 27, 2006 (International filing date of Apr. 7, 2005).

Antman et al., "Use of Nonsteroidal Antiimfiarrunatory Drugs," Mar. 27, 2007 *Circulation* 115:1634-1642.

* cited by examiner

5-Fluorouracil/Cytarabine

Ibuprofen/Paracetamol

Sulphasalazine

Ibuprofen/Salicylamide

Fig. 14

GLUCOSAMINE AND GLUCOSAMINE/ANTI-INFLAMMATORY MUTUAL PRODRUGS, COMPOSITIONS, AND METHODS

This application is a continuation application of U.S. patent application Ser. No. 11/547,898, filed Jul. 24, 2007 now U.S. Pat. No. 8,034,796 which is a U.S. National Stage Application of International Application No. PCT/US2005/011739, filed Apr. 7, 2005, which claims the benefit of U.S. Provisional Application No. 60/560,128, filed Apr. 7, 2004, each of which is incorporated herein by reference in its entirety.

STATEMENT OF GOVERNMENT RIGHTS

This invention was made with Government support under Grant GM066321 awarded by the National Institutes of Health. The Government has certain rights in the invention.

BACKGROUND OF THE INVENTION

An estimated 21 million adults in the United States alone live with osteoarthritis, one of the most common types of arthritis. Osteoarthritis, also called degenerative joint disease, is caused by the breakdown of cartilage, the connective tissue that cushions the ends of bones within the joint. Osteoarthritis is characterized by pain, joint damage, and limited joint motion. This disease generally occurs late in a patient's life, and most commonly affects the hands and larger weight-bearing joints. Additionally, age, gender (females), and obesity are risk factors for this disease.

Researchers have found that in degenerating cartilage, pro-inflammatory cytokines, such as IL-1β and TNFα, are associated with an increased degradation of cartilage matrix (Sandy et al., Biochem. J., 335:59-66 (1998); Seguin et al., J. Cell Physiol., 197:356-369 (2003)). These events are also correlated with the reduction in the cartilage matrix gene expression and syntheses in vitro (Gouze et al., FEBS Letters, 510:166-170 (2002); Shikhman et al., J. Immunol., 166: 5155-5160 (2001)).

The amino monosaccharide glucosamine, naturally occurring in cartilage and connective tissues, contributes to maintaining strength, flexibility, and elasticity of these tissues. Glucosamine is a precursor to a glycosaminglycan molecule, which is used in the formation and repair of cartilage. In vivo, glucosamine is typically converted to N-acetyl glucosamine. In recent years, glucosamine has been used widely to treat the symptoms of osteoarthritis in human and animal models, serving in an anti-inflammatory capacity in reducing joint swelling and pain levels comparable with that observed with non-steroidal anti-inflammatory drugs (NSAIDs) (Lopes, Curr. Med. Res. Opin., 8:145-149 (1982); Muller-Fassbender et al., Osteoarthritis Cartilage, 2:61-69 (1994); Ruane et al., Br. J. Community Nurs., 7:148-152 (2002)). Some have also concluded that glucosamine counteracts the degradative effects that IL-1β has on proteoglycan syntheses (Sandy et al., Biochem J., 335:59-66 (1998); Gouze et al., FEBS Letters, 510:166-170 (2002)), as glucosamine reduces nitric oxide production induced by IL-1β and TNFα (Shikhman et al., J. Immunol., 166:5155-5160 (2001)) and suppresses the syntheses of cyclooxygenase-2 (COX-2) by human chondrocytes in response to IL-1β (Largo et al., Osteoarthritis Cartilage, 11:290-298 (2003)). Thus, glucosamine may also serve in the management of diseases associated with degeneration of cartilage tissues, such as osteoarthritis.

The use of glucosamine gained popularity after being featured in the book, The Arthritis Cure by Jason Theodasakis, MD, et al. (St. Martin's Press. New York, N.Y. 1997). Between 1997 and 2002, the annual market growth rate of glucosamine has exceeded 36.4% (Chemical Market Reporter, vol. 264(1), Jul. 14, 2003). Currently, glucosamine and its metabolites are not classified as drugs, but as nutraceutical/dietary supplements under United States Food and Drug Administration's Dietary Supplement Health and Education Act of 1994 (DSHEA). Oral dosage formulations of N-acetyl-D-glucosamine and its parent compound glucosamine in salt form (sulfate, hydrochloride etc.) are commercially available nutraceuticals, and are commonly administered in conjunction with chondroitin sulfate, also a readily available nutraceutical. Glucosamine and chondroitin have been reported effective in the oral treatment of osteoarthritis but have not undergone the rigorous studies needed for FDA approval as pharmaceuticals. (Theodasakis et al., The Arthritis Cure, 1st Edition, St. Martin's Press. New York, N.Y. 1997; McAlindon et al., JAMA, 283:469-1475 (2000)). The National Institutes of Health (Bethesda, Md., USA) has an ongoing multi-center study-GAIT (Glucosamine/Chondroitin Arthritis Intervention Trial) that is currently evaluating the efficacy of orally administered glucosamine and chondroitin oral supplements (Glucosamine/Chondroitin Arthritis Intervention Trial (GAIT), National Center for Complementary and Alternative Medicine (NCCAM), and National Institute of Arthritis and Musculoskeletal and Skin Diseases (NIAMS) September 1999).

While oral administration is the most widely recognized method of administering glucosamine, the effectiveness of glucosamine administered subcutaneously has also been studied. For example, there currently exists an FDA approved therapy, SYNVISC (Genzyme Corp., Naarden, the Netherlands) for the local treatment of pain associated with osteoarthritis of the knee. The treatment includes injection of a solution including sodium hyaluronate (a glycosaminoglycan) at the affected joint. However, SYNVISC is currently approved only for treatment of the knee.

Non-steroidal anti-inflammatory drugs (NSAIDs) are effective in reducing inflammation, and are often used to treat the symptoms of osteoarthritis. However, NSAIDs may have undesirable side effects. Efforts have been made to improve the pharmaceutical properties of NSAIDs, such as permeability, solubility, and stability, by creating NSAID "prodrugs." A prodrug is a drug precursor. The term "prodrug" has been used to describe a compound that is composed of one active drug compound and a second, non-active compound. The prodrug is not active as a pharmacological agent until it undergoes a chemical conversion, e.g., via metabolic processes after administration to a patient. Once converted, the prodrug provides the active pharmaceutical agent and the nonactive compound that is typically inert after conversion.

The prodrug concept was initially articulated by Albert (Nature, 182(4633):421-423 (1958)). The original objectives of prodrug synthesis and development were to improve drug stability and to target drug delivery for drugs administered orally and intravenously. Stability is significant to drug activity, and for water and enzyme labile drugs, stability is typically achieved by protecting the drug from chemical hydrolysis and enzyme degradation subsequent to drug administration. Targeted delivery for prodrugs is based on enhancing drug solubility and permeability, and is particularly useful in drug administration associated with lipid membranes in order to penetrate the very hydrophobic blood brain barrier.

The most common form of prodrug utilizes an ester linkage formed synthetically through reaction of a carboxylic acid with an alcohol or phenol to modify the parent drug's in vivo metabolic fate. In addition to affecting the metabolism of the parent drug, the ester prodrug may possess other advantages, such as reduced side effects. For example gastric distress may be reduced if the nonsteroidal anti-inflammatory drug (NSAID) were formulated as a prodrug, as compared with the NSAID administered alone. Positive characteristics associated with prodrug usage include, for example, the presence of stable covalent ester linkage, less intrinsic activity compared to the parent drug, lower toxicity, and better release kinetics at the binding site to ensure effective drug levels.

"Mutual prodrugs," representing a variation of a prodrug, can be described as the conjugation of two drugs having different pharmacological activities. The concept arises from the practice of clinically co-administering two drugs in order to enhance pharmacological activity or prevent clinical side effects (U.S. Pat. No. 4,278,679). Mutual prodrugs are synthesized toward a pharmacological objective of improving each drug's efficacy, optimizing delivery, and lowering toxicities.

In a mutual prodrug, each component drug functions as the "pro" portion with respect to the other. Like a prodrug, a mutual prodrug is converted into the component active drugs within the body through enzymatic and/or non-enzymatic reactions. Mutual prodrugs can be classified as, for example, carrier-linked prodrugs, bio-precursor prodrugs, or chemical activation prodrugs, depending upon their constituents and composition (Albert, Nature, 182(4633):421-423 (1958); Rao, H Surya Prakash (available on the internet at ias.ac.in/resonance/Feb2003/pdf/Feb2003p19-27.pdf), Capping Drugs: Development of Prodrugs.k February, 2003). At the site of action, the side effects of the original drug would be masked allowing the drug to work more effectively (Albert, Nature, 182(4633):421-423 (1958)). Mutual prodrugs are typically similar to single active agent prodrugs in regard to pharmaceutical and pharmacological activities, such as absorption, disposition, metabolism, and excretion. The objective of a mutual prodrug is for both active drugs reaching their respective active sites, to provide the desired pharmacological effects while minimizing adverse metabolic and/or toxicological events.

For many years before the terms "prodrug" and "mutual prodrug" were coined in the research domain, combination drugs have been administered to patients as therapeutic agents (Singh et al., Indian J. Pharm. Sci, 56(3):69-79 (1994)), for example in relation to the production of sulphasalazine, representing modern advances in antibiotic prodrugs. Essentially, this has led to combinations of β-lactam antibiotics and their potentiating agents to produce, for example ampicillin-mecillinam and ampicillan-sulbactam to form sultamicillin, and Dual Action Cephalosporins as well as other agents not typically referred to as mutual prodrugs (Singh et al., Indian J. Pharm. Sci, 56(3):69-79 (1994))

One example of a mutual prodrug is estramustine sodium phosphate (EMCYT, Pharmacia, La Roche) developed in the early 1970's as an anti-neoplastic agent that shows certain mutual prodrug characteristics (Wang et al., Biochem. Pharmacol., 55(9):1427-33 (1998); Sheridan et al., Cancer Surv., 11:239-254 (1991); Ohsawa et al., Gan To Kagaku Ryoho., April; 15(4 Pt 2-1):1065-71 (1998); Forsgren et al., Urol Nephrol Suppl., 107:56-58 (1988)). Estramustine is typically used in the treatment of metastatic carcinoma of the prostate. Estramustine is selectively taken up into estrogen receptor positive cells and then, as shown in FIG. 1, the urethane linkage is hydrolyzed to give 17-alphaestradiol, which slows prostate cell growth, and nornitrogen mustard as a weak alkylating agent.

Prodrug research has continued, as exemplified by the synthesis of 5-fluorouracil/cytarabine mutual prodrugs designed to reduce the resistance mechanisms at work in the delivery of single nucleoside drugs (Menger et al., J. Org. Chem., 62:9083-9088 (1997)). Researchers such as Bhosale and co-workers have made attempts to produce mutual prodrugs of ibuprofen/paracetamol and ibuprofen/salicylaminde. The goal of this work was to produce prodrugs of NSAIDS to reduce the associated side effects (Bhosale et al., Indian J. Pharm. Sci., 66(2):158-163 (2003)). Their approach was unique from the perspective of producing mutual prodrugs vis-à-vis physicochemical modifications towards simplistic NSAID delivery, much like sulphasalazine, currently used more so as a ulcerative colitis therapeutic consisting of sulphapyridine and 5-aminosaicylic acid covalently bound via an azo bond (Klotz et al., Adv. Drug Deliv. Rev., 57(2):267-279 (2005); Lim et al., Rev. Gastroenterol. Disord., 4(3):104-117 (2004); Baker et al., Rev. Gastroenterol. Disord., 4(2): 86-91 (2004); and Diculescu et al., Rom. J. Gastroenterol., 12(4):283-286 (2003). Structures of Sulphasalazine (FIG. 2A), 5-Fluorouracil/Cytarabine (FIG. 2B), Ibuprofen/Paracetamol (FIG. 2C), and Ibuprofen/Salicylamide (FIG. 2D) are provided in FIG. 2.

SUMMARY OF THE INVENTION

The concept of a "mutual prodrug" is relatively new in medicinal chemistry, pharmaceutics, and drug delivery. A mutual prodrug is composed of two drug compounds that are covalently linked, for example, by an ester linkage (Ueda et al., Mem. Inst. Sci Res. Osaka Univ., 47:43-54 (1990); Imai et al., J. Pharmacol. Exp. Ther., 265:328-333 (1994); Fukuhara et al., Chirality, 8:494-502 (1996); Fukuhara et al., Biol. Pharm. Bull., 18:140-147 (1995); and Otagiri et al., J. Con. Release, 62:223-229 (1999)). When covalently linked, the drug components are rendered pharmaceutically inactive; however, the linkage provides some beneficial aspect to the mutual prodrug, such as improved delivery of the covalently linked drugs, as compared with delivery of each of the drugs individually. An ester linkage is easily degraded by mammalian esterase, thereby allowing release of each drug component in vivo. Each of the drug components is thereby rendered pharmaceutically active. Thus, after administration to a patient, cleavage of the mutual prodrug permits each of the drug components, pharmaceutically activated by cleavage, to produce its respective intended pharmacological action. In a mutual prodrug, each component facilitates the delivery of the other component.

In one aspect, the present invention provides a compound that functions as a mutual prodrug. The compound includes two pharmaceutically active substances. In particular, the present invention is directed to a compound including a first component covalently linked to a second component, said compound having formula I:

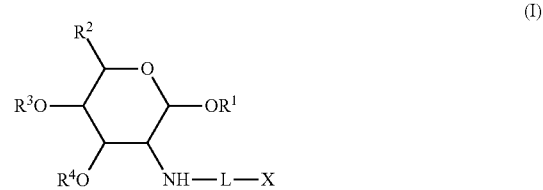

(I)

wherein $R^1$, $R^2$, $R^3$ and $R^4$ are each independently H or an organic group; L is an optional linking group; and X is an anti-inflammatory agent. In a preferred embodiment, $R^1$, $R^2$, $R^3$ and $R^4$ are each H; L is an acetyl group; and X is ibuprofen or ketoprofen.

The first component, represented by the substituted ring structure linked to X, the anti-inflammatory agent, through the linker L, is preferably glucosamine or a derivative or analog of glucosamine. The second component, X, is an anti-inflammatory agent, preferably a nonsteroidal anti-inflammatory agent (NSAID). The linker L may be present or absent in the compound having formula I. If linker L is present, the first component is considered to be indirectly linked to the second component. If linker L is absent, the first component is considered to be directly linked to the second component. The linkage between the first and second components, whether direct or indirect, is a covalent linkage.

The linkage between the first and second component is a cleavable linkage. For example, the linkage may be hydrolyzable and/or may be enzymatically cleavable. Preferably, the linkage is cleavable under physiological conditions, such as those present in a mammalian body, particularly a human body. When a linker L is used, the linkage between the first component and L is cleavable, and/or the linkage between L and the second component, X, is cleavable.

In addition to facilitating delivery of the active components, the linking of the components may impart a protective effect on the mutual prodrug, thereby reducing or preventing unwanted degradation, usually by stomach acids, and/or side effects of either or both of the drugs, prior to cleavage of the mutual prodrug in vivo. This protective effect afforded by the mutual prodrug may be particularly desirable if an NSAID is one of the drugs, in view of the side effects common to these drugs. The mutual prodrugs of the present invention may also exhibit aqueous/lipid solubility profiles different than those of each drug individually, which may further aid in improvements in formulation and/or delivery of the drugs.

The invention further provides a pharmaceutical composition that includes a compound having formula I. In one embodiment of the invention, a composition is provided that includes the compound having formula I, as described above, and a pharmaceutically acceptable carrier. The composition is preferably formulated for topical application.

In another aspect, the present invention provides a pharmaceutical composition that includes a therapeutically effective amount of a compound having formula II:

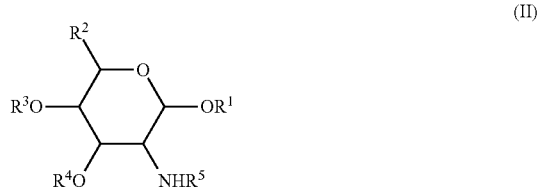

(II)

wherein $R^1$, $R^2$, $R^3$, $R^4$, and $R^5$ are each independently H or an organic group; and a pharmaceutically acceptable carrier; wherein the composition is formulated for topical application. In a preferred embodiment, $R^1$, $R^2$, $R^3$ and $R^4$ are each H and $R^5$ is an acetyl group. The compound of formula II is preferably glucosamine or a derivative or analog of glucosamine. While glucosamine and derivatives thereof are typically delivered orally, as, for example, nutraceuticals, and, less commonly, delivered subcutaneously, the present invention advantageously provides for the topical delivery of glucosamine and glucosamine derivatives, or their acetylated analogs.

Optionally, topical and/or transdermal application of a glucosamine, or a derivative or analog thereof, can be accompanied by co-administration of an anti-inflammatory agent, such as an NSAID. When administered together, the anti-inflammatory agent and the glucosamine, including derivatives and analogs thereof, may, but need not, be covalently linked to form a mutual prodrug, as described in greater detail herein.

In another aspect, the present invention provides a method for treating and/or preventing a disorder or a condition in a mammal that includes administering to the mammal a therapeutically effective amount of a composition of the invention. The method can involve a therapeutic, prophylactic and/or cosmetic use. In one embodiment, the invention is directed to a method to alleviate a condition treatable with glucosamine which method includes administering to a mammal, preferably a human, an effective amount of a compound having formula I or II as described herein. In another embodiment, the invention is directed to a method to alleviate a condition treatable with an anti-inflammatory agent which method includes administering to a mammal an effective amount of a compound having formula I or II as described herein.

BRIEF DESCRIPTION OF THE DRAWINGS

FIG. 2A shows a diagram of the structure of the prodrug sulphasalazine; FIG. 2B shows a diagram of the structure of projected mutual prodrug model 5-fluorouracil/cytarabine; FIG. 2C shows a diagram of the structure of projected mutual prodrug model ibuprofen/paracetamol; and FIG. 2D shows a diagram of the structure of projected mutual prodrug model ibuprofen/salicylamide.

FIG. 14 is a bar graph showing the accumulation of N-acetyl glucosamine through shed snake skin from phosphate buffer (pH 5.5) including 2%, 5%, 10%, 25%, and 50% ethanol, by percentage volume of aqueous phase and ethanol containing NAG.

DETAILED DESCRIPTION OF ILLUSTRATIVE EMBODIMENTS

Figure 1:
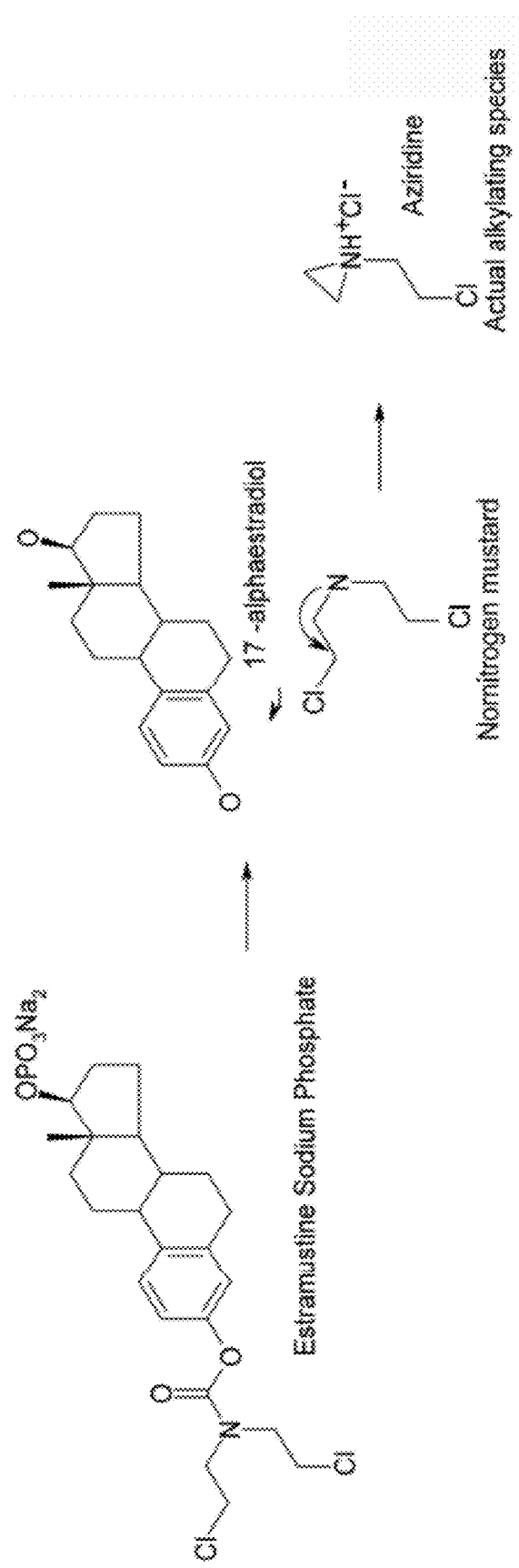
FIG. 1 is a diagram of the structure of estramustine sodium phosphate (EMCYT) and its promoieties.
Figure 2B:
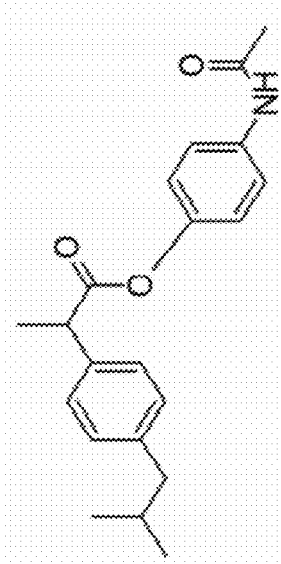
FIGS. 2A-2D show structures of certain prodrug models.
Figure 2C:
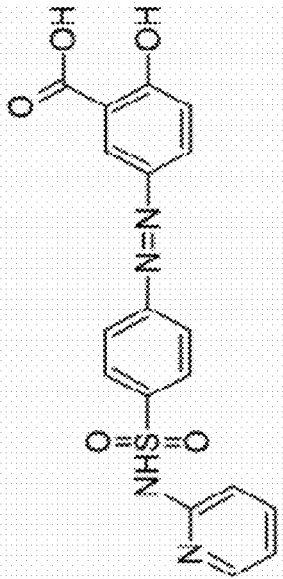
Figure 2A:
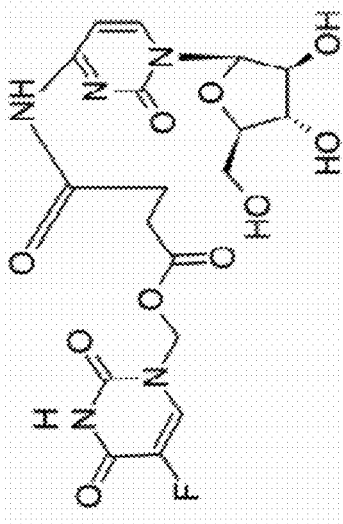
Figure 2D:
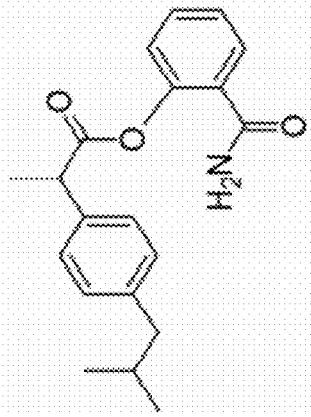

Mammals, both humans and animals, commonly suffer from certain diseases associated with the deterioration of cartilage and joint connective tissue, such as osteoarthritis, which can cause pain, swelling, stiffness, and limited mobility of the affected joint. Management of the symptoms has typically been carried out through treatment with anti-inflammatory agents, such as NSAIDs. Anti-inflammatory agents are well documented for their pharmacological, toxicological, and biopharmaceutical properties in the treatment of pain and inflammation associated with diseases such as osteoarthritis.

The administration of NSAIDs may, however, cause certain deleterious side effects in some patients. For example, NSAIDs may cause stomach upset, stomach ulcers and/or intestinal bleeding. Also, persons having certain conditions, such as thyroid disease, diabetes, heart disease, high blood pressure, and allergies, as well as persons who are about to have surgery (including dental surgery) and pregnant women may suffer serious side effects from administration of NSAIDs. Further, anti-inflammatory drugs do not treat an underlying cause of the disorder, e.g., deterioration of cartilage and connective tissues.

Glucosamine is currently being investigated as a possible treatment for diseases characterized by degeneration of e.g., cartilage and connective tissues. There is evidence that treatment with glucosamine not only eases the pain of, e.g., osteoarthritis, but it may also treat the disease itself, as it has been shown to slow the progression of degeneration and to re-grow cartilage tissue. Glucosamine is thus expected to be effective in the treatment of osteoarthritis, although it is currently not regulated in the United States as an active pharmaceutical ingredient (API).

Glucosamine is typically administered orally; however it is considered to have poor bioavailability as an orally administered nutraceutical. Only a small percentage of the active ingredient (e.g., 12-13%) is believed to be available to the affected tissue following oral administration.

Subcutaneous injection of a glucosamine has also been investigated. For example, SYNVISC, a device for administering a hyaluronic acid derivative available from Genzyme Corp. (Naarden, the Netherlands), is a therapy that is FDA approved only for the local treatment of pain associated with osteoarthritis of the knee. SYNVASC is often administered to patients "off-label," that is, it is administered to other (e.g., non-approved) joints, thus providing anecdotal evidence that glucosamine is effective as a treatment for osteoarthritis. Injection of a drug, however, carries its own potential problems, e.g., injection site infection, patient aversion to injection, difficulty of administration, etc. Thus, improved dosage forms, providing greater bioavailability of glucosamine, its derivatives and analogs, and more effective methods of its delivery to the affected areas of a patient are needed.

The present invention provides for effective delivery of glucosamine, including derivatives and analogs thereof, optionally delivered in the form of a mutual prodrug with an anti-inflammatory agent, to joints affected with diseases associated with degeneration of cartilage and connective tissue.

As used herein, the term "glucosamine" is understood to refer to glucosamine, derivatives of glucosamine, analogs of glucosamine, and metabolites of glucosamine, unless otherwise indicated.

As used herein, the term "organic group" is understood to mean a hydrocarbon group (with optional elements other than carbon and hydrogen, such as oxygen, nitrogen, sulfur, and silicon) that is classified as an aliphatic group, cyclic group, or combination of aliphatic and cyclic groups (e.g., alkaryl and aralkyl groups).

The term "aliphatic group" means a saturated or unsaturated linear or branched hydrocarbon group. This term is used to encompass alkyl, alkenyl, and alkynyl groups, for example. The term "alkyl group" means a saturated linear or branched hydrocarbon group including, for example, methyl, ethyl, isopropyl, t-butyl, heptyl, dodecyl, octadecyl, amyl, 2-ethylhexyl, and the like. The term "alkenyl group" means an unsaturated, linear or branched hydrocarbon group with one or more carbon-carbon double bonds, such as a vinyl group. The term "alkynyl group" means an unsaturated, linear or branched hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polynuclear aromatic hydrocarbon group. The term "heterocyclic group" means a closed ring hydrocarbon in which one or more of the atoms in the ring is an element other than carbon (e.g., nitrogen, oxygen, sulfur, etc.). A group that may be the same or different from another group is referred to as being "independently" something.

The present invention provides a novel compound that is a mutual prodrug combining a first component, glucosamine, or a derivative or analog of glucosamine, and a second component, an anti-inflammatory agent. The present invention further provides a pharmaceutical composition including the mutual prodrug compound to facilitate delivery of the active agents. Once the mutual prodrug delivered via the composition and is cleaved in vivo, the first component and the second component are rendered active and mutually provide the therapeutic benefits of NSAIDs and glucosamine and its analogs and derivatives, such as glycosaminoglycans. Pain may be managed, for example, via COX-1/COX-2 inhibition mechanisms of a non-steroidal anti-inflammatory agent delivered as a component of the mutual prodrug, with the added benefit that, as the anti-inflammatory is delivered topically, substantially all potential side effects, particularly gastrointestinal side effects, are reduced or eliminated. The maintenance and/or repair of tissues via regulation of cellular events and/or physiological processes, such as cell-cell and cell-matrix interactions, and cell proliferation/differentiation may be managed by, e.g., a glycosaminoglycan or ester of glycosaminoglycan as the other component of the mutual prodrug.

Additionally, while not wishing to be held to any particular theory, the anti-inflammatory component of the mutual prodrug may assist in the percutaneous delivery of the glucosamine, thus increasing the bioavailability of the glucosamine upon cleavage of the mutual prodrug in vivo. Additionally, the anti-inflammatory itself also provides treatment of the affected areas.

The mutual prodrug compound of the present invention is represented by formula I:

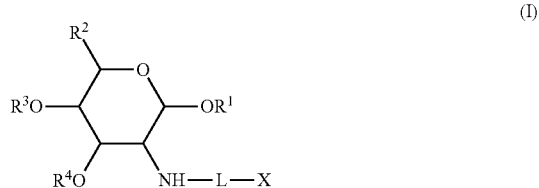

(I)

wherein $R^1$, $R^2$, $R^3$ and $R^4$ are each independently H or an organic group, as defined above, X is an anti-inflammatory agent, and L is an optional linking group. If no linking group, L, is present, the anti-inflammatory agent, X, is directly linked to the first component. Linking groups are of any type such that the first component (to the left of linker L in formula I) is covalently linked to the second component, X (to the right of linker L in formula I), and wherein the linking group is cleavable, either between the N(H)-L bond, the L-X bond, and/or internally within the linker L, in such a manner in vivo as to render the first component and the second component active. Typically the linking group is an organic group, as defined above. Preferred linking groups include an acyloxy ester and an alpha hydroxyl ester.

The first component of the mutual prodrug compound provides the glucosamine portion of the mutual prodrug. While any glucosamine of the structure indicated above is suitable for use in the mutual prodrug compounds of the present invention, certain glucosamines may provide preferred embodiments. Such glucosamines include, but are not limited to, for example, glucosamine, glucosamine pentaacetate, glucosamine-1-phosphate, glucosamine-6-phosphate, N-acetyl-β-D-glucosamine, N-acetylglucosamine-6-phosphate, N-acetyl-glucosamine-1-phosphate, uridine diphosphate-N-acetyl glucosamine, 2-amino-2-deoxy-1,3,4,6-acetyl-β-D-glucopyranose, the acetylated analog of 2-amino-2-deoxy-1,3,4,6-acetyl-β-D-glucopyranose, 2-acetamido-2-deoxy-β-D-glucopyranose-1,3,4,6-tetraacetate, the acetylated analog of 2-acetamido-2-deoxy-β-D-glucopyranose-1,3,4,6-tetraacetate, and N-acetyl-glucosamine (NAG). Particularly preferred embodiments of the mutual prodrug of the present invention include amino-2-deoxy-1,3,4,6-acetyl-β-D-glucopyranose, 2-acetamido-2-deoxy-β-D-glucopyranose-1,3,4,6-tetraacetate, and N-acetyl-glucosamine (NAG).

As indicated above, the mutual prodrugs of the present invention include as a second component an anti-inflammatory agent covalently attached to the glucosamine component, as described in more detail below.

The components of the mutual prodrug typically remain inactive until they are converted to their active forms in vivo by breaking the covalent bond between the components. The anti-inflammatory agent may be attached directly to the glucosamine (e.g., replacing one of the amino hydrogens), wherein upon cleavage in vivo, only the two active species of the mutual prodrug (the anti-inflammatory and the glucosamine) are provided. Alternatively, the anti-inflammatory agent may be covalently attached to the glucoamine via a linking group or spacer, L, for example, an ester group. Upon delivery of this embodiment of the mutual prodrug, the bonds between the first and/or second components and the linking group are cleaved, e.g., by esterases present in vivo, the mutual prodrug providing the two active species (the anti-inflammatory and the glucosamine). The linking groups, if present, are preferably selected such that the entire linking group is cleaved from the glucosamine and the anti-inflammatory, whereupon the linking group is released and optionally degraded or otherwise metabolized.

Any type of anti-inflammatory agent capable of covalently bonding to the glucosamine, as described above, and which provides desired effects to a patient are suitable for use in the mutual prodrugs of the present invention. Such anti-inflammatory agents include, for example, prostaglandins, arachidonic acid, metabolites of arachidonic acid, non-steroidal anti-inflammatory agents and derivatives of non-steroidal anti-inflammatory agents.

Figure 3A:
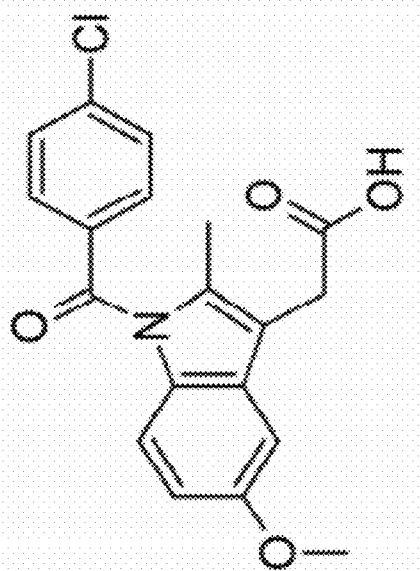
FIGS. 3A and 3B show structures of indomethacin and glucamethacin, respectively.
Figure 3B:
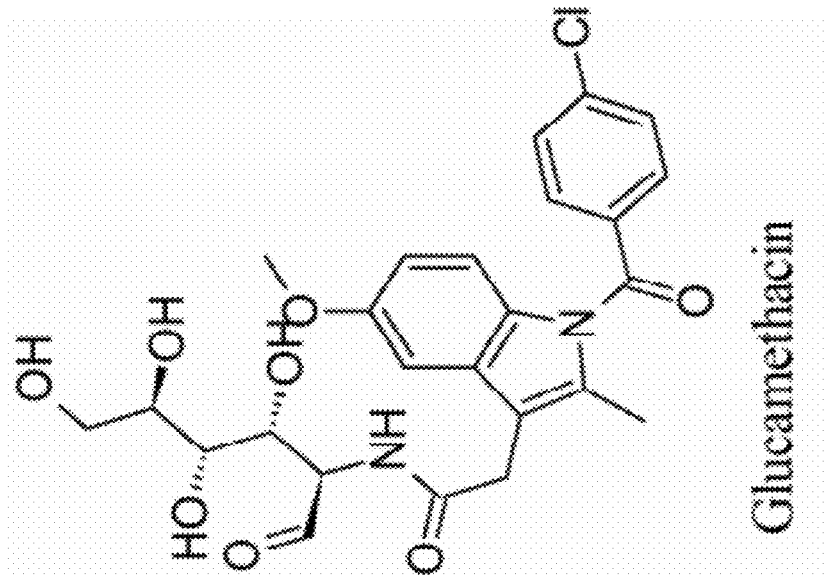

Non-steroidal anti-inflammatory agents (NSAIDs) are particularly useful in view of their wide availability, their effectiveness as an anti-inflammatory, and, for some NSAIDs, their relatively low cost. Preferred NSAIDs useful in the mutual prodrug compounds of the present invention include, but are not limited to, for example, salicylic acids (e.g., acetylsalicylic acid (aspirin), choline magnesium trisalicylate, diflunisal, salsalate, magnesium salicylate, choline salicylate, choline magnesium salicylate, sodium salicylate), propionic acids (e.g., fenoprofen, fenoprofen calcium, flurbiprofen, ibuprofen, ketoprofen, naproxen, oxaprozin, pirprofen, indobufen, indoprofen, tiaprofenic acid), acetic acids (e.g., diclofenac, indomethacin, glucametacin, sulindac, tolmetin, carprofen) enolic acids (e.g., meloxicam, piroxicam, tenoxicam, lomoxicam) fenamic acids (e.g., meclofenamate, meclofenamate sodium, mefenamic acid, etofenamat), napthylalkanones (e.g., nabumetone), pyranocarboxylic acids (e.g., etodolac), pyrroles (e.g., ketorolac, ketorolac tromethamine, phenylbutazone, remifenzone), para-aminphenols (e.g., acetaminophen), and cyclooxygenase-2 (COX-2) inhibitors (e.g., celecoxib, valdecoxib, rofecoxib, flosulide, nimesulide). The structures of indomethacin and glucametacin are shown in FIGS. 3A and 3B respectively. Preferred NSAIDs for use in the mutual prodrug of the present invention include ibuprofen and ketoprofen. In one embodiment, the compound indomethacin is excluded from the group of NSAIDs used in the mutual prodrug of the invention.

The invention additionally provides pharmaceutical compositions. The compositions of the present invention may include the mutual prodrug compound of formula I as described above in a pharmaceutically acceptable carrier, as described in more detail below.

The invention also provides a composition that includes a glucosamine, or a derivative or analog of glucosamine (e.g., a compound having formula II), in a formulation for topical and/or transdermal delivery. These topical glucosamine compositions are believed to provide percutaneous transport/permeability across skin membrane such that bioavailability of glucosamine, and consequently its effectiveness, as compared with the glucosamine bioavailability of oral glucosamine formulations, may be improved.

Additional compositions of the present invention may include a glucosamine (e.g., the compound of formula I) in a pharmaceutically acceptable carrier, wherein the composition is, preferably, formulated for topical and/or transdermal delivery. These compositions do not include the mutual prodrug; however, formulations as disclosed herein have been shown to provide unexpected percutaneous transport across skin membrane, which, it is anticipated, may increase the bioavailability of the glucosamine.

As used herein and unless otherwise indicated, topical administration is functionally the same as transdermal administration. While not wishing to be held to any particular theory, topical administration of glucosamine may provide a greater bioavailability of the active ingredient. Up to the present, however, it has proven difficult to achieve permeation across skin membranes of glucosamines. The present invention provides pharmaceutical compositions including glucosamines that have improved permeability, thus providing a greater bioavailability of the active agent.

Certain useful compositions of the invention include, but are not limited to, e.g., esters of glycosaminoglycans, such as chrondroitin, dermatan, heparin, heparin, keratin, and other biologically significant proteoglycans. Examples of certain useful glycosaminoglycan esters, which are components of connective tissue and cartilage, include 2-amino-1,3,4,6-acetyl-beta-D-glucopyranosyl; 2-acetamido-2-deoxy-beta-D-glucopyranose-1,3,4,6-tetraacetate; and 2-acetamido-2-deoxy-beta-D-glucopyranose.

Compositions of the present invention including one or more glucosamines are provided by, for example, formulating or admixing the glucosamine(s) in a pharmaceutically acceptable carrier, for example a cream, gel, solution, ointment, lotion, suspension, emulsion, micoremulsion, liposome, transdermal patch, etc. Such cream, gel, solution, ointment, lotion, suspension, emulsion, mocroemulsion, liposome, or transdermal patch may include any number or combination of topical/transdermal vehicles approved by the United States Pharmacopoeia (USP) for human or veterinary use, for example, fatty esters, alcohols, gel bases (e.g., pluronic gels) lecithin, dimethylsulfoxide (DMSO), water, etc. to form a transdermal and/or topical agent. If either a subcutaneous or an oral formulation is desired, the pharmaceutically acceptable carrier may include, for example, normal saline, pluronic F-127 solution, or a generally recognized as safe (GRAS) delivery solution (subcutaneous, intramuscular, and/or intravenous delivery), or tablets, capsules, powders, suspensions, emulsions, and/or gels (oral delivery).

The pharmaceutical compositions of the present invention may include one or more additional components appropriate for use in the composition and that, when included, will provide the desired results (e.g., will provide additional therapeutic benefits to skin or tissues, or will aid, for example, in the consistency and stability of the composition). Additional components may include, for example, antimicrobial agents, gelling agents, emulsifying agents, stiffening agents, skin healing agents, emollients surfactants, solvents, lubricants, waxes, humectants, skin penetration enhancers, anti-oxidants, and any combination of these.

While it is understood that certain components useful in the compositions of the present invention may provide more than one effect in a composition depending upon, e.g., concentration of the component (for example, a poloxamer may be considered both a gelling agent and an emulsifier), the following are typical additional components useful in the present compositions.

Anti-microbial agents are typically present in a composition to assist in preserving the composition, thus extending its shelf life. Anti-microbial agents useful in the present invention include ethanol, parabens, salts of parabens, sorbic acid, potassium sorbate, propylene glycol, glycerin, etc. Combinations of these anti-microbial agents may also be used.

Certain additional components may be useful in enhancing penetration of the composition through the skin membranes. Useful skin penetration enhancers include, for example, dimethyl sulfoxide, ethanol, polyethylene glycol, urea, dimethyl acetamide, sodium lauryl sulfate, Spans, Tweens, terpenes, azone, acetone, and oleic acid. A preferred skin penetration enhancer, particularly for e.g., veterinary use, is dimethyl sulfoxide (DMSO). A preferred skin penetration enhancer, particularly for use in administration to human patients, is ethanol.

While the present compositions may themselves provide treatment to skin for such conditions as skin damage, burns, and age-related wrinking of the skin, in addition to providing therapeutic effects to such diseases as osteoarthritis, it may be desired to include additional skin healing and/or anti-oxidant providing components for additional therapeutic benefit to the skin. Such skin healing agents include, for example, vitamin E, vitamin E-tocopherol polyethylene glycol succinate (vitamin E-TPGS), ascorbic acid, alpha tocopherol, beta tocopherol, gamma tocopherol, aloe vera, etc. A particularly useful skin healing agent in the present compositions is vitamin E. Additionally, certain useful anti-oxidants include fumaric acid, malic acid, ascorbic acid palmitate, butylated hydroxylanisole, propyl gallate, sodium ascorbate, sodium metabisulfite, etc.

Certain other additional components, such as emulsifying agents and stiffening agents, may be used to provide, e.g., stability and desired consistency to the compositions. Typical emulsifying agents useful in the present invention include cholesterol, poloxamers, lecithin, carbomers, polyoxyethylene ethers, fatty acid esters, stearates, etc. Certain preferred emulsifying agents include poloxamers and lecithin, with a particularly preferred poloxamer being Pluronic F-127. Additionally, typical stiffening agents useful in the present compositions include long chain fatty alcohols and long chain fatty alcohol esters.

In addition to any of the above additional components, one or more of the anti-inflammatory agents discussed above in connection with the mutual prodrug of the present invention may be included as a free component (e.g., not covalently bonded to the glucosamine or in addition to a composition including the mutual prodrug) in any of the compositions of the present invention. Furthermore, as these anti-inflammatory agents are not covalently linked to the glucosamine, choice of anti-inflammatory present as a free agent is not thusly limited.

To provide pharmaceutically effective compositions, the first component of the compositions of the present invention (e.g., the glucosamine, derivatives thereof and/or analogs thereof) are typically present in the composition in an amount of at least about 1 percent by weight, and preferably at least about 10 percent by weight. Further, the glucosamine component is typically present in the compositions in an amount of no greater than about 75 percent by weight, and preferably no greater than about 40 percent by weight.

Figure 4:
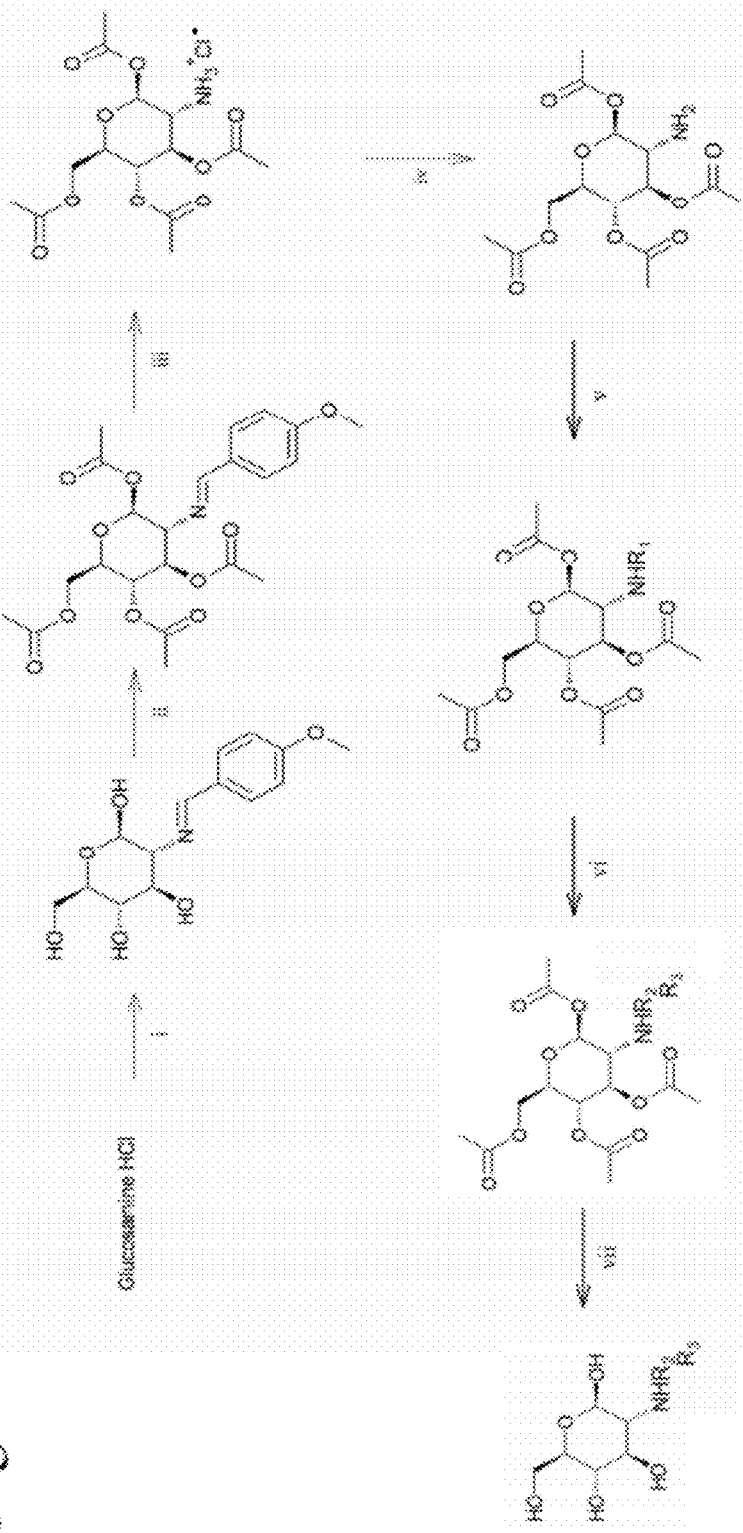
FIG. 4 shows an exemplary scheme for synthesis of a spacer linked mutual prodrug of the invention.
Figure 5:
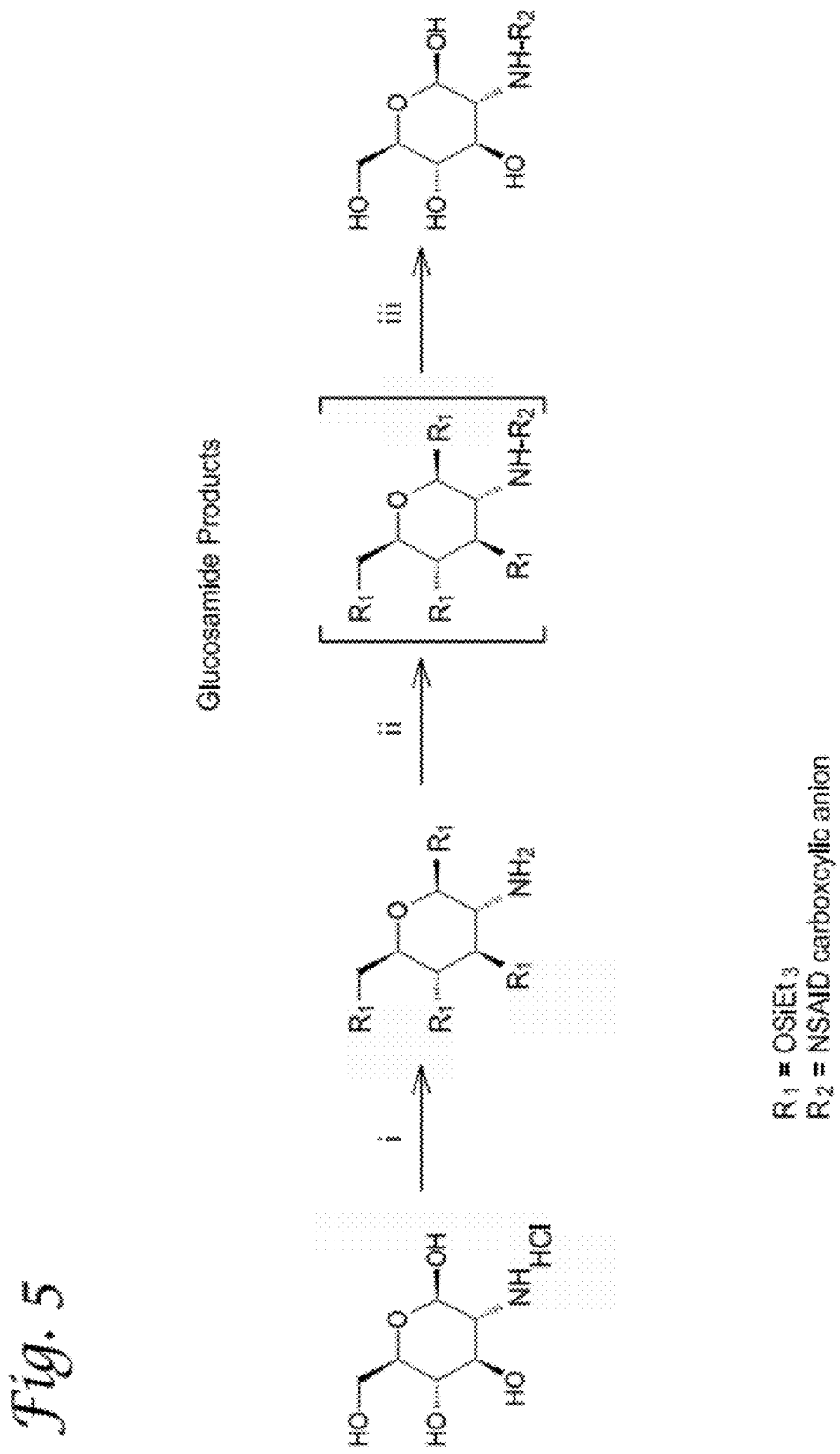
FIG. 5 shows a scheme for synthesis of a directly linked mutual prodrug of the invention.

Two general methods for synthesizing mutual prodrugs of the invention are shown in FIGS. 4 and 5. It should be understood, however, that the invention is not limited by any particular synthetic method, and other methods of synthesis are included. Each exemplary method (FIGS. 4 and 5) provides a mutual prodrug that is a glucosamine or derivative thereof, such as a glycosaminoglycan or ester of glycosaminoglycan, coupled with an anti-inflammatory agent, such as an NSAID, and the exemplary mutual prodrug is hydrolysable or otherwise cleavable. Preferably, the linkage is hydrolysable or cleavable in vivo.

Scheme 1 (FIG. 4) is a diagram describing the general synthesis of an exemplary mutual prodrug of the present invention wherein the glucosamine is linked with the anti-inflammatory agent via a spacer (e.g., a linker or linking group), such as an imide-ester covalent bound alkyl chain, covalently bound to the NSAID via the inherently created malonic ester configuration. The linking moieties are typically cleaved in vivo to release the glucosamine and the anti-inflammatory agent, as well as the inert linking group.

Alternatively, mutual prodrugs of the present invention may be synthesized to provide a direct link between the glucosamine, or derivative thereof, and the anti-inflammatory agent according to the exemplary scheme of FIG. 5. Compositions including mutual prodrugs synthesized according to the general scheme of FIG. 5 deliver mutual prodrugs that are preferably cleaved in vivo to provide the glucosamine and the to anti-inflammatory without release of an inert component.

The present invention also provides methods of treating a disorder in a mammal that includes administration of the compositions of the present invention.

The compounds, compositions, and methods of the present invention are suitable for treating various disorders or conditions in mammals (e.g., for human and/or veterinary administration), wherein treatment includes relief from a symptom of the disorder (e.g., pain and/or swelling of a joint), alleviating a cause of the disorder (e.g., repair of deteriorating cartilage and/or connective tissues) and/or improvement of a condition (e.g, lessening of the appearance of facial wrinkides).

The disorder may be the result of disease (e.g., osteoarthritis) or may be the result of a physical injury (e.g., joint and muscle sprains). Furthermore, the compositions and methods of the present invention are not necessarily limited to treatment of disease and/or injury. Compositions of the present invention may provide therapeutic and cosmetic effects to damaged and wrinkled skin by e.g., application of the compositions to facial wrinkles and/or other areas of skin damage (e.g., skin damage caused by sun, salt, and/or wind exposure), to provide soothing of the skin (a therapeutic effect) and at least temporary lessening of the appearance of wrinkles in the skin (a cosmetic effect).

Thus, disorders and conditions that may be treated according to the methods of the present invention, as discussed herein, include, but are not limited to, arthritis, osteoarthritis, osteoporosis, muscle sprains, muscle strains, joint sprains, joint strains, tendonitis, bursitis, burns, joint pain, inflamed joints, skin damage, skin tenderness, skin pain, sun-damaged skin, wind-damaged skin, salt-damaged skin, scar tissue, age-related wrinkling of the skin, and any combinations thereof.

Methods of treatment according to the present invention include administration of a pharmaceutical composition of the invention to a patient using any convenient route, without limitation. In a preferred embodiment, the mutual prodrug is administered to a patient topically and/or transdermally, via local application to skin or to other external or internal membrane, as described more fully above. In other formulations, the mutual prodrug, or its metabolic products, are delivered to the bloodstream and circulated systemically.

In another embodiment of the invention, the mutual prodrug is administered orally, such as in the form of tablets, powders, capsules, suspensions, emulsions, gels, etc. In further embodiments, treatment of a disorder is achieved via subcutaneous, intramuscular, and intravenous injection, as more fully described above.

While it is understood that the compositions of the present invention may be administered to a patient to treat a number of disorders and/or conditions, which can include, without limitation, therapeutic disorders and/or cosmetic applications, it is also contemplated that many different additional components can be included to provide formulations suitable for delivery of a composition of the invention with respect to the disorder or condition of interest.

For example, compositions of the present invention that include a glucosamine, derivative thereof, or analog thereof (e.g., the compositions that do not include the mutual prodrug) may be prepared from various combinations of additional components, e.g., isopropyl palmitate, isopropyl myristate, a glycosaminoglycan or glycosaminoglycan ester, a stiffening agent like long chain fatty alcohols, long chain fatty alcohol esters, waxes like spermaceti, nonionic gelling/emulsifiers like poloxamers, water, and a USP approved antimicrobial agent, wherein the additional components are selected to provide desired characteristics to the compositions. Further, certain of these exemplary formulations may provide enhanced permeability, thus improved bioavailablilty, of the glycosaminoglycan ester.

Exemplary formulations include, but are not limited to, the following, wherein an NSAID may, optionally, be included in any of the formulations:

1. Isopropyl palmitate, DMSO, ethanol, lecithin, poloxamer, ester of glycosaminoglycan
2. Isopropyl palmitate, water, ethanol, lecithin, poloxamer, ester of glycosaminoglycan
3. Isopropyl palmitate, vitamin E, lecithin, poloxamer, ester of glycosaminoglycan
4. Isopropyl myristate, poloxamer, water, ethanol, lecithin, ester of glycosaminoglycan
5. Isopropyl myristate, water, lecithin, poloxamer, ester of glycosaminoglycan
6. Isopropyl palmitate, water, lecithin, poloxamer, USP approved antimicrobial agent, ester of glycosaminoglycan
7. Vitamin E, lecithin, isopropyl myristate, ester of glycosaminoglycan
8. Isopropyl myristate, lecithin, poloxamer, ester of glycosaminoglycan
9. Isopropyl palmitate, USP approved antimicrobial agent, vitamin E, lecithin, hydrous or anhydrous lanolin, ester of glycosaminoglycan
10. Isopropyl palmitate, USP approved antimicrobial agent, vitamin E, hydrous or anhydrous lanolin, ester of glycosaminoglycan
11. Isopropyl palmitate, USP approved antimicrobial agent, vitamin E, lecithin, ester of glycosaminoglycan
12. Isopropyl palmitate, lecithin, USP approved antimicrobial agent, hydrous or anhydrous lanolin, ester of glycosaminoglycan
13. Isopropyl myristate, vitamin E, USP approved antimicrobial agent, lecithin, hydrous or anhydrous lanolin, ester of glycosaminoglycan
14. Isopropyl myristate, USP approved antimicrobial agent, vitamin E, lecithin, ester of glycosaminoglycan
15. Isopropyl myristate, USP approved antimicrobial agent, vitamin E, hydrous or anhydrous lanolin, ester of glycosaminoglycan
16. Isopropyl myristate, USP approved antimicrobial agent, lecithin, hydrous or anhydrous lanolin, ester of glycosaminoglycan
17. Isopropyl myristate, USP approved antimicrobial agent, vitamin E, ester of glycosaminoglycan
18. Isopropyl myristate, USP approved antimicrobial agent, lecithin, ester of glycosaminoglycan
19. Isopropyl myristate, USP approved antimicrobial agent, hydrous or anhydrous lanolin, ester of glycosaminoglycan
20. Isopropyl myristate, DMSO, ethanol, lecithin, poloxamer, ester of glycosaminoglycan
21. Isopropyl myristate, vitamin E, Lecithin, hydrous or anhydrous lanolin, ester of glycosaminoglycan 22. Isopropyl myristate, DMSO, ethanol, vitamin E, poloxamer, ester of glycosaminoglycan
23. Isopropyl myristate, DMSO, vitamin E, poloxamer, ester of glycosaminoglycan
24. Isopropyl myristate, DMSO, ethanol, vitamin E, poloxamer, ester of glycosaminoglycan
25. Isopropyl palmitate, DMSO, ethanol, lecithin, vitamin E, poloxamer, ester of glycosaminoglycan
26. Isopropyl palmitate, ethanol, lecithin, poloxamer, ester of glycosaminoglycan
27. Isopropyl palmitate, DMSO, ethanol, lecithin, ester of glycosaminoglycan
28. Isopropyl palmitate, DMSO, ethanol, poloxamer, ester of glycosaminoglycan
29. Isopropyl palmitate, ethanol, lecithin, ester of glycosaminoglycan
30. Isopropyl palmitate, DMSO, ethanol, lecithin, vitamin E, poloxamer, ester of glycosaminoglycan
31. Isopropyl palmitate, isopropyl myristate, DMSO, ethanol, lecithin, poloxamer, ester of glycosaminoglycan
32. Isopropyl palmitate, isopropyl myristate, DMSO, ethanol, lecithin, vitamin E, poloxamer, ester of glycosaminoglycan
33. Isopropyl palmitate, isopropyl myristate, DMSO, ethanol, poloxamer, ester of glycosaminoglycan
34. Isopropyl palmitate, isopropyl myristate, DMSO, ethanol, vitamin E, poloxamer, ester of glycosaminoglycan
35. Isopropyl palmitate, isopropyl myristate, DMSO, ethanol, lecithin, ester of glycosaminoglycan
36. Isopropyl palmitate, isopropyl myristate, DMSO, ethanol, lecithin, vitamin E, poloxamer, ester of glycosaminoglycan
37. Isopropyl palmitate, isopropyl myristate, DMSO, lecithin, vitamin E, poloxamer, ester of glycosaminoglycan
38. Isopropyl palmitate, isopropyl myristate, DMSO, vitamin E, poloxamer, ester of glycosaminoglycan
39. Isopropyl palmitate, isopropyl myristate, DMSO, lecithin, poloxamer, ester of glycosaminoglycan
40. Isopropyl palmitate, isopropyl myristate, DMSO, lecithin, vitamin E, ester of glycosaminoglycan
41. Isopropyl palmitate, isopropyl myristate, DMSO, poloxamer, ester of glycosaminoglycan
42. Isopropyl palmitate, isopropyl myristate, DMSO, lecithin, ester of glycosaminoglycan
43. Isopropyl palmitate, isopropyl myristate, DMSO, vitamin E, ester of glycosaminoglycan
44. Isopropyl palmitate, isopropyl myristate, water, ethanol, lecithin, ester of glycosaminoglycan
45. Isopropyl palmitate, isopropyl myristate, water, ethanol, vitamin E, poloxamer, ester of glycosaminoglycan
46. Isopropyl palmitate, isopropyl myristate, water, ethanol, vitamin E, poloxamer, hydrous or anhydrous lanolin, ester of glycosaminoglycan
47. Isopropyl palmitate, isopropyl myristate, water, ethanol, poloxamer, hydrous or anhydrous lanolin, ester of glycosaminoglycan
48. Isopropyl palmitate, isopropyl myristate, water, ethanol, vitamin E, hydrous or anhydrous lanolin, ester of glycosaminoglycan
49. Isopropyl palmitate, isopropyl myristate, water, ethanol, vitamin E, poloxamer, hydrous or anhydrous lanolin, ester of glycosaminoglycan
50. Isopropyl palmitate, isopropyl myristate, water, ethanol, lecithin, hydrous or anhydrous lanolin, ester of glycosaminoglycan
51. Isopropyl palmitate, isopropyl myristate, water, ethanol, vitamin E, hydrous or anhydrous lanolin, ester of glycosaminoglycan
52. Isopropyl palpitate, isopropyl myristate, water, ethanol, poloxamer, hydrous or anhydrous lanolin, ester of glycosaminoglycan
53. Isopropyl palmitate, isopropyl myristate, water, ethanol, hydrous or anhydrous lanolin, ester of glycosaminoglycan
54. Isopropyl palmitate, isopropyl myristate, water, ethanol, poloxamer, ester of glycosaminoglycan
55. Isopropyl palmitate, isopropyl myristate, water, ethanol, ester of glycosaminoglycan
56. Isopropyl palmitate, isopropyl myristate, water, USP approved antimicrobial agent, lecithin, vitamin E, poloxamer, ester of glycosaminoglycan
57. Isopropyl palmitate, isopropyl myristate, water, USP approved antimicrobial agent, vitamin E, poloxamer, ester of glycosaminoglycan
58. Isopropyl palmitate, isopropyl myristate, water, USP approved antimicrobial agent, lecithin, poloxamer, ester of glycosaminoglycan
59. Isopropyl palmitate, isopropyl myristate, water, USP approved antimicrobial agent, lecithin, vitamin E, ester of glycosaminoglycan
60. Isopropyl palmitate, isopropyl myristate, water, USP approved antimicrobial agent, lecithin, ester of glycosaminoglycan
61. Isopropyl palmitate, isopropyl myristate, water, USP approved antimicrobial agent, poloxamer, ester of glycosaminoglycan
62. Isopropyl palmitate, isopropyl myristate, water, USP approved antimicrobial agent, vitamin E, ester of glycosaminoglycan
63. Isopropyl palmitate, isopropyl myristate, water, ethanol, lecithin, vitamin E, poloxamer, ester of glycosaminoglycan
64. Isopropyl palmitate, isopropyl myristate, ethanol, lecithin, poloxamer, ester of glycosaminoglycan
65. Isopropyl palmitate, isopropyl myristate, DMSO, ethanol, lecithin, ester of glycosaminoglycan
66. Isopropyl palmitate, isopropyl myristate, ethanol, lecithin, vitamin E, poloxamer, ester of glycosaminoglycan
67. Isopropyl palmitate, isopropyl myristate, water, ethanol, lecithin, poloxamer, ester of glycosaminoglycan
68. Isopropyl palmitate, isopropyl myristate, water, USP approved antimicrobial agent, lecithin, poloxamer, ester of glycosaminoglycan
69. Isopropyl palmitate, isopropyl myristate, DMSO, ethanol. poloxamer, ester of glycosaminoglycan
70. Isopropyl palmitate, isopropyl myristate, ethanol, lecithin, ester of glycosaminoglycan
71. Isopropyl palmitate, isopropyl myristate, USP approved antimicrobial agent, vitamin E, lecithin, hydrous or anhydrous lanolin, ester of glycosaminoglycan
72. Isopropyl palmitate, isopropyl myristate, USP approved antimicrobial agent, lecithin, hydrous or anhydrous lanolin, ester of glycosaminoglycan
73. Isopropyl palmitate, isopropyl myristate, USP approved antimicrobial agent, vitamin E, hydrous or anhydrous lanolin, ester of glycosaminoglycan
74. Isopropyl palmitate, isopropyl myristate, USP approved antimicrobial agent, vitamin E, lecithin, ester of glycosaminoglycan
75. Isopropyl palmitate, isopropyl myristate, USP approved antimicrobial agent, vitamin E, ester of glycosaminoglycan
76. Isopropyl palmitate, isopropyl myristate, USP approved antimicrobial agent, lecithin, ester of glycosaminoglycan 77. Isopropyl palmitate, isopropyl myristate, USP approved antimicrobial agent, hydrous or anhydrous lanolin, ester of glycosaminoglycan
78. Isopropyl palmitate, isopropyl myristate, USP approved antimicrobial agent, vitamin E, lecithin, hydrous or anhydrous lanolin, poloxamer, ester of glycosaminoglycan
79. Isopropyl palmitate, isopropyl myristate, USP approved antimicrobial agent, lecithin, hydrous or anhydrous lanolin, poloxamer, ester of glycosaminoglycan
80. Isopropyl palmitate, isopropyl myristate, USP approved antimicrobial agent, vitamin E, hydrous or anhydrous lanolin, poloxamer, ester of glycosaminoglycan
81. Isopropyl palmitate, isopropyl myristate, USP approved antimicrobial agent, vitamin E, lecithin, poloxamer, ester of glycosaminoglycan
82. Isopropyl palmitate, isopropyl myristate, USP approved antimicrobial agent, hydrous or anhydrous lanolin, poloxamer, ester of glycosaminoglycan
83. Isopropyl palmitate, isopropyl myristate, USP approved antimicrobial agent, lecithin, poloxamer, ester of glycosaminoglycan
84. Isopropyl palmitate, isopropyl myristate, USP approved antimicrobial agent, vitamin E, poloxamer, ester of glycosaminoglycan
85. Isopropyl palmitate, isopropyl myristate, USP approved antimicrobial agent, poloxamer, ester of glycosaminoglycan
86. Isopropyl palmitate, isopropyl myristate, water, USP approved antimicrobial agent, poloxamer, hydrous or anhydrous lanolin, ester of glycosaminoglycan
87. Isopropyl palmitate, isopropyl myristate, DMSO, vitamin E, lecithin, hydrous or anhydrous lanolin, poloxamer, ester of glycosaminoglycan
88. Isopropyl palmitate, isopropyl myristate, DMSO, lecithin, hydrous or anhydrous lanolin, poloxamer, ester of glycosaminoglycan
89. Isopropyl palmitate, isopropyl myristate, DMSO, vitamin E, hydrous or anhydrous lanolin, poloxamer, ester of glycosaminoglycan
90. Isopropyl palmitate, isopropyl myristate, DMSO, vitamin E, lecithin, hydrous or anhydrous lanolin, ester of glycosaminoglycan
91. Isopropyl palmitate, isopropyl myristate, DMSO, vitamin E, hydrous or anhydrous lanolin, ester of glycosaminoglycan
92. Isopropyl palmitate, isopropyl myristate, DMSO, lecithin, hydrous or anhydrous lanolin, ester of glycosaminoglycan
93. Isopropyl myristate, oleic acid, ethanol, lecithin, hydrous or anhydrous lanolin, ester of glycosaminoglycan
94. Isopropyl myristate, oleic acid, lecithin, hydrous or anhydrous lanolin, ester of glycosaminoglycan
95. Isopropyl myristate, lecithin, hydrous or anhydrous lanolin, ester of glycosaminoglycan
96. Isopropyl myristate, oleic acid, ethanol, DMSO, vitamin E, lecithin, hydrous or anhydrous lanolin, poloxamer, ester of glycosaminoglycan
97. Isopropyl myristate, oleic acid, DMSO, vitamin E, lecithin, hydrous or anhydrous lanolin, poloxamer, ester of glycosaminoglycan
98. Isopropyl myristate, oleic acid, ethanol, hydrous or anhydrous lanolin, ester of glycosaminoglycan
99. Isopropyl myristate, oleic acid, hydrous or anhydrous lanolin, ester of glycosaminoglycan
100. Isopropyl myristate, oleic acid, ethanol, vitamin E, poloxamer, ester of glycosaminoglycan
101. Fatty esters, ester of glycosaminoglycan
102. Isopropyl palmitate, isopropyl myristate, glycosaminoglycan or glycosaminoglycan ester, cetyl alcohol, poloxamer, water, antimicrobial agent
103. Isopropyl palmitate, isopropyl myristate, glycosaminoglycan or glycosaminoglycan ester, cetyl alcohol, antimicrobial agent
104. Isopropyl palmitate, isopropyl myristate, glycosaminoglycan or glycosaminoglycan ester, stearyl alcohol, poloxamer, water, antimicrobial agent
105. Isopropyl pahnitate, isopropyl myristate, glycosaminoglycan or glycosaminoglycan ester, stearyl alcohol, antimicrobial agent
106. Isopropyl palmitate, isopropyl myristate, glycosaminoglycan or glycosaminoglycan ester, cetostearyl alcohol, poloxamer, water, antimicrobial agent
107. Isopropyl palmitate, isopropyl myristate, glycosaminoglycan or glycosaminoglycan ester, cetostearyl alcohol, antimicrobial agent
108. Isopropyl palmitate, isopropyl myristate, glycosaminoglycan or glycosaminoglycan ester, spermaceti (or spermaceti replacement), poloxamer, water, antimicrobial agent
109. Isopropyl palmitate, isopropyl myristate, glycosaminoglycan or glycosaminoglycan ester, spermaceti (or spermaceti replacement), antimicrobial agent
110. Isopropyl palmitate, isopropyl myristate, glycosaminoglycan or glycosaminoglycan ester, cetyl esters, poloxamer, water, antimicrobial agent
111. Isopropyl palmitate, isopropyl myristate, glycosaminoglycan or glycosaminoglycan ester, cetyl esters, antimicrobial agent
112. Isopropyl palmitate, isopropyl myristate, glycosaminoglycan or glycosaminoglycan ester, emulsifying wax, poloxamer, water, antimicrobial agent
113. Isopropyl palmitate, isopropyl myristate, glycosaminoglycan or glycosaminoglycan ester, emulsifying wax, antimicrobial agent Certain of the above formulations of the invention will naturally be better suited for certain purposes. For example, one formulation to enhance percutaneous absorption of the composition at a joint, such as the knee, will likely be different from a formulation intended to heal/restore sun damaged skin around the eyes and/or wrinkles around the eyes caused by exposure to sun and weather. The latter use benefits from the inclusion of vitamin E to promote skin healing. However, vitamin E may not provide any added benefit to a formulation intended for penetration of the skin and into the joint, even though vitamin E would not interfere with the skin penetration process.

Thus cosmetic formulations, for example, are exemplified by formulation entries 1-101, while formulations suited for use in treating arthritic and/or inflamed joints are exemplified, for example, by formulation entries 102-113. It should be understood that, regardless of the intended use of the composition, the compositions and methods of the present invention are not limited by the selection of the components in the listed formulations 1-113.

EXAMPLES

The present invention is illustrated by the following examples which are directed to the mutual prodrugs and to the topical and/or transdermal application of glucosamines, including derivatives and esters thereof, as described above. It is to be understood that the particular examples, materials, amounts, and procedures set forth below are to be interpreted broadly in accordance with the scope and spirit of the invention as set forth herein. Further, the examples are provided for clarity of understanding, and the invention is not limited to the exact details as shown and described; many variations will be apparent to one skilled in the art.

Example 1

NSAID-Glucosamide Mutual Prodrug Development and Synthesis

Combining NSAIDs and glucosamine into a single mutual prodrug allows delivery of these drugs concomitantly in a form that can target disorders such as osteoarthritis by either oral or transdermal administration. Transdermal delivery is advantageous because it avoids side effects associated with oral delivery of NSAIDs, such as adverse drug reactions and/or adverse gastrointestinal effects, often experienced with oral administration to patients of NSAIDs (Shi et al., Acta Pharmacol. Sin., 25(3), 357-365 (2004); Benini et al., Pediatr. Nephrol., 19(2):232-234 (2004); Wibolm, Curr. Med. Res. Opin., 17(3):210-216 (2001); Kromann-Andersen et al., Dan. Med. Bull., 35(2):187-192 (1988); Pietzsch et al., Int. J. Clin. Pharmacol. Ther., 40(3):111-115 (2002); Karch et al., JAMA, 22, 234(12):1236-1241 (1975)) and also the metabolism/excretion events often observed with administration of glucosamine (Setnikar et al., Arzneimittel-Forschung, 36(4): 729-735 (1986); Aghazadeh-Habashi et al., Journal of Pharmacy & Pharmaceutical Sci., 5(2):181-184 (2000); Setnikar et al, Arzneimittel-Forschung, 43(10):1109-13 (1993); and Setnikar et al., Arzneimittel-Forschung, 51(9):699-725 (2001)).

Experimental

An objective of the present study was to synthesize directly-linked and chained-linked NSAID-glucosamidemutual prodrug models.

Materials and Methods

All reagents and solvents utilized were purchased from Fisher Scientific. TLC and preparative TLC chromatographs were performed on Analtech Co. UNIPLATES. Melting points were determined on a Fisher-Johns apparatus and are uncorrected. Nuclear magnetic resonance spectra were recorded on Varian INOVA 500 MHz spectrometer for $^1$H NMR and $^{13}$C NMR with tetramethysilane as an internal stand. Chemical shifts ($\delta$) are reported in parts per million (ppm) and signals are reported as s (singlet), d (doublet), t (triplet), m (multiplet), or br (broad singlet). A Beckman DU-650 and a Thermo Electron Corp. AQUAMATE were used to record the UV spectra. Staff at the University of Georgia's Chemical and Biological Sciences Mass Spectrometry Facility completed ESI (electrospray ionization) mass spectra. Column chromatographs were performed using silica gel >440 mesh. Differential Scanning calorimetry (DSC) was performed on a Perkin-Elmer DSC 7 with TAC 7/DX utilizing PYRIS Thermal Analysis System (Rev. E/March 2002) software.

Synthesis

Figure 6:
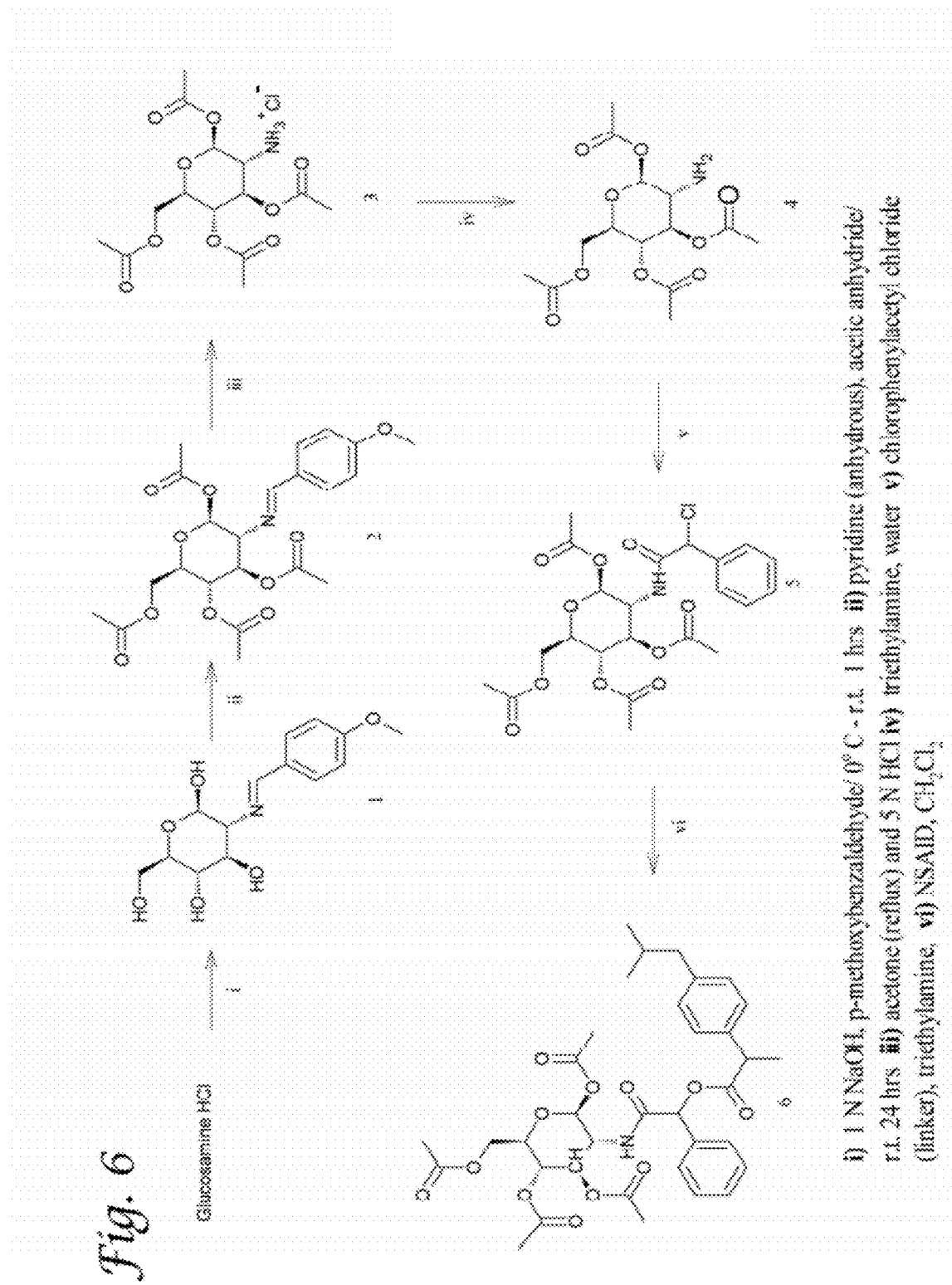
FIG. 6 shows a scheme for synthesis of a spacer linked mutual prodrug that includes a glycosaminoglycan and an NSAID.
Figure 7:
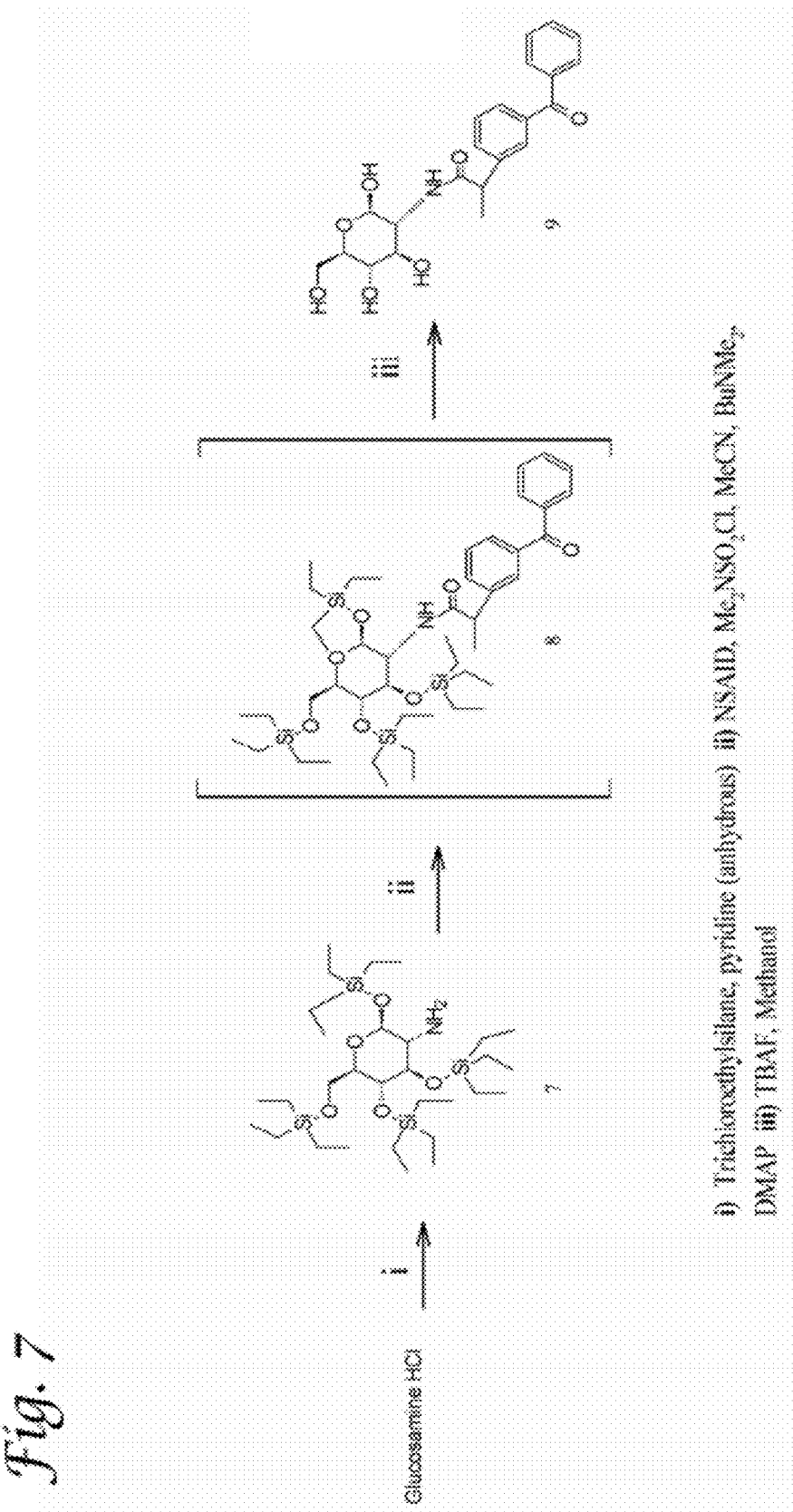
FIG. 7 shows a scheme for synthesis of a directly linked mutual prodrug that includes a glycosaminoglycan and an NSAID.

Synthesis of the mutual prodrug models were successfully completed to produce compound products 6 (Scheme I, FIG. 6) and 9 (Scheme II, FIG. 7). Methods were explored that would preserve the carbohydrate's $\beta$-conformation, protect the hydroxy (OH) groups to allow the amine ($NH_2$) to undergo selective addition to produce primary intermediates 4 (Scheme I, FIG. 6) and 7 (Scheme II, FIG. 7). Compounds 1-3 (Scheme I, FIG. 6) were synthesized from procedures adapted from Bergman et al., Chem. Ber., 1932, 975; Silva et al., J. Org. Chem., 64:5926-5929 (1999) (Supplemental Material); and Chauviere et al., J. Med. Chem., 46:427-220 (2003) as starting materials towards compound 6.

Scheme I (FIG. 6)

Preparation of 1,3,4,6-tetra-O-acetyl-2-deoxy-2-{[{[2-(4-isobutylphenyl) propanoyl]oxy}(phenyl)acetyl]amino}-$\beta$-D-glucopyranose (Compound 6)

2-deoxy-2-amino-1,3,4,6-tetra-O-acetyl-$\beta$-D-glucopyranosyl (4) Compound 3 (100 g, 0.26 mol) was titrated with triethylamine to yield a white precipitate. The precipitate was filtered and washed with $CH_2Cl_2$ (2×150 milliliters (ml)). The filtrate was dried under vacuum for 24 hours. The organic layer was washed with brine (2×100) and dried with $Mg_2SO_4$. The solvent was removed via reduced pressure rotary evaporation and product dried for 24 hours under vacuum to provide Compound 4, afforded as a white solid (87.9 grams (g), 97% yield). $^1$H NMR (d-acetone) 9.21 s, 1H), 6.15 (d, 1H), 5.38 (t, 1H), 5.08 (t, 1H), 4.31 (dd, 1H), 4.11-4.03 (m, 2H), 3.56 (t, 1H), 3.03-2.05 (dd, 6H), 2.25 (d, 3H), 2.10-2.09 (m, 3H). $^{13}$C NMR (d-acetone) 205.7, 170.1, 169.87, 169.39, 169.0, 95.20, 74.85, 72.28, 68.61, 61.90, 55.46, 19.98, 19.85, 19.82, 19.77. ES1 for C14H21NO9: FW 347 found m/z 348 [M+H+]. Mp 134° C.

2-deoxy-2-(2-chloro-2-phenyl)acetylamino-1,3,4,6-tetra-O-acetyl-$\beta$-D-glucopyranosyl (5)

Alpha-Chlorophenylacetyl chloride (20 g, 0.105 mol) was added drop-wise to stirring solution of Compound 4 (29.88 g, 0.105 mol), triethylamine (12.4 ml, 0.90 ml) in 50 ml $CH_2Cl_2$ at −10° to room temperature for 24 hours. The reaction mixture was washed with HCl (1.5 N, 2×7 ml), $H_2O$ (1×100 ml) and brine (1×100 ml). The organic phase was dried with $Mg_2SO_4$ and the solvent removed via reduced pressure rotary evaporation. The resultant syrup was crystallized with icecold acetonitrile and dried under vacuum for 24 hours to yield Compound 5 (27.4 g, 93.5%) afforded as a white solid. $^1$H NMR (d-acetone) 7.80 (s, 1H), 7.37 (s, 2H), 7.25 (s, 2H), 5.79 (s, 1H), 5.33 (d, 2H), 4.90 (s, 1H), 4.09 (d, 2H), 3.95 (s, 1H), 3.84 (s, 1H), 3.17 (s, 1H) 1.87-1.64 (m, 12H). $^{13}$C NMR (d-acetone) 205.55, 16.88, 169.69, 169.18, 168.51, 167.69, 128.85, 128.61 (2C), 127.81 (2C) 91.03, 68.54, 61.70, 60.60 53.13, 19.73, 19.70 (2C), 19.62. ES1 for C14H21NO9: FW [M+H+] 499 found m/z 500 440 [M+H+]. Mp >200(238)° C.

1,3,4,6-tetra-O-acetyl-2-deoxy-2-{[{[2-(4-isobutylphenyl) propanoyl]oxy}(phenyl)acetyl]amino}-$\beta$-D-glucopyranose (6)

Compound 5 (653 milligrams (mg), 1.45 mmol) and $\alpha$-methyl-4-[isobutyl]phenylacetic acid-Na salt in anhydrous 10 ml $CH_2Cl_2$ was stirred at room temperature for 16 hours. The solution was washed with brine (2×10 ml) and reduced via rotary evaporation to give Compound 6 (763 mg, 93.5%) as a white powder. $^1$H NMR (d-acetone) 7.73 (s, 1H), 7.41-7.13 (m, 9H), 5.81 (d, 2H), 5.38 (m, 1H), 5.04 (m, 1H), 4.26 (s, 2H), 4.10 (s, 1H), 3.96 (s, 2H), 2.48 (s, 2H), 2.01 (s, 6H), 1.84 (s, 6H), 1.65 (s, 1H), 1.53 (s, 3H), 0.90 (s, 6H). $^{13}$C NMR (d-acetone) 205.69, 173.37, 169.61, 168.73, 168.70, 140.38, 138.43, 138.03, 129.25, 128.36, 127.31, 126.84, 91.96, 75.91, 72.54, 71.66, 68.31, 52.07, 44.61, 21.72. 19.61, 17.96: Uv 203$\lambda$ nm. ES1 for $C_{35}H_{43}NO_{12}$ FW 669 found m/z 522 [M+H+] w/loss of ($C_{11}H_{15}$).

Scheme II (FIG. 7)

Preparation of 2-deoxy-2-[2-(3-benzoylphenyl)propanoic acid]amino-β-D-glucopyranosyl (Compound 9)

2-deoxy-2-amino-1,3,4,6-tetra-O-triethylsilyl-β-D-glucopyranosyl (7) Glucosamine HCl (7.32 g, 33.95 mmol) and a catalytic amount of dimethylaminopyridine (DMAP, cat.) was stirred in 100 ml anhydrous pyridine for three hours at room temperature. Chlorotriethylsilane (20.47 g, 136.27 millimoles (mmol)) was added drop wise while the solution stirred on an ice bath at −5° C. to room temperature for 16 hrs and at 40-45° C. for 2 hours. The pyridine was removed and the resulting oil was washed with 250 ml of ethyl acetate and subsequently with 250 ml of 1:1 ethyl acetate and brine. The final organic layer was dried with $Na_2SO_4$ and solvent removed via rotary evaporation to give a colorless oil, which was dried overnight under vacuum, affording Compound 7 (21.82 g; 97%) as a white foam. $^1$H NMR (CD3OD): 5.39 (d, 1H), 4.83-4.80 (m, 2H), 3.89-3.47 (m, 3H), 3.09-3.01 (dd, 1H), 1.04-0.53 (m, 60H). ES1 for $C_{30}H_{69}NO_5Si_4$: FW 636 found m/z 636 [M+] and 522 [M+H+] w/loss of ($C_6H_{15}$).

2-deoxy-2-[2-(3-benzoylphenyl)propanoic acid]amino-β-D-glucopyranosyl (9) Compound 7 (28 g, 43.5 mmol) and DMAP (cat.) was stirred in 10 ml acetonitrile on an ice bath. In a separate vessel, (2S)-2-(3-benzoylphenyl)propanoic acid (11 g, 43.55 mmol) in 10 ml acetonitrile was stirred on an ice bath with $BuNMe_2$ (8.75 ml, 120 mmol), $Me_2NSO_2Cl$ (9.67 ml, 90 mmol) until the solution became clear. Both solutions were mixed and stirred at 0° C. to room temperature over 12 hours. The acetonitrile was removed via rotary evaporation. The resulting syrup was washed with 2×150 water/ethyl acetate (1:1) and the organic layer washed with 2×100 ml brine. The organic layer was removed via rotary evaporation and the resulting syrup dried in vacuo for 12 hours to give 2-deoxy-2-(2-(3-benzoylphenyl) propanoic acid)amino-1,3,4,6-tetra-O-triethylsilyl-β-D-glucopyranosyl (Compound 8) (43 g), quantitative: ES1 for $C_{46}H_{81}NO_7Si_4$: FW 872 found m/z 857 [M+H+] w/loss of $CH_3$) as a yellow syrup. Compound 8 was directly de-protected with t-butyl ammonium fluoride/MeOH to give white precipitate that was filtered, washed with methanol and recrystallized from hot ethanol to give Compound 9 (17.3 g, 85%) as an opaque solid. $^1$H NMR (DMSO-d6) 7.63-7.24 (m, 9H), 6.17 (s, 1H), 4.65 (s, 1H), 4.56 (s, 1H), 4.44 (s, 1H), 4.21 (s, 1H), 3.61 (s, 1H), 3.45-2.10 (m, 4H), 2.83 (d, 2H), 2.25 (d, 3H), 1.1 (s, 3H). $^{13}$C NMR (DMSO-d6) 197.13, 176.39, 141.67, 137.64, 137.34, 132.54, 131.73, 129.69 (2C), 128.79, 128.47, 128.41 (2C), 128.19, 95.20, 74.85, 72.28, 68.61, 61.90, 55.46, 45.09, 18.12. ES1 for $C_{22}H_{25}NO_7$: FW 416 found m/z 416 [M+H+]. Mp 164° C.

Results

Compounds 6 and 9 are projected to be mutual prodrugs to treat disorders such as osteoarthritis via the delivery of both a NSAID and a glucosamine (or ester or derivative thereof).

Compound 6 is ibuprofen covalently bound via a linker to the amide of glucosamine, and compound 9 is a ketoprofen molecule directly linked to glucosamine, each a model MP. Physiological, enzymatic, and hydrolysis reactions are expected to affect each mutual prodrug's ester and imido-ester linkage respectively, thus making them ideal mutual prodrugs used to target the associated pain and perhaps root cause of disorders such as osteoarthritis by either oral or transdermal administration.

Though glucosamine is not currently recognized as a pharmaceutical in the United States, studies have shown that orally administered glucosamine promotes glycosaminoglycan synthesis and the production of proteoglycans that compose the lubricating fluids and support joint tissues (i.e. cartilage) thus, for example, treating osteoarthritis' root cause (McClain et al., Diabetes, 45:1003-1009 (1996); Singh et al., Diabetes, 50:2355-2362 (2001)). Glucose and glucosamine are substrates of glucokinase (Singh et al., Diabetes, 50:2355-2362 (2001)). Phosphorylated glucosamine, glucosamine-6-phosphate inhibits glucokinase and alters both glucose and subsequent glucosamine metabolism (Van Schaftigen et al., Biochem. J., 308:23-29 (1995); Virkamaki et al., Diabetes, 48:1101-1107 (1999)). Miwa et. al reported that glucokinase has a low affinity for NAG. Thus, NAG kinase mediates the phosphorylation of NAG to produce NAG-6-phosphate that does not affect glucokinase activity (Miwa et al., Enzyme Protein, 48:135-142 (1994)). Concluding that NAG-6-phosphate does not affect glucokinase activity thus allowing glucose and glucosamine to proceed through metabolism unrestricted. The biosynthesis of glycosaminoglycans from this perspective would be better promoted with the use of NAG or some other rate-limiting glucosamine analogue rather than by parent glucosamine (Gouze et al., FEBS Lett., 510:166-170 (2002)). Anastassiades, et al reports that glucosamine and analogues thereof such as NAG as well as glucosamine with varying N-linkage-chains have shown degrees of human chondrocyte cell culture growth via matrix matrix gene expression in vitro (Poustie et al., Pharmacol. Exp. Ther., 311(2):610-616 (2004)). From the pharmaceutics perspective per review and taking consideration of Anastassiades patents and patent applications (United States Patent Application Nos. 20040152665 (2003) and 20020045597 (2001); International Patent Application Publication No. WO 2002017890 A2); our assumed hypothesis states that by protecting the glucosamine's amide, the half-life of the glucosamine molecule is increased which affects its activity. Chain linkage effects have been shown in numerous literature studies such as coupling a polymer to a molecule via an ester bond to increase its half-life as method to modify a chemical entity's dissolution properties and/or biopharmaceutical properties (D'Souza et al., Journal of Pharmaceutical Sciences, 93(8): 1962-1979 (2004)).

A hindrance to the usefulness of glucosamine as a treatment for certain disorders is its bioavailability, which is typically accepted to be approximately 12-13%, although some studies seem to indicate some effective potency in mild to moderate cases of osteoarthritis (Setnikar et al., Arzneimittel-Forschung, 36(4):729-35 (1986); Biopharmaceutics & Drug Disposition, 25(3):109-116 (2004); Du et al., Biopharmaceutics & Drug Disposition, 25(3):109-116 (2004)). Although not intending to be held to any particular theory, it is our belief that these two synthesized mutual prodrugs will undergo in vivo hydrolysis to give the parent compounds. Then, each parent compound may provide its therapeutically recognized effect. Studies have not been completed to determine whether of the new mutual prodrugs dissolution profile is faster than their hydrolysis or enzymatic degradation rate constants. Although this is expected, the rates are predicted to vary since the linkages depend on the chemical nature of the covalent bonds, structure of the compounds and the surrounding conditions in vivo/in vitro.

Compound 6, the tripartite entity may undergo hydrolysis more easily than the bipartite compound 9. The ibuprofen molecule of compound 6 has the potential to undergo hydrolysis due to the linking group. The linking group's benzyl moiety could possibly then undergo an intramolecular reaction and/or enzymatic reaction that release the glucosamine molecule. Compound 9, the bipartite compound is expected to hydrolyze to the parent compounds ketoprofen and glucosamine.

These predictions however have been made based on the "in silico" calculated pKa values of compounds 6 and 9 (FIGS. 6 and 7, respectively). The in silico pKa and log P calculations of compound 6 were obtained as a result of ACD/pKa v8.02 using the ACD/I-Lab online service (available on the internet at acdlabs.com) and are as follows:

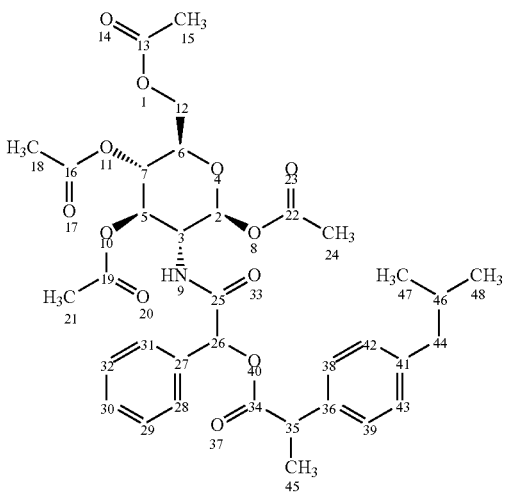

Ionic form: HL
$pKa_1$ (HL/H + L; 9) = 10.79 ± 0.70
$pKa_2$ (H2L/H + HL; 9) = -3.67 ± 0.70
Calculated log P: 6.45 ± 0.82

The in silico pKa and log P calculations of compound 9 were also obtained as a result of ACD/pKa v8.02 using the ACD/1-Lab online service and are as follows:

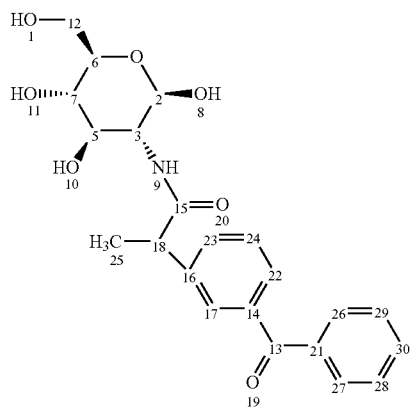

Ionic form: H5L
$pKa_1$ (HL/H + L; 9) = 15.53 ± 0.70
$pKa_2$ (H2L/H + HL; 11) = 14.69 ± 0.70
$pKa_3$ (H3L/H + L; 11) = 14.33 ± 0.70
$pKa_4$ (H4L/H + HL; 10) = 13.53 ± 0.70
$pKa_5$ (H5L/H + L; 8) = 12.03 ± 0.70
$pKa_6$ (H6L/H + HL; 9) = -2.40 ± 0.70
Calculated log P: 3.81 ± 0.48

Predictive calculations may provide an estimation of the biopharmaceutical properties. The pKa calculations reported are derived from algorithms derived from known pKa's or various chemical groups. Here we mainly focus on the pKa of the amide and/or ester linkages. The negative pKa of the amide in compound 6 suggests a large Ka value, which implies that the equilibrium constant lies to the right for the dissociation of the imido-ester bond via a hydrolysis type cleavage lending itself more to enzymatic cleavage, which can also be the case with the imido-ester of compound 6. On the other hand, the amide also has a high pKa value and, depending on its ionization, the imide-ester bond may be hydrolyzed. Furthermore, the pKa values near 2.5-3.0 are typically expected to be due to the protonation of the negatively charged oxygen. Our predictions show this to be possible on the imide ester's carbonyl oxygen. Additional studies will determine the true pathway of whether or not these mutual prodrugs have substrate specificity, hydrophilicity and/or other influences that affect the release rates of the parent drugs. Development based on their physicochemical properties and understanding of their mechanisms of release are the primary determining factors towards further mutual prodrug development.

The 'in silico' log P predictions of the compound 6 and 9 (FIGS. 6 and 7, respectively) are 6.45±0.82 and 3.81±0.48 respectively. Currently, using Lipinski's Rule of 5 (Du et al., Biopharmaceutics & Drug Disposition, 25(3):109-116 (2004)), compounds 6 and 9 rate a number of 4 and 2 respectively. Whereas, these numbers are solubility ranking based on a collection of chemical compounds estimated from data mining, e.g. using the "rule of five" to determine "drug likeness." The "rule of 5" states that poor absorption or permeation is more likely when:

A) There are more than 5H-bond donors (expressed as the sum of OHs and NHs);
B) The MWT is over 500;
C) The LogP is over 5 (or MLogP is over 4.15); and
D) There are more than 10H-bond acceptors (expressed as the sum of Ns and Os).

Poor absorption or permeability is possible since neither compound satisfies more than two criteria. Though more drug likeness is indicated for compound 9 than compound 6 in regard to their aqueous solubility and intestinal permeability based on the "rule of 5." In light of this, mutual prodrugs containing carbohydrate moieties, compounds such as these potentially fall into classes that are substrates for biological transporters, which are exceptions to the rule.

This study was primarily commenced as a pharmaceutics study to synthesize and evaluate the physicochemical properties of two proposed mutual prodrug candidates. Though the dissolution characteristics have not been discussed, we found the differential scanning calorimetry (DSC) data to be intriguing. In order to evaluate these mutual prodrugs' dissolution characteristics, a consistent crystal form must be established, which we failed to achieve. We encountered commonly observed carbohydrate phase transitions such as glassy state dynamics, which follow trends of the Tool-Narayanaswany-Moynihan model (Andreozzi et al., Journal of Physics: Condensed Matter, 15(11):S1215-S1226 (2003)). This model is an attempt to explain the glassy state transitions observed with carbohydrates and other chemical entities such as sucrose, trehalose, and (poly)vinylpryrolidone. Its application is widely used in the pharmaceutical industry to investigate the physicochemical stability and the quantitative relationship between the width of the glass transition and fragility/activation energy for structural relaxation (Pikal et al., J. of Pharm. Sci., 93(4):981-994 (2004)).

Figure 8:
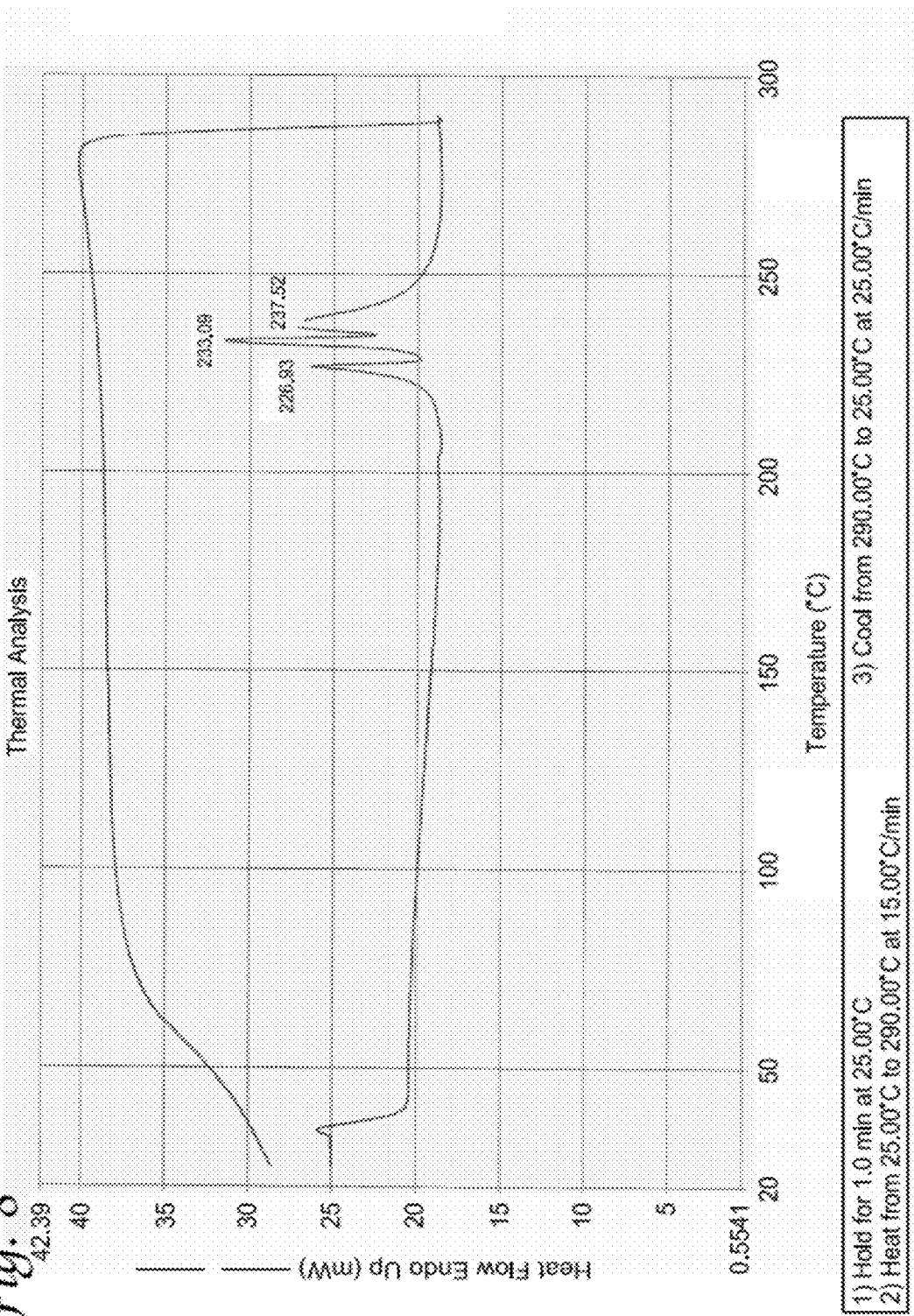
FIG. 8 shows a differential scanning calorimetry (DSC) thermograph of the mutual prodrug synthesized according to the scheme of FIG. 4 (compound 6).

In FIG. 8, the DSC thermograph of compound 6, a powder, shows three transitions indicative of polymorphs that look to be thermally stable, with phase transitions at 226.93° C., 233.09° C. and 237.52° C. respectively. All thermographs were consistent with heating at various rates. After opening all of the DSC pans, we found that the compound had sublimed and decomposed.

Figure 9:
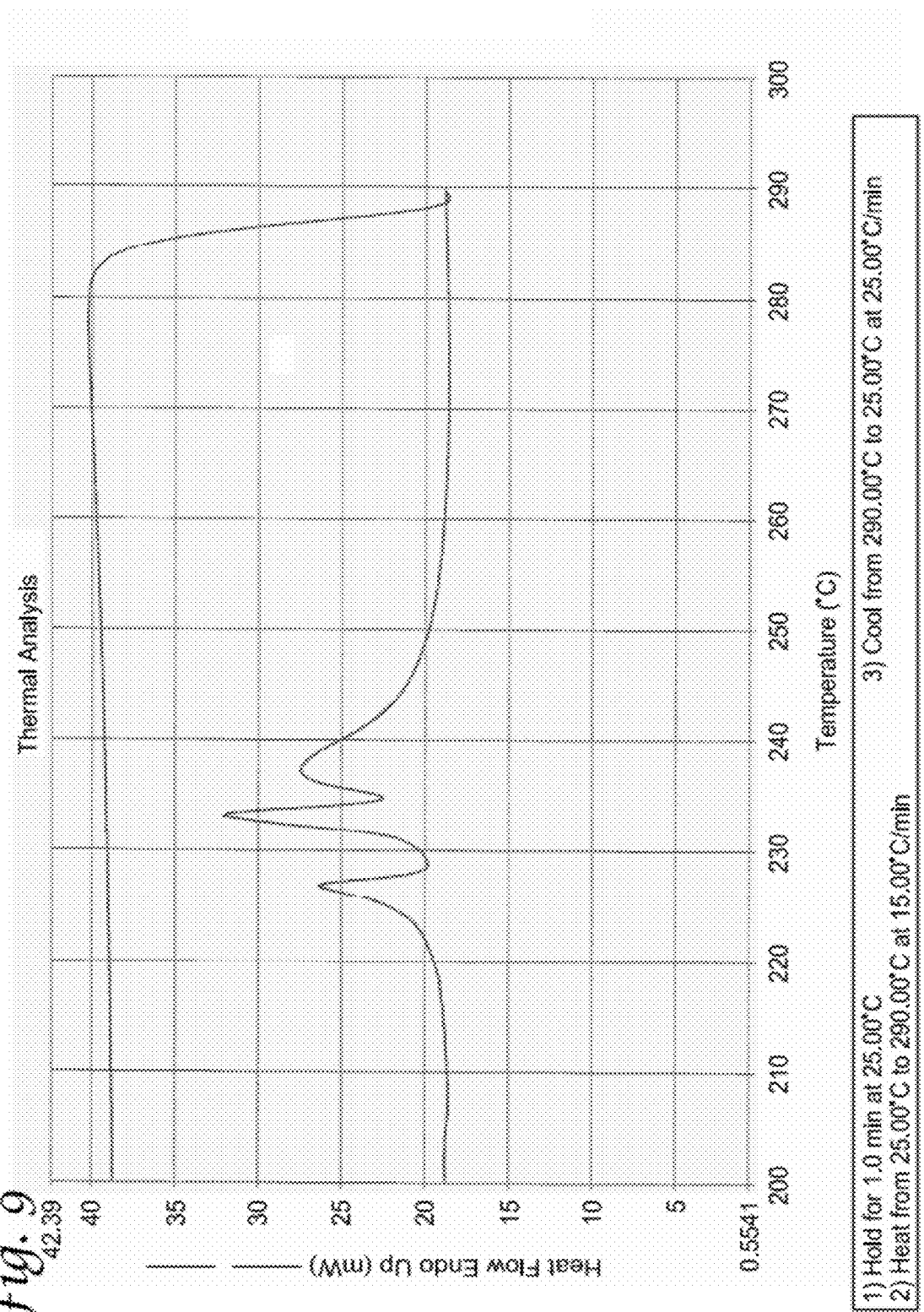
FIG. 9 shows an expanded DSC thermograph of the mutual prodrug synthesized according to the scheme of FIG. 4 (compound 6).
Figure 10:
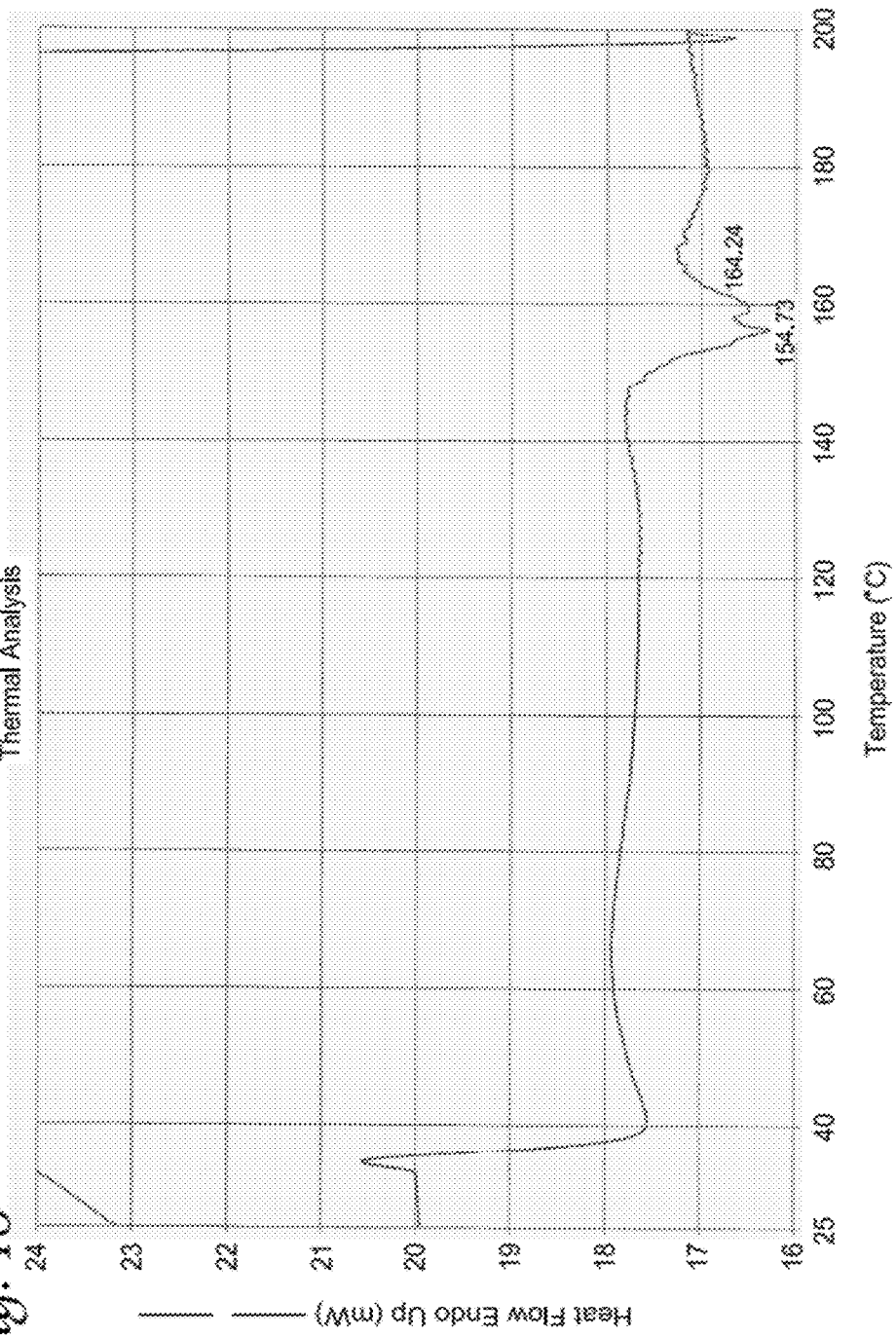
FIG. 10 shows a DSC thermograph of the mutual prodrug synthesized according to the scheme of FIG. 5 (compound 9).
Figure 11:
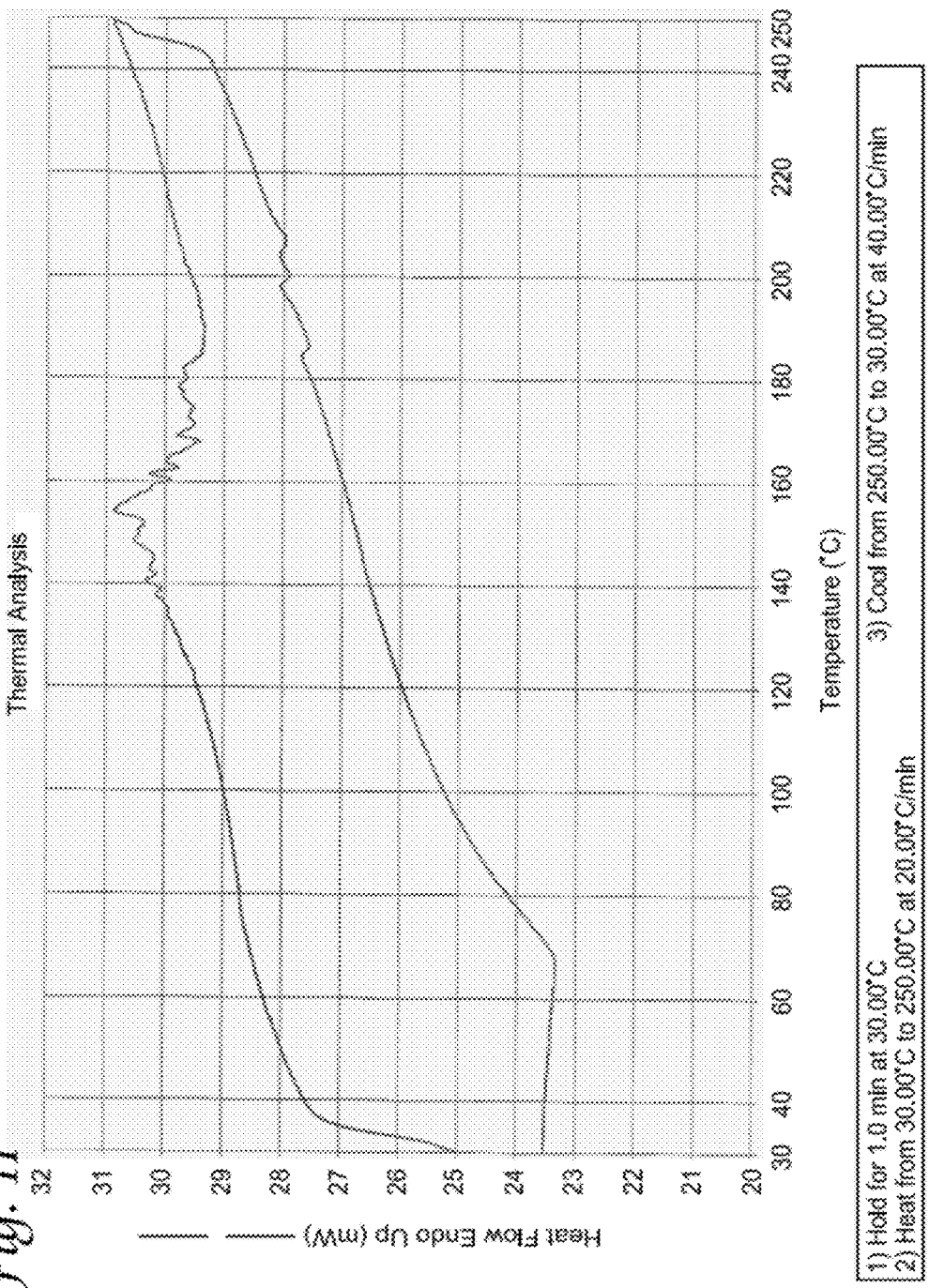
FIG. 11 shows a DSC thermograph of the mutual prodrug synthesized according to the scheme of FIG. 5 (compound 9) showing sublimation, phase change, and degradation phenomena of the compound.

The DSC thermographs of compound 9 (FIGS. 10 and 11) were difficult to obtain. Compound 9's uncorrected melting point was determined to be 164° C. Representative DSC thermograph of compounds 6 and 9 show exothermic activity (FIGS. 9 and 11), and many phase transition points indicative of sublimation, which was proven upon visual inspection. The uncorrected melting point is actually the decomposition point in DSC thermograph. Visually, compound 6 was obtained as a syrup, which was recrystallized under high vacuum pressure and/or solvent recrystallization as opaque crystals with elliptical surfaces. To obtain a clearer, picture of compound 6, we tried x-ray crystallography, which failed due to the opaqueness and complexity of the crystal structure(s). No distinct polymorph and glassy transition states were observed. Pikal et al.'s hypothesis, " . . . because physical and chemical degradation processes require atomic and molecular mobility, just as structural relaxation requires similar mobility, instability processes are correlated or 'coupled' to structural relation" (J. Pharm. Sci., 93(4):98'-994 (2004)) seems to be valid regarding compound 6 as an amorphous chemical entity.

The two mutual prodrug models were synthesized to follow the same processes and/or methodologies as prodrugs in attempts to overcome pharmaceutical and pharmacological problems such as incomplete absorption, too rapid absorption and excretion observed with NSAIDS and glucosamine. The end objective was to have an NSAID and glucosamine reach a site providing its pharmacological effect while minimizing the adverse drug events and/or effects. It is anticipated that in vitro and/or in vivo studies will verify the anticipated objective of these new synthesized mutual prodrugs, as well as derivatives and/or analogs thereof.

We have also developed and performed preliminary performulation studies of other glucosamine-NSAID analogs as a delivery system for glucosamine and NSAIDs to produce anti-inflammatory effect as well as cartilage growth. The NSAID can be, for example, ibuprofen or ketoprofen.

Example 2

Solubility and Transport of Glucosamine-NSAID Mutual Prodrug

Transdermal deliver of an NSAID-glycosamineglycan mutual prodrug, such as ibuprofen-glucosamine, can concomitantly deliver with an NSAID and a glycosamineglycan like glucosamine. In experiments showing transport of glucosamine and glucosamine mutual prodrugs across shed snake skin, glucosamine HCl was not transported across the shed snakeskin, whereas N-acetyl-glucosamine (NAG) was highly transported, even though NAG has what is considered a poor partition coefficient of about 0.017 in octanol/water.

Compound 6 has a partition coefficient (calculated in silico log P) of 6.45, and compound 9 has a partition coefficient (calculated in silico log P) of 3.81, indicating an expectation of greater lipid solubility and greater possibilities for transport to occur. It has been shown that both ibuprofen and ketoprofen are transported across shed snakeskin (U.S. Pat. No. 6,368,618 B1; Phar acta Helv 1996, Aug., 7(3):205-212; boll Chim. Farm. 2000 March-April, 139(2):67-72); both ketoprofen and ibuprofen are lipid soluble NSAIDS. It is expected that the NSAID-glucosaminglycan mutual prodrug will also be transported across shed snakesin as a model for the human epidermis; it is also expected that an NSAID ester prodrug will exhibit similar transport properties. indicating greater possibilities for transport of the mutual prodrug to occur.

Example 3

Transport of Glucosamines and Glucosamine Salts Across Skin

Oral administration of glucosamine, its derivatives and analogs, for example N-acetyl-D-glucosamine, are affected by the liver's first-pass metabolism (Setnikar et al., Arzneimittel-Forschung, 36(4):729-35 (1986); Du et al., Biopharmaceutics & Drug Disposition, 25(3):109-116 (2004)). However, a more recent report indicates that these agents may be metabolized mostly in the gut rather than solely by the liver (Aghazadeh-Habashi et al., Journal of Pharmacy & Pharmaceutical Sciences, 5(2):181-184 (2002)). Few pharmacokinetic literature reports exist on the disposition of these agents in articular cartilage (Setnikar et. al., Arzneimittel-Forschung, 43(10):1109-1113 (1993) and Arzneimittel-Forschung, 51(9):699-725 (2001)) have reported on the pharmacokinetic properties of glucosamine in dogs and man. It is estimated that approximately 87% of the original glucosamine oral dose is absorbed and excreted; <13% is widely distributed in the body; and <1% reaches osteoarthritic joints. Chondroitin is known to degrade into its basic dissaccharide components within the gut prior to further metabolism (Lamari et al., Biomed. Chromatogr., 16:95-102 (2002)). Although only a small fraction of glucosamine reaches the articular cartilage target site, it is reported to exhibit a high potency; and together glucosamine and chondroitin therapy demonstrate therapeutic efficacies over time, (McAlindon et al., JAMA, 283:1469-1475 (2000)).

Initial data shows transport of certain topically delivered glucosamine compositions of the present invention (esters of glycosaminoglycan) as compared with glucosamine-containing creams of the type currently available. These creams typically include glucosamine salts (HCl or sulfate), which are monovalent (uncharged) chemical entities that do not cross and/or penetrate the skin unless an electrical charge is applied.

The compositions analyzed included glucosamine HCl, N-acetyl glucosamine, and glucosamine-pentaacetyl as described below, in a solution of DMSO:

Glucosamine HCl
Molecular Formula=$C_{14}H_{22}ClNO_9$
Formula Weight=383.7785
Composition=C, 43.81%; H, 5.78%; Cl, 9.24%; N, 3.65%; O, 37.52%.
Molar Refractivity=Not available
Molar Volume=Not available
Parachor=Not available
Index of Refraction=Not available
Surface Tension=Not available
Density=Not available
Dilectric Constant–Not available
Polarizability=Not available
Monoisotopic Mass=383.098312 Da
Nominal Mass=383 Da
Average Mass=383.783195 Da
  N-Acetyl Glucosamine
Molecular Formula=$C_{14}H_{21}NO_9$
Formula Weight=347.3179
Composition=C, 48.41%; H, 6.09%; N, 4.03%; O, 41.46%.
Molar Refractivity=77.50±0.4 centimeters (cm)$^3$ Molar Volume=266.2±5.0 cm$^3$
Parachor=703.1±6.0 cm$^3$
Index of Refraction=1.493±0.03
Surface Tension=48.6±5.0 dyne/cm
Density=1.30±0.1 gram/cm$^3$
Dilectric Constant=Not available
Polarizability=30.72±0.5×10$^{-24}$ cm$^3$
Monoisotopic Mass=347.121634 Da
Nominal Mass=347 Da
Average Mass=347.32248 Da
   Glucosamine Pentaacetyl
Molecular Formula=C$_{16}$H$_{23}$NO$_{10}$
Formula Weight=389.3546
Composition=C, 49.36%; H, 5.95%; N, 3.60%; O, 41.09%.
Molar Refractivity=86.91±0.4 cm$^3$
Molar Volume=299.4±5.0 cm$^3$
Parachor=787.0±6.0 cm$^3$
Index of Refraction=1.492±0.3
Surface Tension=47.6±5.0 dyne/cm
Density=1.30±0.1 gram/cm$^3$
Dilectric Constant=Not available
Polarizability=34.45±0.5×10$^{-24}$ cm$^3$
Monoisotopic Mass=389.132199 Da
Nominal Mass=389 Da
Average Mass=389.359811 Da In vitro transport (diffusion) was evaluated by Franz cell diffusion experiments using shed snakeskin. Shed snakeskin is widely recognized as a sufficient model membrane to human skin for preliminary permeability studies due to the similarity in its composition to the human stratum corneum.

The shed snakeskin was hydrated in 0.1% aqueous sodium azide solution for 48 hours at room temperature. The skins were mounted to three Franz receptor cells filled with 0.1 M pH7 phosphate buffer. The receptor solution was maintained at 37° C. and stirred with a magnetic stirrer. The donor cells were clamped to each receptor cell, with the skin mounted between the receptor and donor cells, and the donor cells were filled with 100 milligrams (mg) each of glucosamine HCl (e.g., cell 1), N-acetyl glucosamine (e.g., cell 2), and glucosamine pentaacetyl (e.g., cell 3) in a 1 milliliter (ml) DMSO solution. The skin surface exposed to diffusion was 2.54 cm$^2$ (1.8 cm diameter) and the receptor cell volume was 6 cm$^3$. The system was allowed to equilibrate for two hours before samples were taken.

Twenty microliter (μl) samples of receptor solution were taken at 5, 10, 20, 40, 80, 160, and 240 minute intervals and replaced with fresh buffer. A ten μl aliquot of each sample was analyzed by high performance liquid chromatography with pulsed electrochemical detection.

Figure 12:
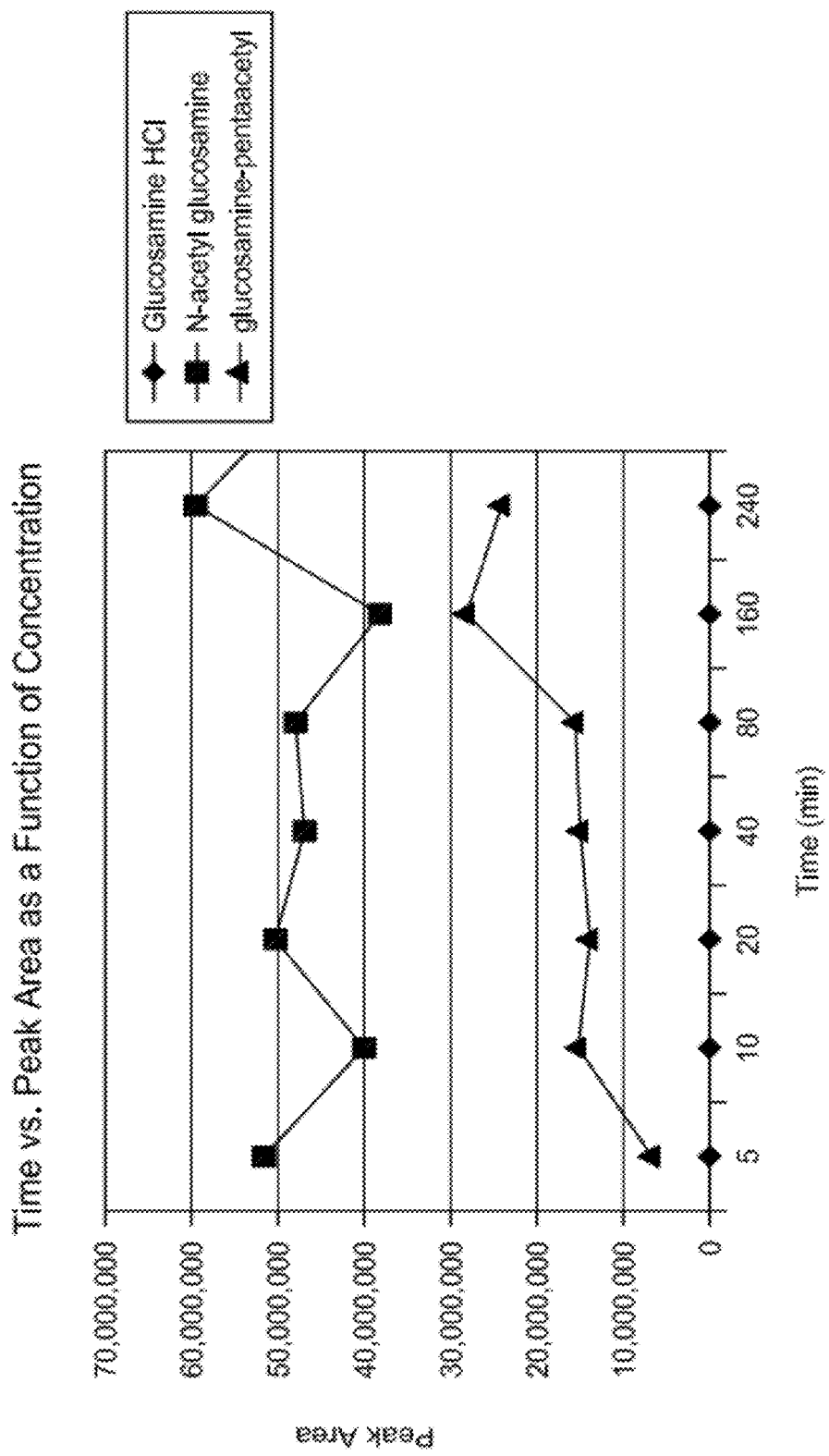
FIG. 12 shows a graph of time vs. peak area as a function of concentration for a diffusion study of compositions of (a) glucosamine HCl, (b) N-acetyl glucosamine, and (c) glucosamine pentaacetyl.

As shown in FIG. 12, there was no observable diffusion and/or transport across the skin membrane of the glucosamine HCl salt composition. The compositions of esters of glycosaminoglycan (N-acetyl glucosamine and glucosamine-pentaacetyl) showed immediate and constant diffusion and/or transport from 5 minutes to 240. Each receptor cell volume was analyzed, revealing over 50% transport of esters (e.g., of the 100 mg of the esters in the delivery phase, over 50 mg of the esters were delivered over time.

Example 4

Transdermal permeability of
N-acetyl-D-glucosamine

As an objective of this research was to evaluate transdermal permeability of glucosamines, esters, and derivatives thereof, to assess the feasibility of pursuing a percutaneous formulation for local therapy, NAG was selected for analysis because it is an active metabolite and prodrug of glucosamine; and owing to its commercial availability, relatively low cost and stability. It possesses the following physical and chemical characteristics making it a reasonable candidate for transdermal delivery and percutaneous absorption: a) high potency, b) reasonably lipid soluble, c) low molecular weight, d) unique biochemical pathway with active transport from blood into articular cartilage. (Milewski, Biochimica et Biophysica Acta, 1597:173-192 (2002)). Furthermore, exogenous glucosamine is understood to promote glycosaminoglycan synthesis toward the production of proteoglycans by avoiding the rate-limiting steps of its conversion from glucose to glucosamine, and ultimately to N-acetyl-D-glucosamine by glutamine (fructose-6-phosphate amidotransferase) (McClain et al., Diabetes, 45:1003-1009 (1996)). Glucose and glucosamine are substrates of glucokinase (Singh et al., Diabetes, 50:2355-2362 (2001)). The phosphorylated glucosamine product, glucosamine-6-phosphate, inhibits glucokinase and alters both glucose and subsequent glucosamine metabolism (Van Schaftigen et al., Biochem. J., 308:23-29 (1995)). Miwa et al. reported that glucokinase has a low affinity for NAG (Enzyme Protein, 48:135-142 (1994)). Thus, NAG kinase mediates the phosphorylation of NAG to produce NAG-6-phosphate that does not affect glucokinase activity (Miwa et al., Enzyme Protein, 46:135-142 (1994)), allowing glucose and glucosamine to proceed through metabolism unrestricted. Thus, the biosynthesis of glycosaminoglycans from this perspective was believed to be better promoted, in certain embodiments and for certain specific uses, by the use of NAG or some other rate-limiting glucosamine analog rather than by glucosamine (Shikhman et al., J. Immunol., 166:5155-5160 (2001)), although the use of glucosamine is not precluded.

Permeability was evaluated by employing NAG suspensions of various known membrane transport enhancing reagents, ethanol, oleic acid, isopropyl myristate, isopropyl palmitate; NAG solutions of water and phosphate buffer; and NAG saturated dimethylsulfoxide (DMSO) solution.

Glucosamine and chondroitin salts are charged, highly polar, aqueous soluble, and poor candidates for transdermal absorption. Currently, there are topical products containing these ingredients as salts marketed nutraceuticals for the treatment of osteoarthritis, which contains ingredients whose effects may be mistaken in the short term as being therapeutic NAG an acetylated glucosamine metabolite is less polar and neutral appears to be a more likely candidate for transdermal delivery and percutaneous absorption.

Glucosamine is metabolized to NAG via the hexosamine pathway; glucosamine or galactosamine, plus a uronic acid, is incorporated as a disaccharide unit into all macromolecules requiring amino sugars such as keratan, dermatan, chondroitin, hyluronates, and heparin, to produce glycosaminoglycans (GAGs). GAGs are highly negatively charged molecules, with an extended conformation, and demonstrate high viscosity and low compressibility ideal as a lubricating fluid for anatomical joints. The majority of GAGs in the body are linked to core proteins, to form proteoglycans or mucopolysaccharides, which are basic components of skin, tissue, and cartilage. (Merrick et al., J. Bio. Chem. 5:235 (1960); Milewski, "Glucosamine-6-phophate synthase," Biochimica et Biophysica Acta, 1597:173-192 (2002).

Materials and Methods
Chemicals

NAG of 99.9+% purity was purchased from MP Biomedical (Aurora, Ohio). All enhancer reagents purchased for this study were at 99.9+% purity. All other reagents were of analytical grade and used without further purification.

Analysis

NAG analysis was carried out using high-performance anion exchange chromatography with pulsed amperometric detection (HPAE-PAD) on a Dionex DX-500 HPLC system (Dionex, Sunnyvale, Calif.) that included a GP40 gradient pump, ED40 Electrochemical detector, AS3500 autosampler and a PEAKNET Chromatography Workstation, ("Optimal Settings for Pulsed Amperometric Detection of Carbohydrates Using the Dionex ED40 Electrochemical Detector," Technical Note 21, Dionex Corp., Sunnyvale, Calif., USA.; Clarke et al., Anal Chem, 71:2774-2781 (1999); Campo et al., J. Chrom. B, 765:151-160 (2001); LaCourse, W. R. Pulsed Electrochemical Detection in High-Performance Liquid Chromatography, John Wiley & Sons Inc. (1997)). The HPAE-PAD was equipped with a CARBOPAC PA20 (3×150 mm), analytical anion-exchange column (Dionex, Sunnyvale, Calif.) for the rapid, high-resolution separation of monosaccharides and disaccharides, using pulsed amperometric detection, a CARBOPAC PA20 analytical guard column (3×30 mm) (Dionex, Sunnyvale, Calif.), and a carbonate trap column (25×15 mm) (Dionex, Sunnyvale, Calif.). Mobile phase (A) was degassed and prepared with deionized water. The mobile phase (B) included 0.02 N NaOH prepared with deionized water and filtered with 0.45 micrometer (μm) filters in a solvent filtration apparatus (Waters-Millipore, Milford, Mass., USA) that was degassed under vacuum. The mobile phase system was run at a gradient concentration of 16 mM NaOH at a flow rate of 0.5 milliliters per minute (ml/min). A standard calibration curve of NAG (FIG. 13) was obtained with linear regression and value of $R^2$=0.9936. Each sample set was run with external standards. The sample concentration values were obtained via the PEAKNET software. These values were compared with to those obtained by calculations of the peak area and peak height observe as functions of the standard curve's linear regression equation. The instrument sensitivity was approximately $10^{-4}$ units.

Solubility Measurements

An excess amount of NAG (pKa 6.73) was placed in separate vials containing 10 ml deionized water, 10 ml n-hexane and 10 ml phosphate buffer (pH 6, 6.73, and 7.4; 1 M) and stirred at 37° C. for 24 hours. The solutions were centrifuged for 5 min at 9000 rev/min and the supernatant filtered with cellulose acetate membrane filters (0.45 μm pore size) (Dionex, Sunnyvale Calif.). The NAG concentration in each filtrate was determined by HPAE-PAD after the appropriate dilution.

Determination of Partition Coefficients

The oil/water partition coefficient for NAG was determined using n-hexane/phosphate buffer (pH 5.5 6, 6.73, and 7.4, 0.1 M) and n-hexane/water (Bernacki et al., J. Supramolecular Structure, 7:235-250 (1977)). In each case 5 ml of n-hexane was mixed with aqueous solutions containing NAG and shaken at 37° C. for 24 hours. The mixture was afterwards centrifuged and the organic and aqueous phases separated. The NAG concentration in the filtrates was determined by HPAE-PAD after the appropriate dilution.

In-Vitro Membrane Permeation

Shed snakeskin were used as a model membrane for permeation studies using the NAG suspensions in known membrane permeation enhancers; ethanol, oleic acid, isopropyl myristate, and isopropyl palmitate; saturated solutions of NAG in water and in phosphate buffer; as well as in a saturated DMSO solution and phosphate buffer (pH 5.5) containing ethanol at 2%, 5%, 10%, 25%, and 50% solutions.

The skins were hydrated in 0.1% aqueous sodium azide solution at room temperature for 48 hrs. Franz-cell diffusions experiments were carried out. In general the receptor cell was filled with 7.4 pH 0.1 M phosphate buffer and the donor cell filled with a solution or suspension. For the phosphate buffer (pH 5.5) containing ethanol at 2%, 5%, 10%, 25%, and 50% solutions in the donor phase, the receptor phase consisted of phosphate buffer (pH 5.5, 0.1 M). The receptor solution was maintained at 37° C. and stirred with a magnetic stirrer.

The snake skins were mounted between the receptor and donor cells. The surface exposed to diffusion was 2.54 $cm^2$ (diameter 1.8 cm) and the receptor cell volume was 6 $cm^3$. The donor cell was covered with plastic film. The system was allowed to equilibrate at 37° C. for two hours before each experiment. To the donor cells, 5 ml of the NAG-enhancer suspension or solution was added. Samples were taken at intervals over a 24-hour period, 200-μl samples of receptor solutions were taken and replaced with fresh buffer; experiments were conducted in triplicate. The amounts of NAG that permeated through the snakeskin were determined by HPAE-PAD.

Data Treatment

Steady state flux ($J_{ss}$) for NAG (mg/$cm^2$/h) was calculated from its increasing amount in the receptor medium (Bach et al., Eur. J. Pharm. Biopharm, 46:1-13 (1998)). NAG's permeability coefficient ($k_p$) in cm/h was calculated from known physiochemical parameters, (Hadgraft et al., "Feasibility Assessment in Topical and Transdermal Delivery: Mathematical Models and In Vitro Studies," in Transdermal Drug Delivery. $2^{nd}$ Ed. Marcel Dekker, Inc., pages 1-23 (2003)). Lag time ($t_{lag}$) was determined graphically from the cumulative amount of drug released per unit area (mg/$cm^2$) versus time plots. A square root of time ($t^{1/2}$) versus cumulative amount of drug released per unit area (mg/$cm^2$) was obtained to monitor NAG in vitro release rate (mg/$cm^2$), (Guidance for Industry: SUPAC-SS Semisolid Dosage Forms. Scale-up and Postapproval Changes: Chemistry, Manufacturing, and Control; In Vitro Release Testing and In Vivo Bioequivalence Documentation. US Department of Health and Human Services, Food and Drug Administration, Center for. Drug Evaluation and Research, May 1997).

Results

Initial permeability investigations were carried out using shed snakeskin as a model membrane to human skin; a widely recognized and sufficient model for preliminary studies due to its similarity in composition to the human stratum corneum (Itoh et al., "Use of Shed Snake Skin as a Model Membrane for In Vitro Percutaneous Penetration Studies: Comparison with Human Skin," Pharm. Res., 7:1042-1047 (1990)). Negligible NAG transport was observed from suspensions of membrane permeability enhancers; ethanol, oleic acid, isopropyl myristate and isopropyl palmitate. No permeation was observed from the aqueous solutions of NAG in water or phosphate buffer solutions (pH 5.5, 6.0, 6.73, and 7.4; 0.1 M). As a qualitative correlation to a selection of NAG's partition coefficients shown in Table 1, permeation of NAG from the aforementioned membrane penetration enhancer suspensions or aqueous solutions was expected.

TABLE 1

Experimentally determined partition coefficients for N-acetyl-D-glucosamine (NAG) (pKa 6.73) and permeability coefficient ($k_p$)

| n-hexane/ pH 5.5 buffer | n-hexane/ pH 6.0 buffer | n-hexane/ pH 6.73 buffer | n-hexane/ pH 7.4 buffer | Octanol/ water[15] | $k_p$(cm/hr) |
|---|---|---|---|---|---|
| 0.252 | 0.194 | 0.092 | 0.091 | 0.017 | 0.731 |

[15]Bernacki et al., J. Supramolecular Structure, 7: 235-250 (1997)

DMSO was chosen for evaluation as a benchmark permeation enhancer due to its physical properties and well-documented enhancement properties (Franz et al., "Dimethyl sulfoxide," in *Percutaneous Enhancers*. Ed. Smith, E. W., Maibach, H. I, CRC Press, Inc., pages 112-127 (1995)). Enhancers are reported to disrupt intercellular lipids of the stratum corneum, by increasing a drug's partitioning into the stratum corneum with a concomitant increase in drug permeation through the intercellular junctions via percutaneous absorption. (Barry, J. Control. Rel., 15:237-248 (1991); Williams et al., Crit. Rev. Ther. Drug Carrier Syst., 9:305-353 (1992); Sinha et al., Drug Dev. Ind. Pharm., 26:1131-1140 (2000)). From the plot containing cumulative NAG concentration per unit area $(mg/cm^2)$ versus $time^{1/2}$ $(hour^{1/2})$ NAG's in vitro release rate was shown to be 73.48 µg/cm² (FIG. 13) with high linearity in transport thus exhibiting no lag time, as indicated in Table 2. The assumption taken is that NAG's high polarity and its low permeation coefficient, as shown in Table 3, contributes to its inability to be transported efficiently by means of single permeation enhancer or in aqueous solution.

TABLE 2

Physiochemical data obtained for the permeation of N-acetylglucosamine (NAG) through shed snake's skin via a saturated dimethyl sulfoxide (DMSO) solution in the donor phase and pH 7.4 phosphate buffer in receptor phase.

| Parameter | |
|---|---|
| $J_{ss}$ (mg/cm²/h) | 73.48 |
| $t_{lag}$ (h) | |
| In Vitro release rate (mg/cm²) | 186.64 |
| $R^2$ | 0.9736 |

TABLE 3

Physicochemical data obtained for the permeation of N-acetylglucosamine (NAG) through shed snake's skin via phosphate buffer (pH 5.5) containing ethanol at 2%, 5%, 10%, 25%, and 50% solutions in the donor phase and pH 5.5 phosphate buffer in the receptor phase.

| Parameter | 2 | 5 | 10 | 25 | 50 |
|---|---|---|---|---|---|
| | | | (% Ethanol) | | |
| $J_{ss}$ (mg/cm²/h) | 112.61 | 119.53 | 211.61 | 205.93 | 77.96 |
| In Vitro release rate (µg/cm²) | 286.03 | 303.61 | 537.49 | 523.06 | 198.02 |
| $t_{lag}$ (h) | | | | | |
| $R^2$ | 0.9778 | 0.8751 | 0.7966 | 0.9924 | .9836 |

Figure 13:
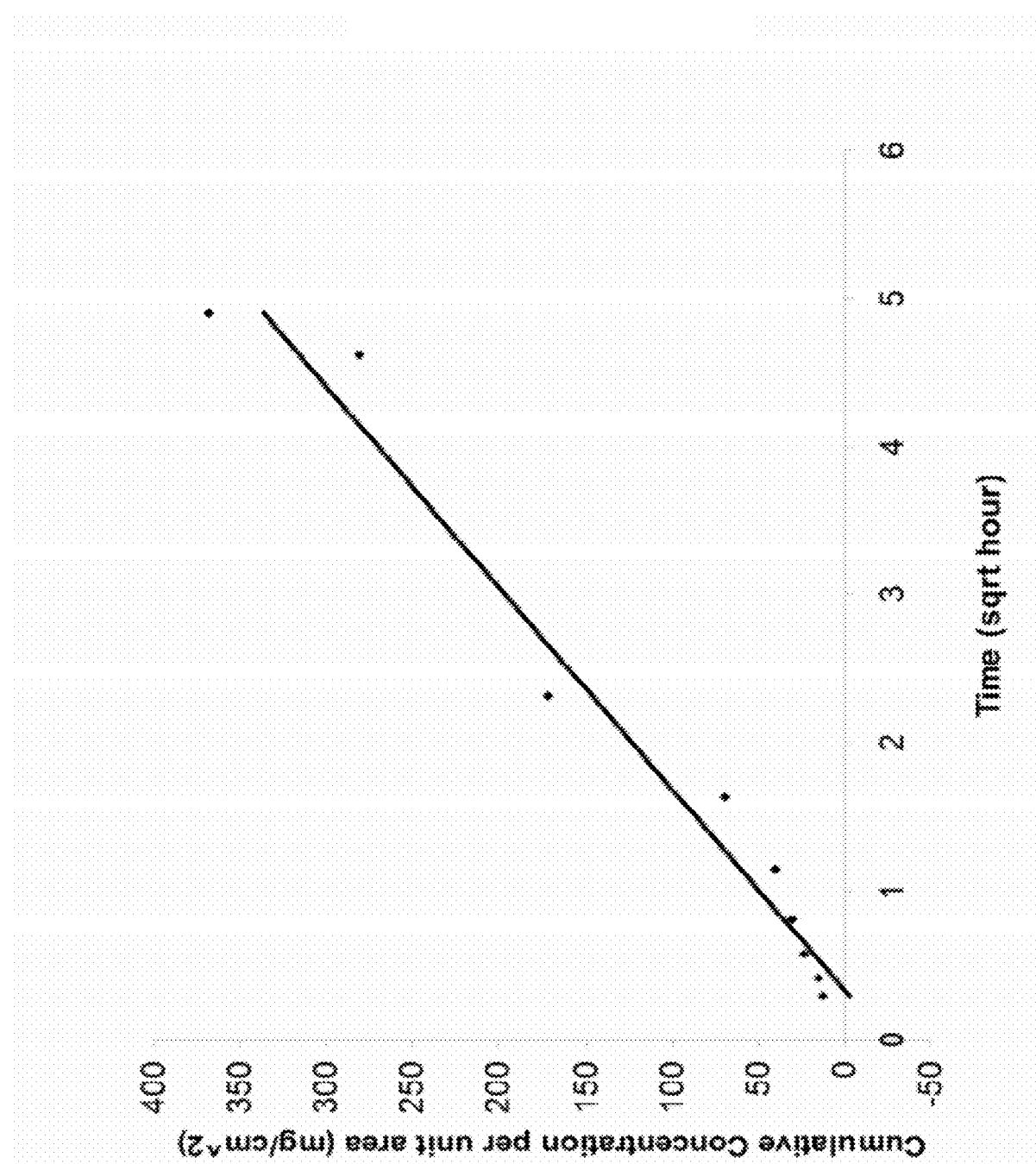
FIG. 13 is a graph of the effect of DMSO on the cumulative permeation of N-acetyl glucosamine through shed snake skin.

The study shows that DMSO allows NAG to be transported immediately and continuously with a linear concentration increase over time, as evidenced in FIG. 13, which shows the effect of DMSO on the cumulative permeation of NAG at 37.5° C. through shed snake skin (cumulative concentration vs $time^{1/2}$, each point representing the mean+/− standard deviation, n=3).

Figure 14:
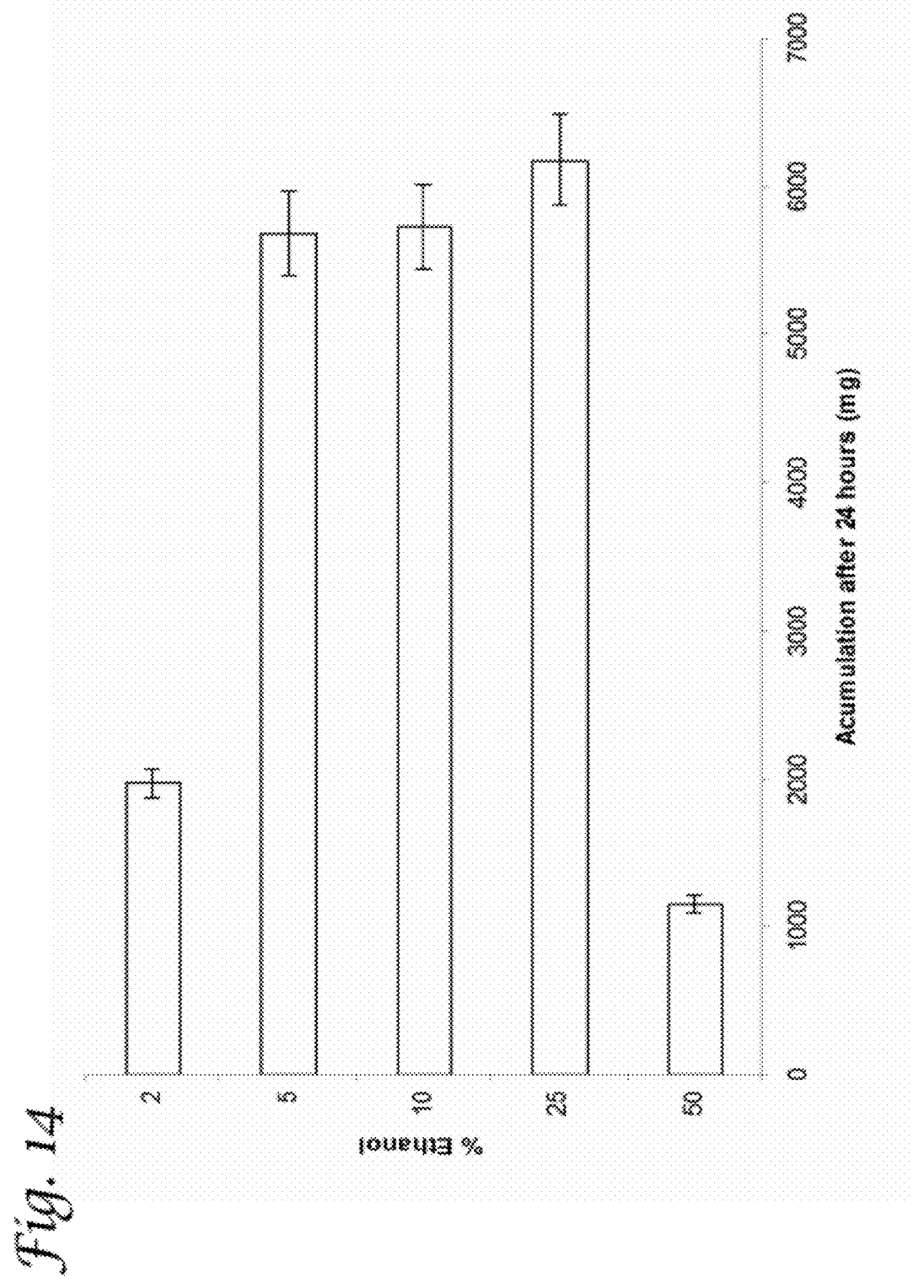
Figure 15:
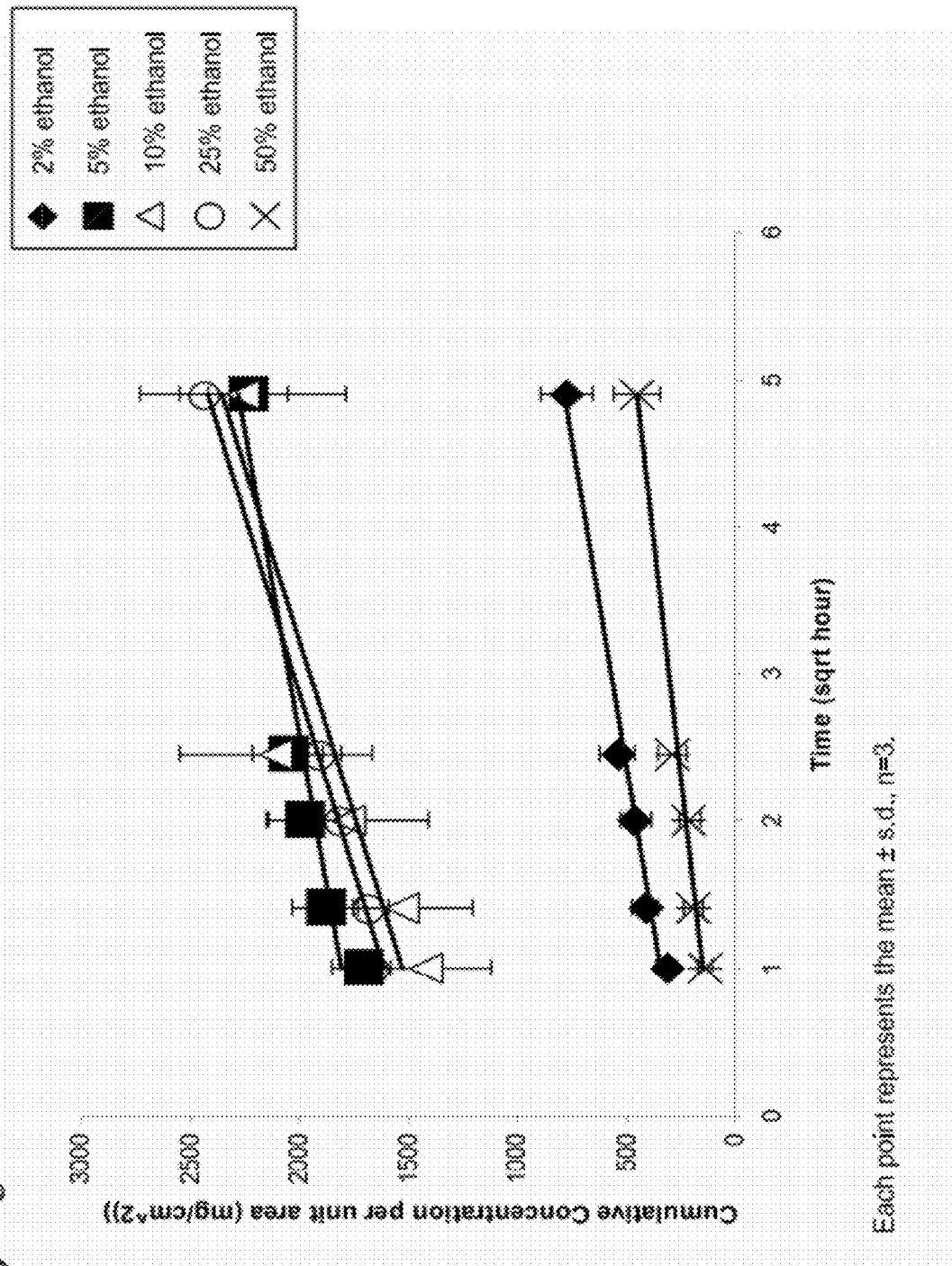
FIG. 15 is a graph showing the effect of ethanol concentration on cumulative permeation of N-acetyl glucosamine at 37.5° C. through shed snake skin at 2%, 5%, 10%, 25%, and 50% ethanol, by percentage volume of aqueous phase and ethanol containing NAG.

This study also incorporated NAG into an ethanol/buffer solution at various concentrations. Ethanol as an enhancer is known to promote the transdermal penetration and percutaneous absorption of many drugs, (Berner et al., "*Alcohols, Percutaneous Penetration Enhancers,*" in Alcohols. Eds. Smith, E. W. Maibach, H. I., CRC Press, Boca Raton, Fla., pages 45-60 (1995)). The oil/water partition coefficient increases with the decrease in pH of the buffer solution, as shown in Table 1. NAG's transdermal transport was not observed from phosphate buffer or ethanol where it is highly soluble and insignificantly soluble respectively. Its permeation was observed in sink conditions from the phosphate buffer (pH 5.5) containing ethanol at 2%, 5%, 10%, 25%, and 50%, as reported in FIG. 14, showing accumulation of NAG through shed snake skin in Franz type receptor cells from phosphate buffer (pH 5.5) after 24 hours. The cumulative concentration of the solutions containing 5%, 10%, and 25% ethanol are very similar after 24 hrs, whereas the 2% and 50% ethanol in buffer solutions delivery significantly less NAG (FIG. 15, showing the effect of ethanol concentration cumulative permeation of NAG at 37.5° C. through shed snake skin, cumulative concentration versus $time^{1/2}$). Beyond 50% ethanol concentration in buffer, the NAG precipitated. The flux values for 10% and 25% ethanol concentration are similar, whereas the 5% is half that of both. Graphically, each has a slightly different linear permeation profile up to the approximate experimental mid-point. At the conclusion of the 24-hour endpoint each solution had delivered similar amounts of NAG.

These results overall suggest that thermodynamic and solubility effects affect the permeation of NAG in correlation to use of DMSO at 100% (Kurihara-Bergstrom et al., J. Inv. Derma., 89:274-280 (1987)) and the varying concentrations of ethanol in buffer solutions. NAG's in vitro flux and release rates from ethanol in buffer solutions overall exceeded those permeation values obtained from DMSO. This shows that 5-25% concentration of ethanol as an enhancer in delivery vehicles to be a useful starting point towards the formulation of a transdermally delivered/percutaneously absorbed NAG composition.

The current study also shows DMSO to be a skin penetration enhancer for NAG. DMSO is generally used in veterinary drug delivery, (Magnusson et al., Adv. Drug Del. Rev., 50:205-227 (2001)). The use of DMSO in NAG formulation may be useful for localized osteoarthritis treatment in animals, since DMSO is not an FDA approved excipient for human use in topical/transdermally delivered pharmaceutical products. Furthermore, unpublished preliminary results in our laboratory show that NAG may have adequate permeation from other drug delivery vehicles. It is anticipated that further in vitro studies will determine other NAG formulations will effectively demonstrate transdermal delivery towards percutaneous absorption.

Example 5

Permeation of N-Acetyl Glucosamine (NAG) in Pluronic Organo-Gel Formulations Across Shed Snakeskin The objective of this study was to further evaluate the permeation of NAG in pluronic-organo-gel formulations across shed snake's skin. These pluronic gel formulations each contained lecithin-isopropyl palmitate and/or lecithin-vitamin E component as the enhancer and organic phase. Isopropyl palmitate is a well-studied enhancer. Sparse literature reports concerning the permeation enhancement effects of vitamin E and soy lecithin are available other than patents and patent applications describing various dosage forms.

For these studies, NAG was chosen as the compound of choice, even though it has a octanol-water partition coefficient of 0.017 (pH 7.4) (Bernacki et al., J. Supramolecular Structure, 7:235-250 (1977)). Mahjour and co-workers (Journal of Controlled Release, 14(3):243-52 (1990)) studied the effect of lecithins on in vitro skin permeability with several drugs with various NAG's octanol-water partition coefficients. They found that soy lecithins improved the permeability of all the drugs including procaterol and oxymorphone which both have a comparatively low octanol-water partition coefficient of −0.37 (pH 7.7) and 0.0 (pH 7.4) respectively. The most impressive finding was that the soy lecithins enhancement effect was the highest for procaterol, which has the lowest octanol-water partition coefficient of the drugs studied (Mahjour et al., Journal of Controlled Release, 14(3): 243-52 (1990)). As for vitamin E, it is postulated to act as a permeation enhancer by intercalating within the lipid bilayer of the stratum corneum, which alters the membrane's permeability (Trivedi et al., European Journal of Pharmaceutical Sciences, 3(4):241-243 (1995)).

Vitamin E has a two-fold effect within biological membranes as an antioxidant and membrane stabilizer. Structurally, vitamin E's chromanol ring's hydroxyl group is believed to situate in the polar head environment of the phospholipid membrane, while the phytyl chain intercalates with the lipid acyl chains. Trivedi and co-workers observed vitamin E's permeation enhancement (European Journal of Pharmaceutical Sciences, 3(4):241-243 (1995)). Their conclusion was that overall improvement in the permeability of the stratum corneum is moderate. This is a result from the limited insertion of vitamin E within the ceramide-rich bilayer structure. Thus their final concluding statement was that overall vitamin E enhancement effect " . . . will not be tremendous but discernible nonetheless" (Trivedi et al., European Journal of Pharmaceutical Sciences, 3(4):241-243 (1995)).

Experimental

Materials

NAG was purchased from MP Biomedicals, Inc (Aurora, Ohio). Poloxamer 407 (PLURONIC F127; Polyethylene-Polypropylene Glycol), soy lecithin and isopropyl palmitate were purchased from Spectrum Chemical Mfg. Corp. (Gardena, Calif.). Vitamin E (mixed tocopherol complex) was purchased from Solgar Vitamin and Herb (Leonia, N.J.). Water used for the preparation was double distilled and deionized by a Millipore purification system (Continental Water Systems Corp., El Paso, Tex.).

Vehicle Preparation

Twenty percent poloxamer 407 (PLURONIC F127; Polyethylene-Polypropylene Glycol) gels were made by standard methods e.g. dissolving the poloxamer into cold water under refrigeration for 24 hours to produce the pluronic gel phase. NAG was incorporated into the pluronic gel phase. The final formulations were prepared via the emulsification of the select organic phase with the pluronic gel phase using Luerlock connected syringes.

In-Vitro Membrane Permeation Studies

Shed snakeskins were used as the model membrane for these permeation studies using the NAG semi-solid gel formulations. The skins were hydrated in 0.1% aqueous sodium azide solution at room temperature for 48 hrs. Franz-cell diffusions experiments were carried out. In general the receptor cell was filled with a 7.4 pH 0.1 M phosphate buffer. The receptor solution was maintained at 37° C. and stirred with a magnetic stirrer. The snakeskins were mounted between the receptor and donor cells. The surface exposed to diffusion was 2.54 cm$^2$ (diameter 1.8 cm) and the receptor cell volume was 6 cm$^3$. The donor cell was covered with plastic film. The system was allowed to equilibrate at 37° C. for two hours before each experiment. The donor cells were filled with a 5 ml of the semisolid NAG pluronic-organo-gel formulation. Samples (N=3) were taken at intervals over a 48-hour period, 200 µl samples of receptor solutions were taken and replaced with fresh buffer; experiments were conducted in triplicate. The amounts of NAG that permeated through the snakeskin were determined by HPAE-PAD.

HPAE-PAD (HPLC) Analysis

Figure 16:
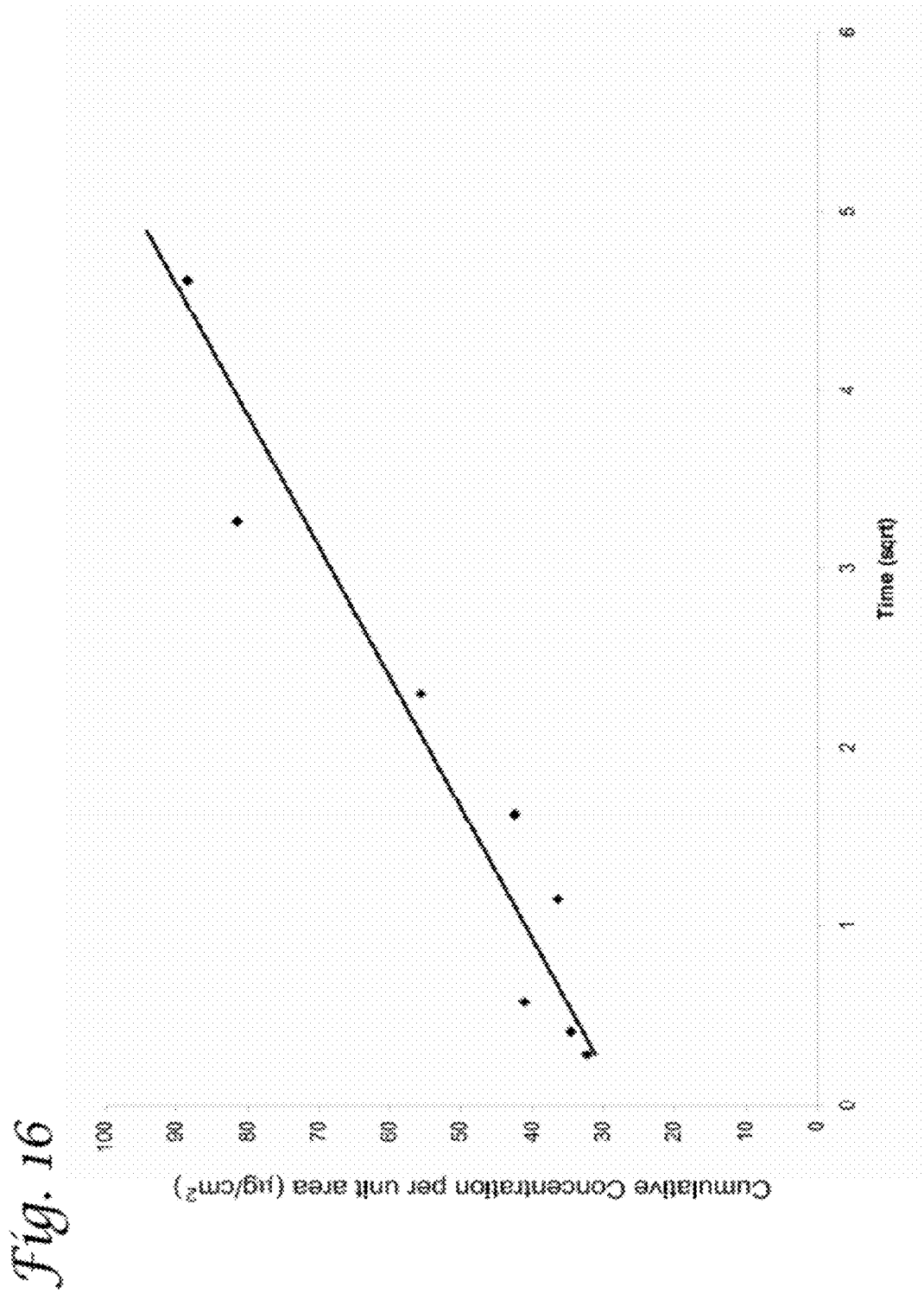
FIG. 16 is a graph showing the effect of soy lecithin-vitamin E on N-acetyl glucosamine permeation across shed snake skin.

NAG analysis was carried out at the University of Georgia, Center for Complex Carbohydrate Research Center. High-performance anion exchange chromatography with pulsed amperometric detection (HPAE-PAD); Dionex, Sunnyvale, Calif. USA); on a Dionex DX-500 HPLC system consisting of a P40 gradient pump, ED40 Electrochemical detector, AS3500 autosampler and PeakNet Chromatography Workstation was utilized. The HPAE-PAD was equipped with CARBOPAC PA20 (3×150 mm), analytical anion-exchange column for the rapid, high-resolution separation of monosaccharides and disaccharides, using pulsed amperometric detection and a CARBOPAC PA20 analytical guard column (3×30 mm) and a carbonate trap column (25×15 mm). Mobile phase (A) was degassed and prepared with deionized water. The mobile phase (B) consisted of 0.02 N NaOH prepared with deionized water and filtered with 0.45 µm filters in a solvent filtration apparatus (Waters-Millipore, Milford, Mass., USA) that was degassed under vacuum. The mobile phase system was run at a gradient concentration of 16 mM NaOH at a flow rate of 0.5 ml/min. A standard calibration curve of NAG (FIG. 16, showing the effect of soy lecithin-vitamin E on NAG permeation across shed snake skin, cumulative concentration (n=3) per unit area +/− standard deviation as a function of time$^{1/2}$) was obtained with linear regression and value of $R^2$=0.9936. Each sample set was run with external standards. The sample concentration values were obtained via the PEAKNET software. These values were compared with to those obtained by calculations of the peak area and peak height observe as functions of the standard curve's linear regression equation. The instrument sensitivity was approximately 10$^{-4}$ units.

Data Analysis

Steady state flux ($J_{ss}$) for NAG (mg/cm$^2$/h) was calculated from its increasing amount in the receptor medium (Bach et al., Eur. J. Pharm. and Biopharm., 46:1-13 (1998)). NAG's permeability coefficient ($k_p$) in cm/h was calculated from known physiochemical parameters (Hadgraft et al., "Feasibility Assessment in Topical and Transdermal Delivery Mathematical Models and In Vitro Studies," in Transdermal Drug Delivery, 2$^{nd}$ Ed. Marcel Dekker, Inc., pages 1-23 (2003)). Lag time ($t_{lag}$) was determined graphically from the cumulative amount of drug released per unit area (mg/cm$^2$) versus time (h) plots. A square root of time ($t^{1/2}$) versus cumulative amount of drug released per unit area (mg/cm$^2$) was obtained to monitor NAG in vitro release rate (mg/cm$^2$) (Guidance for Industry: SUPAC-SS Semisolid Dosage Forms. Scale-up and Postapproval Changes: Chemistry, Manufacturing, and Control; In Vitro Release Testing and In Vivo Bioequivalence Documentation. US Department of Health and Human Services, Food and Drug Administration, May 1997).

Results

Figure 17:
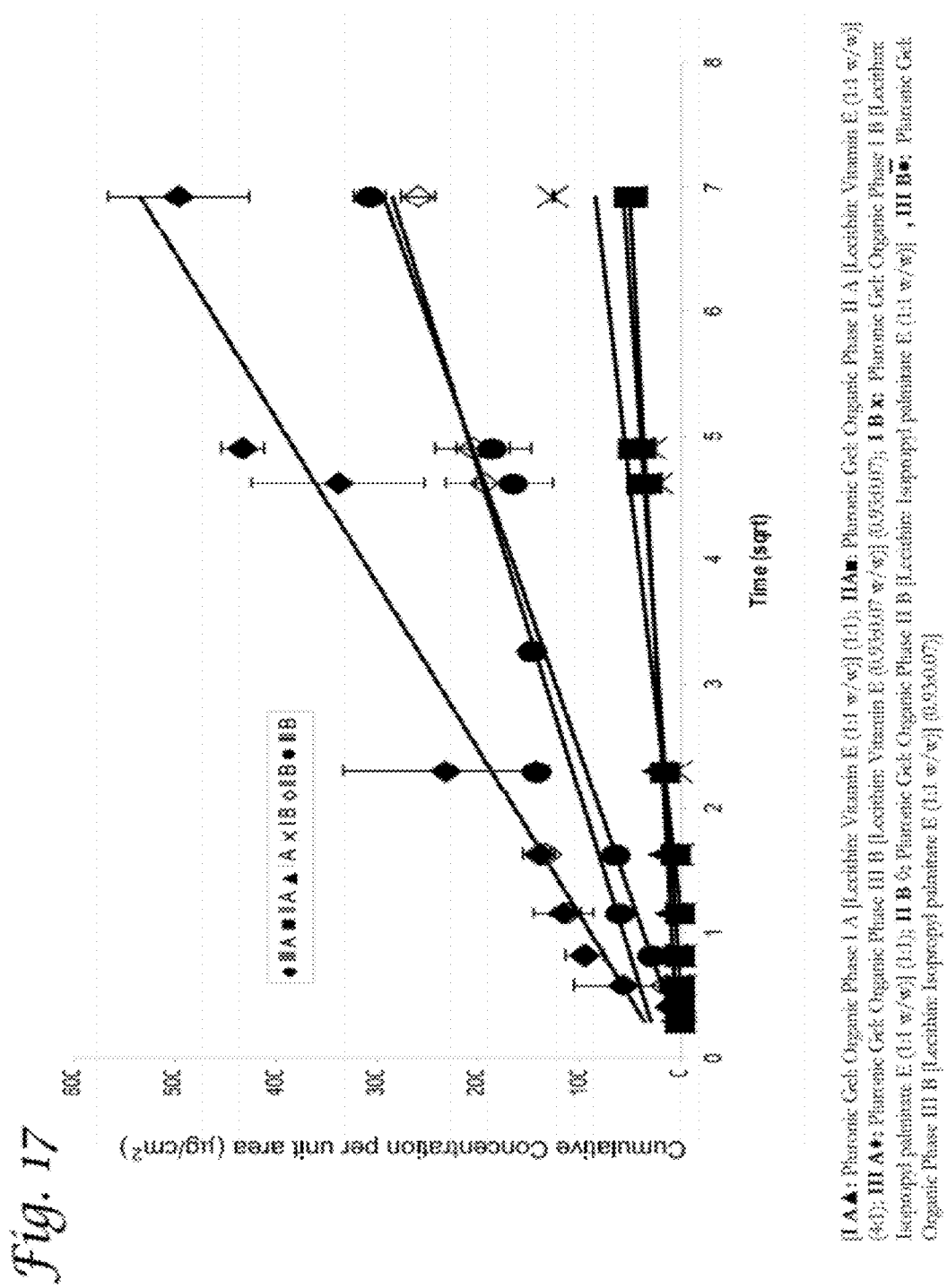
FIG. 17 is a graph showing physicochemical data obtained from the permeation of N-acetyl glucosamine in pluronic gel-organic phase vehicles through shed snake skin.

Initially NAG transport was observed from lecithin-isopropyl palmitate, vitamin E, and lecithin-vitamin E (1:1) suspensions (100 mg/ml). Negligible (below the limit of detection) transport was observed from all of these suspensions, excluding the permeation of NAG from the lecithin-vitamin mixed E (1:1) suspension shown in FIG. 17, showing physicochemical data obtained for the permeation of NAG in pluronic gel-organic phase vehicles through shed snake skin, cumulative concentration (n=3) per unit area +/− standard deviation as a function of time$^{1/2}$ (IA: 1:1 w/w of pluronic gel:organic phase IA (lecithin:vitamin E (1:1 w/w)); IIA: 4:1 w/w of pluronic gel:organic phase IIA (lecithin:vitamin E (1:1 w/w)); IIIA: 0.93:0.07 w/w of pluronic gel:organic phase IIIA (lecithin:vitamin E (0.93:0.07 w/w)); IIB: 1:1 w/w of plutonic gel:organic phase IB (lecithin:isopropyl palmitate (1:1 w/w)); IIB: 1:1 w/w of pluronic gel:organic phase IIB (lecithin:isopropyl palmitate (1:1 w/w)); IIIB: 0.93:0.07 w/w of pluronic gel:organic phase IB (lecithin:isopropyl palmitate (1:1 w/w)).

Relatively, linear transport was observed from the lecithin-vitamin mixed E (1:1) suspension. NAG's release rate=13.71

μg/cm², steady state flux $J_{ss}$=4.23 μg/cm²/h and its permeability coefficient $k_p$=5.012×10⁻³ (cm/h) have been recorded (Table 4).

TABLE 4

Physicochemical data obtained for the permeation of N-acetylglucosamine (NAG) in a lecithin-vitamin pluronic-organic phase vehicle through shed snakeskin.

| Vehicle | $J_{ss}$ (mg/cm²/h) | Release rate (mg/cm²) | $k_p$ (cm/h) | $t_{lag}$ (h²) |
|---|---|---|---|---|
| Lecithin-Vitamin E (1:1) | 4.23 g/cm²/h | 13.71 μg/cm² | 5.012 × 10⁻³ | 0 |

For the pluronic organo-gels, each vehicle was composed of a pluronic gel and organic phase, as shown in Table 5, along with its respective physicochemical data obtained for the permeation of N-acetylglucosamine (NAG). Each NAG vehicle exhibited lag time, as reported in Table 5. The cumulative concentration versus time plot to obtain $t_{lag}$ is not shown. As exhibited in FIG. 17, the cumulative concentration per unit area versus the square root of time plot shows a comparison of all the vehicles. Overall graphically, the pluronic gel formulations containing organic phase mix of lecithin and isopropyl palmitate out-performed the pluronic gel containing lecithin and vitamin E organic phase vehicles. Formulation III A, which contained the pluronic gel to lecithin-vitamin E mix at a 0.93:0.7 exhibited the best release rate, steady state flux and permeability coefficient values (Table 5).

The data shows that as the organic enhancer phase is decreased, NAG permeation increases for both formulations III A and III B. However, the release rates of formulations II B and III B are comparable. Correspondingly, in experiments not reported here, NAG was not transported in aqueous only vehicles.

TABLE 5

Physicochemical data obtained for the permeation of NAG in pluronic-organic phase vehicles through shed snakeskin.

| Vehicle | Graphical Label | Organic Phase | $J_{ss}$ (mg/cm²/h) | Release rate (mg/cm²) | $k_p$ (cm/h) | $t_{lag}$ (h) |
|---|---|---|---|---|---|---|
| Pluronic Gel:Organic Phase I A (1:1) | I A | Lecithin:Vitamin E (1:1 w/w) | 1.01 | 6.88 | 3.2 × 10⁻³ | 6.45 |
| Pluronic Gel:Organic Phase II A (4:1) | II A | Lecithin:Vitamin E (1:1 w/w) | 1.06 | 8.94 | 3.1 × 10⁻³ | 3.98 |
| Pluronic Gel:Organic Phase III A (0.93:0.7) | III A | Lecithin:Vitamin E (1:1 w/w) | 10.3 | 74.9 | 3.2 × 10⁻¹ | 0.85 |
| Pluronic Gel:Organic Phase I B (1:1) | I B | Lecithin:Isopropyl palmitate E (1:1 w/w) | 2.16 | 14.6 | 3.1 × 10⁻⁴ | 5.33 |
| Pluronic Gel:Organic Phase II B (4:1) | II B | Lecithin:Isopropyl palmitate E (1:1 w/w) | 6.98 | 38.5 | 2.5 × 10⁻⁴ | 6.98 |
| Pluronic Gel:Organic Phase III B (0.93:0.7) | III B | Lecithin:Isopropyl palmitate E (1:1 w/w) | 4.46 | 43.1 | 6.8 × 10⁻⁴ | 2.49 |

The complete disclosures of all patents, patent applications, provisional patent applications, publications, and electronically available material cited herein are incorporated by reference. The foregoing detailed description and examples have been provided for clarity of understanding only. No unnecessary limitations are to be understood therefrom. The invention is not limited to the exact details shown and described; many variations will be apparent to one skilled in the art and are intended to be included within the invention defined by the claims.

What is claimed is:

1. A compound comprising a first component covalently linked to a second component, X, said compound having formula I:

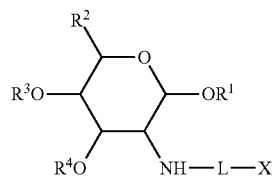

wherein:

$R^1$, $R^2$, $R^3$ and $R^4$ are each independently H or an organic group;

L is an optional linking group; and

X is an anti-inflammatory agent selected from the group consisting of a prostaglandin, an arachidonic acid, and a metabolite of arachidonic acid.

2. The compound of claim 1 wherein L, if present, is an organic group.

3. The compound of claim 1 wherein the first component is selected from the group consisting of glucosamine, glucosamine pentaacetate, glucosamine-1-phosphate, glucosamine-6-phosphate, N-acetyl-β-D-glucosamine, N-acetylglucosamine-6-phosphate, N-acetyl-glucosamine-1-phosphate, uridine diphosphate-N-acetyl glucosamine, 2-amino-2-deoxy-1,3,4,6-acetyl-β-D-glucopyranose, the acetylated analog of 2-amino-2-deoxy-1,3,4,6-acetyl-β-D-glucopyranose, 2-acetamido-2-deoxy-β-D-glucopyranose-1,3,4,6-tetraacetate, the acetylated analog of 2-acetamido-2-deoxy-β-D-glucopyranose-1,3,4,6-tetraacetate, and N-acetyl-glucosamine.

4. A pharmaceutical composition comprising a therapeutically effective amount of at least one compound comprising a first component covalently linked to a second component, X, said compound having formula I:

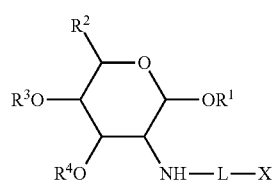

wherein:

$R^1$, $R^2$, $R^3$ and $R^4$ are each independently H or an organic group;

L is an optional linking group; and

X is an anti-inflammatory agent selected from the group consisting of a prostaglandin, an arachidonic acid, and a metabolite of arachidonic acid;
and a pharmaceutically acceptable carrier.

5. The pharmaceutical composition of claim 4 further comprising one or more additional components selected from the group consisting of an antimicrobial agent, a gelling agent, an emulsifying agent, a stiffening agent, a skin healing agent, an emollient, a surfactant, a solvent, a lubricant, a wax, a humectant, a skin penetration enhancer, an antioxidant, and combinations thereof.

6. The pharmaceutical composition of claim 5 wherein the antimicrobial agent is selected from the group consisting of ethanol, paraben, salts of a paraben, sorbic acid, potassium sorbate, propylene glycol, glycerin, and combinations thereof.

7. The pharmaceutical composition of claim 5 wherein the skin healing agent is selected from the group consisting of vitamin E, ascorbic acid, alpha tocopherol, beta tocopherol, gamma tocopherol, aloe vera, vitamin E-TPGS, and combinations thereof.

8. The pharmaceutical composition of claim 5 wherein the emulsifying agent is selected from the group consisting of cholesterol, poloxamers, lecithin, carbomers, polyoxyethylene ethers, fatty acid esters, stearates, and combinations thereof.

9. The pharmaceutical composition of claim 5 wherein the skin penetration enhancer is selected from the group consisting of dimethyl sulfoxide, ethanol, polyethylene glycol, urea, dimethyl acetamide, sodium lauryl sulfate, Spans, Tweens, terpenes, azone, acetone, oleic acid, and combinations thereof.

10. The pharmaceutical composition of claim 5 wherein the antioxidant is selected from the group consisting of fumaric acid, malic acid, ascorbic acid palmitate, butylated hydroxylanisole, propyl gallate, sodium ascorbate, sodium metabisulfite, and combinations thereof.

11. The pharmaceutical composition of claim 4 wherein the composition is formulated for topical application.

12. The pharmaceutical composition of claim 4 wherein the carrier is selected from an ointment, a gel, a cream, a solution, a lotion, a suspension, a microemulsion, an emulsion, a liposome, or a transdermal patch.

13. The pharmaceutical composition of claim 4 wherein the composition is formulated for subcutaneous, intramuscular, or intravenous administration.

14. The pharmaceutical composition of claim 4 wherein the composition is formulated for oral administration.

15. The pharmaceutical composition of claim 4 wherein the first component is present in the composition in an amount of about 1 weight percent to about 75 weight percent.

16. A method for treating or preventing a disorder or condition in a mammal, the method comprising administering to a mammal a therapeutically effective amount of a pharmaceutical composition comprising at least one compound selected from the group consisting of:
(a) a compound comprising a first component covalently linked to a second component, X, said compound having formula I:

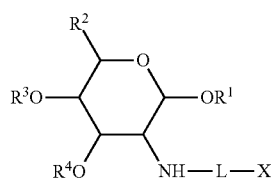

(I)

wherein:
$R^1$, $R^2$, $R^3$ and $R^4$ are each independently H or an organic group;
L is an optional linking group; and
X is an anti-inflammatory agent selected from the group consisting of a prostaglandin, an arachidonic acid, and a metabolite of arachidonic acid; and
(b) a compound having formula II:

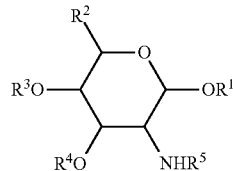

(II)

wherein:
$R^1$, $R^2$, $R^3$, $R^4$ and $R^5$ are each independently H or an organic group;
and a pharmaceutically acceptable carrier;
wherein the disorder or condition is selected from the group consisting of arthritis, osteoarthritis, osteoporosis, muscle sprains, muscle strains, joint sprains, joint strains, tendonitis, bursitis, burns, joint pain, inflamed joints, skin damage, skin tenderness, skin pain, sun-damaged skin, wind-damaged skin, salt-damaged skin, scar tissue, age-related wrinkling of the skin, and combinations thereof.

17. The method of claim 16 wherein treating the disorder or condition comprises alleviating at least one symptom of the disorder.

18. The method of claim 16 wherein administering the composition comprises topical administration.

19. The method of claim 16 wherein the composition is formulated for use as a cosmetic.

20. The method of claim 16 wherein administering the composition comprises subcutaneous, intramuscular, or intravenous administration.

21. The method of claim 16 wherein administering the composition comprises oral administration.

22. The method of claim 16 wherein the mammal is a human.

23. A pharmaceutical composition comprising a therapeutically effective amount of a compound comprising a first component covalently linked to a second component, X, said compound having formula I:

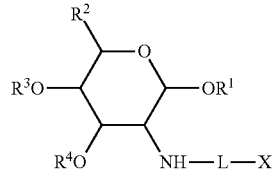

(I)

wherein:
$R^1$, $R^2$, $R^3$, and $R^4$ are each H;
L is an acetyl group; and
X is an anti-inflammatory agent selected from the group consisting of a prostaglandin, an arachidonic acid, and a metabolite of arachidonic acid;
and a pharmaceutically acceptable carrier; said composition formulated for topical application.

24. A method to alleviate a disease characterized by degeneration of cartilage or other joint connective tissues comprising:
   administering to a mammal an effective amount of a compound comprising a first component covalently linked to a second component, X, said compound having formula I:

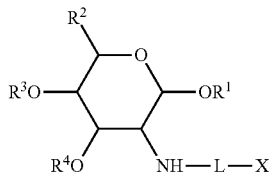

(I)

wherein:
   $R^1$, $R^2$, $R^3$, and $R^4$ are each independently H or an organic group;
   L is an optional linking group; and
   X is an anti-inflammatory agent selected from the group consisting of a prostaglandin, an arachidonic acid, and a metabolite of arachidonic acid.

25. A method to alleviate pain and inflammation associate with osteoarthritis comprising:
   administering to a mammal an effective amount of a compound comprising a first component covalently linked to a second component, X, said compound having formula I

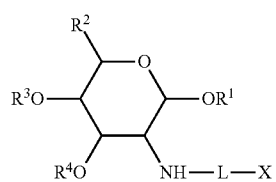

(I)

wherein:
   $R^1$, $R^2$, $R^3$, and $R^4$ are each independently H or an organic group;
   L is an optional linking group; and
   X is an anti-inflammatory agent selected from the group consisting of a prostaglandin, an arachidonic acid, and a metabolite of arachidonic acid.

* * * * *